(12) United States Patent
Syken et al.

(10) Patent No.: US 6,825,005 B2
(45) Date of Patent: Nov. 30, 2004

(54) METHODS AND REAGENTS TO REGULATE APOPTOSIS

(75) Inventors: Joshua Syken, Jamaica Plain, MA (US); Karl Münger, Newton, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 09/908,992

(22) Filed: Jul. 19, 2001

(65) Prior Publication Data

US 2002/0086844 A1 Jul. 4, 2002

Related U.S. Application Data

(60) Provisional application No. 60/219,718, filed on Jul. 19, 2000, and provisional application No. 60/219,537, filed on Jul. 20, 2000.

(51) Int. Cl.$^7$ .......................... C12P 21/06; C12N 15/74; C12N 5/02; C12N 15/09; C07H 21/04
(52) U.S. Cl. .................. 435/69.1; 435/320.1; 435/325; 435/455; 536/23.1
(58) Field of Search ...................... 536/23.1; 435/320.1, 435/69.1, 455, 325

(56) References Cited

PUBLICATIONS

Chemical Compound, Encyclopedia Britannica online.*
Bowie et al, Science Mar. 1990; 247:1306–10.*
Bos, EMBO J 1998;17:6776–82.*
Ngo, in The Protein Folding Problem and Tertiary Structure Prediction, Merz et al. (eds.), Birkhauser Boston: Boston, MA, pp. 433 and 492–495, 1994.*
Rudinger, in Peptide Hormones, Parsons (ed.), University Park Press: Baltimore, MD, pp. 1–7, 1976.*
Han et al, Sequence ID AF244136, GenEmbl, Apr. 30, 2000.*
Rescan, P. (1997), Identification in a fish species of two ld (inhibitor of DNA binding/differentiation)–related helix–loop–helix factors expressed in the slow oxidative muscle fibers, Eur. J. Biochem. 247:870–876.
Schilling et al. (1998), A Novel Human DnaJ Protein, hTid–1, a Homolog of the Drosophila Tumor Suppressor Protein Tid56, Can Interact with the Human Papillomavirus Type 16 E7 Oncoprotein, VIROLOGY. 247:74–85.
Kurzik–Dumke et al. (1998), Mitochondrial localization and temporal expression of the Drosophila melanogaster DnaJ homologous tumor suppressor Tid50, Cell Stress and Chaperones. 3:12–27.
Syken et al. (1999), TID1, a human homolog of the Drosophila tumor suppressor 1(2)tid, encodes two mitochondrial modulator of apoptosis with opposing functions, Proc. Natl. Acad. Sci. 96:8499–8504.

* cited by examiner

*Primary Examiner*—Janice Li
(74) *Attorney, Agent, or Firm*—Foley Hoag, LLP

(57) ABSTRACT

The invention provides isolated nucleic acids and vectors encoding two splice forms of Tid1 (Tid-1L and Tid-1S) and cells and non-human organisms comprising such. The invention further provides methods for modulating apoptosis in a cell by modulating the amount and/or activity of these two splice forms relative to each other. Such methods can be used in vivo and in vitro, e.g., in cell cultures, for either making cells more susceptible to apotosis or more resistant to it.

36 Claims, 21 Drawing Sheets hTid-1L carboxyl terminus
SSGGSTMDSSAGSKARREAGEDEEGFLSKLKKMFTS hTid-1S carboxyl terminus
SSGKRSTGN

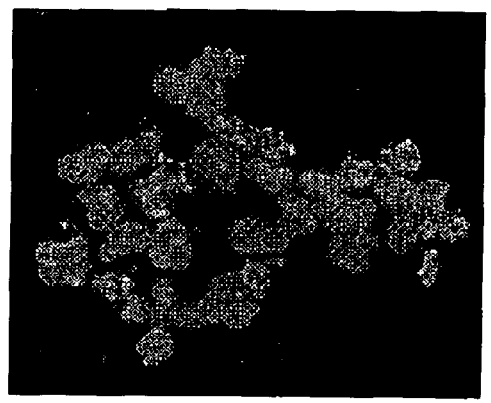
U2OS
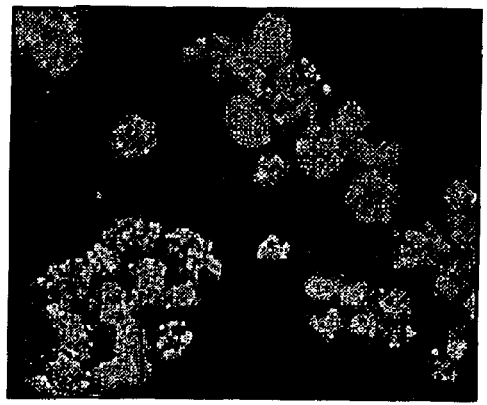
hTid-1$_L$
hTid-1$_S$
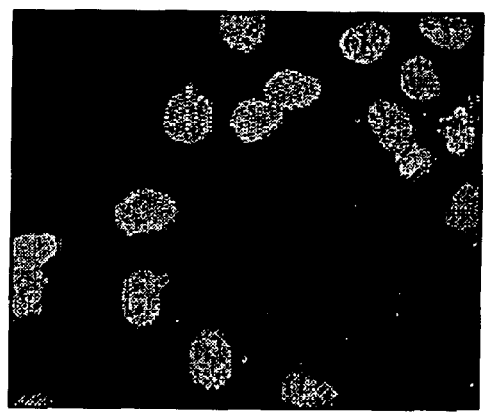
H121Q$_L$
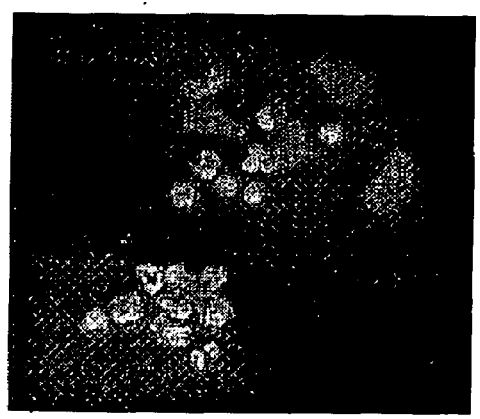
H121Q$_S$
FIG. 3C Nucelotide sequence of coding sequence encoding hTid1L:

ATGgctgcgcggtgctccacacgctggttgctggtggttgtggggaccccgcggctgccggctatatcgggtagaggggc
ccggccgcccagggagggcgtggtgggggcatggctgagccgcaagctgagcgtccccgcctttgcgtcttccctgacct
cttgcggcccccgagcgctgctgacattgagacctggtgtcagccttacaggaacaaaacataacccttcatttgtact
gcctccttccacacgagtgcccctttggccaaagaagattattatcagatattaggagtgcctcgaaatgccagccagaa
agagatcaagaaagcctattatcagcttgccaagaagtatcaccctgacacaaataaggatgatcccaaagccaaggaga
agttctcccagctggcagaagcctatgaggttttgagtgatgaggtgaagaggaagcagtacgatgcctacggctctgca
ggcttcgatcctggggccagcggctcccagcatagctactggaagggaggcccactgtggaccccgaggagctgttcag
gaagatctttggcgagttctcatcctcttcatttggagatttccagaccgtgtttgatcagcctcaggaatacttcatgg
agttgacattcaatcaagctgcaaagggggtcaacaaggagttcaccgtgaacatcatggacacgtgtgagcgctgcaac
ggcaaggggaacgagcccggcaccaaggtgcagcattgccactactgtggcggctccggcatggaaaccatcaacacagg
ccctttgtgatgcgttccacgtgtaggagatgtggtggccgcggctccatcatcatatcgccctgtgtggtctgcaggg
gagcaggacaagccaagcagaaaaagcgagtgatgatccctgtgcctgcaggagtcgaggatggccagaccgtgaggatg
cctgtgggaaaaagggaaattttcattacgttcagggtgcagaaaagccctgtgttccggagggacggcgcagacatcca
ctccgacctctttatttctatagctcaggctcttcttgggggaacagccagagcccagggcctgtacgagacgatcaacg
tgacgatcccccctgggactcagacagaccagaagattcggatgggtgggaaaggcatcccccggattaacagctacggc
tacggagaccactacatccacatcaagatacgagttccaaagaggctaacgagccggcagcagagcctgatcctgagcta
cgccgaggacgagacagatgtggaggggacggtgaacggcgtcaccctcaccagctctggtggcagcaccatggatagct
ccgcaggaagcaaggctaggcgtgaggctggggaggacgaggagggattcctttccaaacttaagaaaatgtttacctca
TGA Nucelotide sequence of coding sequence encoding hTid1S:

atggctgcGcggtgctccacacgctggttgctggtggttgtggggaccccgcggctgccggctatatcgggtagaggggc
ccggccgcccagggagggcgtggtgggggcatggctgagccgcaagctgagcgtccccgcctttgcgtcttccctgacct
cttgcggcccccgagcgctgctgacattgagacctggtgtcagccttacaggaacaaaacataacccttcatttgtact
gcctccttccacacgagtgcccctttggccaaagaagattattatcagatattaggagtgcctcgaaatgccagccagaa
agagatcaagaaagcctattatcagcttgccaagaagtatcaccctgacacaaataaggatgatcccaaagccaaggaga
agttctcccagctggcagaagcctatgaggttttgagtgatgaggtgaagaggaagcagtacgatgcctacggctctgca
ggcttcgatcctggggccagcggctcccagcatagctactggaagggaggcccactgtggaccccgaggagctgttcag
gaagatctttggcgagttctcatcctcttcatttggagatttccagaccgtgtttgatcagcctcaggaatacttcatgg
agttgacattcaatcaagctgcaaagggggtcaacaaggagttcaccgtgaacatcatggacacgtgtgagcgctgcaac
ggcaaggggaacgagcccggcaccaaggtgcagcattgccactactgtggcggctccggcatggaaaccatcaacacagg
ccctttgtgatgcgttccacgtgtaggagatgtggtggccgcggctccatcatcatatcgccctgtgtggtctgcaggg
gagcaggacaagccaagcagaaaaagcgagtgatgatccctgtgcctgcaggagtcgaggatggccagaccgtgaggatg
cctgtgggaaaaagggaaattttcattacgttcagggtgcagaaaagccctgtgttccggagggacggcgcagacatcca
ctccgacctctttatttctatagctcaggctcttcttgggggaacagccagagcccagggcctgtacgagacgatcaacg
tgacgatcccccctgggactcagacagaccagaagattcggatgggtgggaaaggcatcccccggattaacagctacggc
tacggagaccactacatccacatcaagatacgagttccaaagaggctaacgagccggcagcagagcctgatcctgagcta
cgccgaggacgagacagatgtggaggggacggtgaacggcgtcaccctcaccagctctggAAAAAGATCCACTGGAAACT
AG

FIG. 5

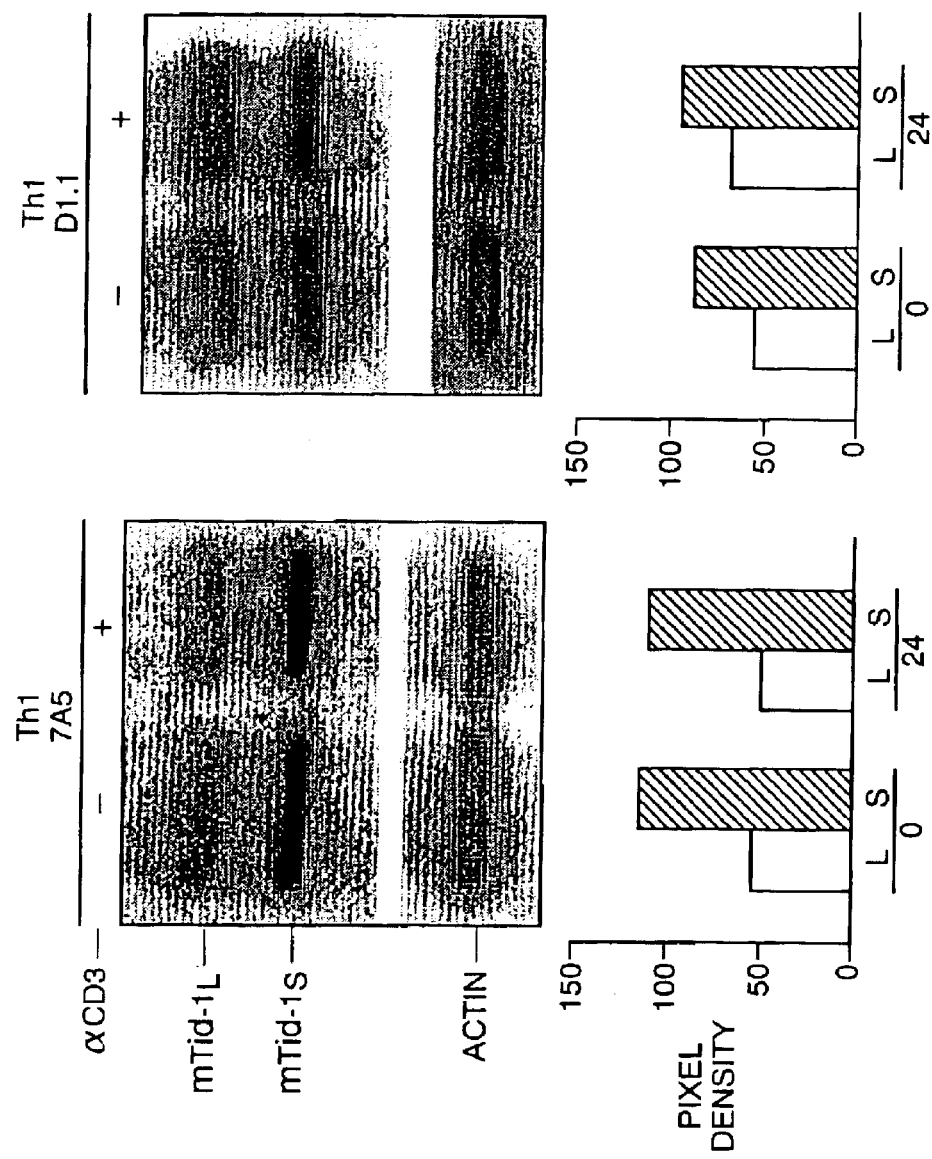
FIG. 7F1

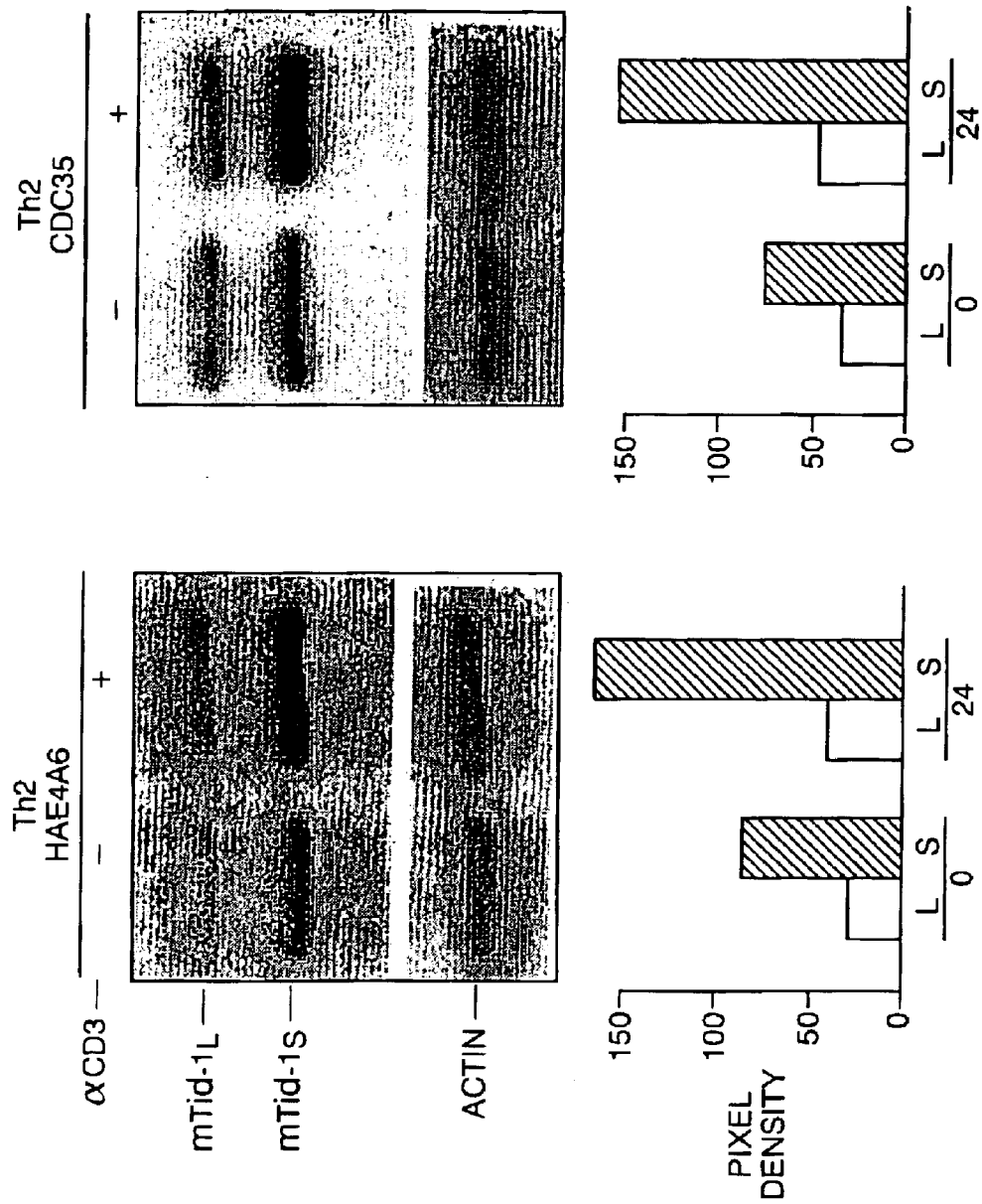
FIG. 7F2

Amino acid sequence of mTid-1L:

MAAWCSPRWLRVAVGTPRLPAAAGRGVQQPQGGVVATSLCRKLCVSAFGLSMG
AHGPRALLTLRPGVRLTGTKSFPFVCTTSFHTSASLAKDDYYQILGVPRNASQKDI
KKAYYQLAKKYHPDTNKDDPKAKEKFSQLAEAYEVLSDEVKRKQYDAYGSAGF
DPGTSSSGQGYWRGGPSVDPEELFRKIFGEFSSSPFGDFQNVVXXXXXXXXXXXX
XXXXXXXKEFTVNIMDTCERCDGKGNEPGTKVQHCHYCGGSGMETINTGPFVMR
STCRRCGGRGSIITNPCVVCRGAGQAKQKKRVTIPVPAGVEDGQTVRMPVGKREIF
VTFRVQKSPVFRRTCADIHSDLFISIAQAILGGTAKAQGLYETINVTIPAGIQTDQKI
RLTGKGIPRINSYGYGDHYIHIKIRVPKRLSSRQQNLILSYAEDETDVEGTVNGVTH
TSTGGRTMDSSAESKDRREAGEDNEGFLSKLKKIFTS

Amino acid sequence of mTid-1S:

MAAWCSPRWLRVAVGTPRLPAAAGRGVQQPQGGVVATSLCRKLCVSAFGLSMG
AHGPRALLTLRPGVRLTGTKSFPFVCTTSFHTSASLAKDDYYQILGVPRNASQKDI
KKAYYQLAKKYHPDTNKDDPKAKEKFSQLAEAYEVLSDEVKRKQYDAYGSAGF
DPGTSSSGQGYWRGGPSVDPEELFRKIFGEFSSSPFGDFQNVVXXXXXXXXXXXX
XXXXXXXKEFTVNIMDTCERCDGKGNEPGTKVQHCHYCGGSGMETINTGPFVMR
STCRRCGGRGSIITNPCVVCRGAGQAKQKKRVTIPVPAGVEDGQTVRMPVGKREIF
VTFRVQKSPVFRRTCADIHSDLFISIAQAILGGTAKAQGLYETINVTIPAGIQTDQKI
RLTGKGIPRINSYGYGDHYIHIKIRVPKRLSSRQQNLILSYAEDETDVEGTVNGVTH
TSTGKRSTGN

FIG. 10

SEQUENCE LISTING

<160> NUMBER OF SEQ ID NOS: 27

<210> SEQ ID NO 1
<211> LENGTH: 2656
<212> TYPE: DNA
<213> ORGANISM: Homo sapiens
<220> FEATURE:
<221> NAME/KEY: CDS
<222> LOCATION: (32)..(1471)

<400> SEQUENCE: 1

```
gaattcgcgg ccgcagagtc cccgggccaa g atg gct gcg cgg tgc tcc aca            52
                                   Met Ala Ala Arg Cys Ser Thr
                                     1               5 cgc tgg ttg ctg gtg gtt gtg ggg acc ccg cgg ctg ccg gct ata tcg          100
Arg Trp Leu Leu Val Val Val Gly Thr Pro Arg Leu Pro Ala Ile Ser
            10                  15                  20 ggt aga ggg gcc cgg ccg ccc agg gag ggc gtg gtg ggg gca tgg ctg          148
Gly Arg Gly Ala Arg Pro Pro Arg Glu Gly Val Val Gly Ala Trp Leu
 25                  30                  35 agc cgc aag ctg agc gtc ccc gcc ttt gcg tct tcc ctg acc tct tgc          196
Ser Arg Lys Leu Ser Val Pro Ala Phe Ala Ser Ser Leu Thr Ser Cys
 40                  45                  50                  55 ggc ccc cga gcg ctg ctg aca ttg aga cct ggt gtc agc ctt aca gga          244
Gly Pro Arg Ala Leu Leu Thr Leu Arg Pro Gly Val Ser Leu Thr Gly
             60                  65                  70 aca aaa cat aac cct ttc att tgt act gcc tcc ttc cac acg agt gcc          292
Thr Lys His Asn Pro Phe Ile Cys Thr Ala Ser Phe His Thr Ser Ala
             75                  80                  85 cct ttg gcc aaa gaa gat tat tat cag ata tta gga gtg cct cga aat          340
Pro Leu Ala Lys Glu Asp Tyr Tyr Gln Ile Leu Gly Val Pro Arg Asn
         90                  95                 100 gcc agc cag aaa gag atc aag aaa gcc tat tat cag ctt gcc aag aag          388
Ala Ser Gln Lys Glu Ile Lys Lys Ala Tyr Tyr Gln Leu Ala Lys Lys
        105                 110                 115 tat cac cct gac aca aat aag gat gat ccc aaa gcc aag gag aag ttc          436
Tyr His Pro Asp Thr Asn Lys Asp Asp Pro Lys Ala Lys Glu Lys Phe
120                 125                 130                 135 tcc cag ctg gca gaa gcc tat gag gtt ttg agt gat gag gtg aag agg          484
Ser Gln Leu Ala Glu Ala Tyr Glu Val Leu Ser Asp Glu Val Lys Arg
                140                 145                 150 aag cag tac gat gcc tac ggc tct gca ggc ttc gat cct ggg gcc agc          532
Lys Gln Tyr Asp Ala Tyr Gly Ser Ala Gly Phe Asp Pro Gly Ala Ser
            155                 160                 165 ggc tcc cag cat agc tac tgg aag gga ggc ccc act gtg gac ccc gag          580
Gly Ser Gln His Ser Tyr Trp Lys Gly Gly Pro Thr Val Asp Pro Glu
        170                 175                 180 gag ctg ttc agg aag atc ttt ggc gag ttc tca tcc tct tca ttt gga          628
Glu Leu Phe Arg Lys Ile Phe Gly Glu Phe Ser Ser Ser Ser Phe Gly
185                 190                 195 gat ttc cag acc gtg ttt gat cag cct cag gaa tac ttc atg gag ttg          676
Asp Phe Gln Thr Val Phe Asp Gln Pro Gln Glu Tyr Phe Met Glu Leu
200                 205                 210                 215 aca ttc aat caa gct gca aag ggg gtc aac aag gag ttc acc gtg aac          724
Thr Phe Asn Gln Ala Ala Lys Gly Val Asn Lys Glu Phe Thr Val Asn
                220                 225                 230 atc atg gac acg tgt gag cgc tgc aac ggc aag ggg aac gag ccc ggc          772
Ile Met Asp Thr Cys Glu Arg Cys Asn Gly Lys Gly Asn Glu Pro Gly
            235                 240                 245
```

-continued

```
acc aag gtg cag cat tgc cac tac tgt ggc ggc tcc ggc atg gaa acc      820
Thr Lys Val Gln His Cys His Tyr Cys Gly Gly Ser Gly Met Glu Thr
        250                 255                 260 atc aac aca ggc cct ttt gtg atg cgt tcc acg tgt agg aga tgt ggt      868
Ile Asn Thr Gly Pro Phe Val Met Arg Ser Thr Cys Arg Arg Cys Gly
    265                 270                 275 ggc cgc ggc tcc atc atc ata tcg ccc tgt gtg gtc tgc agg gga gca      916
Gly Arg Gly Ser Ile Ile Ile Ser Pro Cys Val Val Cys Arg Gly Ala
280                 285                 290                 295 gga caa gcc aag cag aaa aag cga gtg atg atc cct gtg cct gca gga      964
Gly Gln Ala Lys Gln Lys Lys Arg Val Met Ile Pro Val Pro Ala Gly
                300                 305                 310 gtc gag gat ggc cag acc gtg agg atg cct gtg gga aaa agg gaa att     1012
Val Glu Asp Gly Gln Thr Val Arg Met Pro Val Gly Lys Arg Glu Ile
            315                 320                 325 ttc att acg ttc agg gtg cag aaa agc cct gtg ttc cgg agg gac ggc     1060
Phe Ile Thr Phe Arg Val Gln Lys Ser Pro Val Phe Arg Arg Asp Gly
        330                 335                 340 gca gac atc cac tcc gac ctc ttt att tct ata gct cag gct ctt ctt     1108
Ala Asp Ile His Ser Asp Leu Phe Ile Ser Ile Ala Gln Ala Leu Leu
    345                 350                 355 ggg gga aca gcc aga gcc cag ggc ctg tac gag acg atc aac gtg acg     1156
Gly Gly Thr Ala Arg Ala Gln Gly Leu Tyr Glu Thr Ile Asn Val Thr
360                 365                 370                 375 atc ccc cct ggg act cag aca gac cag aag att cgg atg ggt ggg aaa     1204
Ile Pro Pro Gly Thr Gln Thr Asp Gln Lys Ile Arg Met Gly Gly Lys
                380                 385                 390 ggc atc ccc cgg att aac agc tac ggc tac gga gac cac tac atc cac     1252
Gly Ile Pro Arg Ile Asn Ser Tyr Gly Tyr Gly Asp His Tyr Ile His
            395                 400                 405 atc aag ata cga gtt cca aag agg cta acg agc cgg cag cag agc ctg     1300
Ile Lys Ile Arg Val Pro Lys Arg Leu Thr Ser Arg Gln Gln Ser Leu
        410                 415                 420 atc ctg agc tac gcc gag gac gag aca gat gtg gag ggg acg gtg aac     1348
Ile Leu Ser Tyr Ala Glu Asp Glu Thr Asp Val Glu Gly Thr Val Asn
    425                 430                 435 ggc gtc acc ctc acc agc tct ggt ggc agc acc atg gat agc tcc gca     1396
Gly Val Thr Leu Thr Ser Ser Gly Gly Ser Thr Met Asp Ser Ser Ala
440                 445                 450                 455 gga agc aag gct agg cgt gag gct ggg gag gac gag gag gga ttc ctt     1444
Gly Ser Lys Ala Arg Arg Glu Ala Gly Glu Asp Glu Glu Gly Phe Leu
                460                 465                 470 tcc aaa ctt aag aaa atg ttt acc tca tgatatccca gccgaggaaa           1491
Ser Lys Leu Lys Lys Met Phe Thr Ser
            475                 480 aagatccact ggaaactagg ccgggaagca gcagcccctc caagggccag ggcacctggg   1551
agacgggagg attccagaac agcagcactg agctcccacc cgcagagcct ctggacggcc   1611
ttggcaacag caaaatcatg ggacaacacc tctctccacg gaaggtcac agtggacagc    1671 ccgggcagta ggatgcagcc ccagaggctg gtggcagttt cctgtccatt ggtaggtgac   1731 ggcccccctgg tcagcagagg agaggttaga tcttgcaggc taaaactcta atttggaatt  1791
gaatattgtg gatatcttag ttaaaggcca tgcttacagc ttagaaatga agccttaagc   1851
tgcatcaagt tacgaagtga ttaatttcct tctcagcaaa cctccgggag gttccagaat   1911
gagttcttcc tgacaggttg tcttcactgg gagcgtgggg cccccaggcc ccaccagcac   1971
cgtcctcccc taatgagggg ccctgccgag gcatcagctg ctctgctcag ttagttttta   2031
```

-continued

```
ttcccggggt accaagcagc tgcacagtcg gtgcctggga agcacgttaa aggcccagag    2091
agatcctggg ggttctgctc tgaccgtgtg ggtggtgatc cttgtcagga tgtacagtcc    2151
ttgctcccac cccatccggg atggccgcct gtccctgact attgagtcct gttgttgtaa    2211
gccaggcatg gagggctcct gcccttctgc tgagccacag cccattgcag cactgtgctg    2271
gccagacttc agctgccttg ggaactgaag ccctgccact gttgctagtc aggggcttgg    2331
ttctcccact tacactgttg acatctattt tctgaagtgt gtttaaatta ttcagtgcta    2391
atcattgttt tttcctttgt aaatgttgat tcagaaaagg aaagcacagg ctaagcagtt    2451
gaaggttccc caccattcag tgagagcaga accccccattc cccagcctct gctggtagca    2511
tgtcgcagtt tccatgtgtt tcaggatctt cgggctgtcg ttagacaggt taatgaagaa    2571
cacttctcaa cagtttcctt tttgttttcc tttataattc actaaaataa agcatctatt    2631
agtgtctgaa aaaaaaaaa aaaaa                                           2656
```

<210> SEQ ID NO 2
<211> LENGTH: 1443
<212> TYPE: DNA
<213> ORGANISM: Homo sapiens
<220> FEATURE:
<221> NAME/KEY: CDS
<222> LOCATION: (1)..(1440)

<400> SEQUENCE: 2

```
atg gct gcg cgg tgc tcc aca cgc tgg ttg ctg gtg gtt gtg ggg acc     48
Met Ala Ala Arg Cys Ser Thr Arg Trp Leu Leu Val Val Val Gly Thr
 1               5                  10                  15 ccg cgg ctg ccg gct ata tcg ggt aga ggg gcc cgg ccg ccc agg gag     96
Pro Arg Leu Pro Ala Ile Ser Gly Arg Gly Ala Arg Pro Pro Arg Glu
             20                  25                  30 ggc gtg gtg ggg gca tgg ctg agc cgc aag ctg agc gtc ccc gcc ttt    144
Gly Val Val Gly Ala Trp Leu Ser Arg Lys Leu Ser Val Pro Ala Phe
         35                  40                  45 gcg tct tcc ctg acc tct tgc ggc ccc cga gcg ctg ctg aca ttg aga    192
Ala Ser Ser Leu Thr Ser Cys Gly Pro Arg Ala Leu Leu Thr Leu Arg
     50                  55                  60 cct ggt gtc agc ctt aca gga aca aaa cat aac cct ttc att tgt act    240
Pro Gly Val Ser Leu Thr Gly Thr Lys His Asn Pro Phe Ile Cys Thr
 65                  70                  75                  80 gcc tcc ttc cac acg agt gcc cct ttg gcc aaa gaa gat tat tat cag    288
Ala Ser Phe His Thr Ser Ala Pro Leu Ala Lys Glu Asp Tyr Tyr Gln
                 85                  90                  95 ata tta gga gtg cct cga aat gcc agc cag aaa gag atc aag aaa gcc    336
Ile Leu Gly Val Pro Arg Asn Ala Ser Gln Lys Glu Ile Lys Lys Ala
            100                 105                 110 tat tat cag ctt gcc aag aag tat cac cct gac aca aat aag gat gat    384
Tyr Tyr Gln Leu Ala Lys Lys Tyr His Pro Asp Thr Asn Lys Asp Asp
        115                 120                 125 ccc aaa gcc aag gag aag ttc tcc cag ctg gca gaa gcc tat gag gtt    432
Pro Lys Ala Lys Glu Lys Phe Ser Gln Leu Ala Glu Ala Tyr Glu Val
    130                 135                 140 ttg agt gat gag gtg aag agg aag cag tac gat gcc tac ggc tct gca    480
Leu Ser Asp Glu Val Lys Arg Lys Gln Tyr Asp Ala Tyr Gly Ser Ala
145                 150                 155                 160 ggc ttc gat cct ggg gcc agc ggt tcc cag cat agc tac tgg aag gga    528
Gly Phe Asp Pro Gly Ala Ser Gly Ser Gln His Ser Tyr Trp Lys Gly
                165                 170                 175 ggc ccc act gtg gac ccc gag gag ctg ttc agg aag atc ttt ggc gag    576
Gly Pro Thr Val Asp Pro Glu Glu Leu Phe Arg Lys Ile Phe Gly Glu
```

```
                  180             185              190
ttc tca tcc tct tca ttt gga gat ttc cag acc gtg ttt gat cag cct    624
Phe Ser Ser Ser Phe Gly Asp Phe Gln Thr Val Phe Asp Gln Pro
        195                 200                 205 cag gaa tac ttc atg gag ttg aca ttc aat caa gct gca aag ggg gtc    672
Gln Glu Tyr Phe Met Glu Leu Thr Phe Asn Gln Ala Ala Lys Gly Val
    210                 215                 220 aac aag gag ttc acc gtg aac atc atg gac acg tgt gag cgc tgc aac    720
Asn Lys Glu Phe Thr Val Asn Ile Met Asp Thr Cys Glu Arg Cys Asn
225                 230                 235                 240 ggc aag ggg aac gag ccc ggc acc aag gtg cag cat tgc cac tac tgt    768
Gly Lys Gly Asn Glu Pro Gly Thr Lys Val Gln His Cys His Tyr Cys
                245                 250                 255 ggc ggc tcc ggc atg gaa acc atc aac aca ggc cct ttt gtg atg cgt    816
Gly Gly Ser Gly Met Glu Thr Ile Asn Thr Gly Pro Phe Val Met Arg
            260                 265                 270 tcc acg tgt agg aga tgt ggt ggc cgc ggc tcc atc atc ata tcg ccc    864
Ser Thr Cys Arg Arg Cys Gly Gly Arg Gly Ser Ile Ile Ile Ser Pro
        275                 280                 285 tgt gtg gtc tgc agg gga gca gga caa gcc aag cag aaa aag cga gtg    912
Cys Val Val Cys Arg Gly Ala Gly Gln Ala Lys Gln Lys Lys Arg Val
    290                 295                 300 atg atc cct gtg cct gca gga gtc gag gat ggc cag acc gtg agg atg    960
Met Ile Pro Val Pro Ala Gly Val Glu Asp Gly Gln Thr Val Arg Met
305                 310                 315                 320 cct gtg gga aaa agg gaa att ttc att acg ttc agg gtg cag aaa agc   1008
Pro Val Gly Lys Arg Glu Ile Phe Ile Thr Phe Arg Val Gln Lys Ser
                325                 330                 335 cct gtg ttc cgg agg gac ggc gca gac atc cac tcc gac ctc ttt att   1056
Pro Val Phe Arg Arg Asp Gly Ala Asp Ile His Ser Asp Leu Phe Ile
            340                 345                 350 tct ata gct cag gct ctt ctt ggg gga aca gcc aga gcc cag ggc ctg   1104
Ser Ile Ala Gln Ala Leu Leu Gly Gly Thr Ala Arg Ala Gln Gly Leu
        355                 360                 365 tac gag acg atc aac gtg acg atc ccc cct ggg act cag aca gac cag   1152
Tyr Glu Thr Ile Asn Val Thr Ile Pro Pro Gly Thr Gln Thr Asp Gln
    370                 375                 380 aag att cgg atg ggt ggg aaa ggc atc ccc cgg att aac agc tac ggc   1200
Lys Ile Arg Met Gly Gly Lys Gly Ile Pro Arg Ile Asn Ser Tyr Gly
385                 390                 395                 400 tac gga gac cac tac atc cac atc aag ata cga gtt cca aag agg cta   1248
Tyr Gly Asp His Tyr Ile His Ile Lys Ile Arg Val Pro Lys Arg Leu
                405                 410                 415 acg agc cgg cag cag agc ctg atc ctg agc tac gcc gag gac gag aca   1296
Thr Ser Arg Gln Gln Ser Leu Ile Leu Ser Tyr Ala Glu Asp Glu Thr
            420                 425                 430 gat gtg gag ggg acg gtg aac ggc gtc acc ctc acc agc tct ggt ggc   1344
Asp Val Glu Gly Thr Val Asn Gly Val Thr Leu Thr Ser Ser Gly Gly
        435                 440                 445 agc acc atg gat agc tcc gca gga agc aag gct agg cgt gag gct ggg   1392
Ser Thr Met Asp Ser Ser Ala Gly Ser Lys Ala Arg Arg Glu Ala Gly
    450                 455                 460 gag gac gag gag gga ttc ctt tcc aaa ctt aag aaa atg ttt acc tca   1440
Glu Asp Glu Glu Gly Phe Leu Ser Lys Leu Lys Lys Met Phe Thr Ser
465                 470                 475                 480 tga                                                                1443

<210> SEQ ID NO 3
<211> LENGTH: 1362
```

<212> TYPE: DNA
<213> ORGANISM: Homo sapiens
<220> FEATURE:
<221> NAME/KEY: CDS
<222> LOCATION: (1)..(1359)

<400> SEQUENCE: 3

```
atg gct gcg cgg tgc tcc aca cgc tgg ttg ctg gtg gtt gtg ggg acc      48
Met Ala Ala Arg Cys Ser Thr Arg Trp Leu Leu Val Val Val Gly Thr
 1               5                  10                  15 ccg cgg ctg ccg gct ata tcg ggt aga ggg gcc cgg ccg ccc agg gag      96
Pro Arg Leu Pro Ala Ile Ser Gly Arg Gly Ala Arg Pro Pro Arg Glu
             20                  25                  30 ggc gtg gtg ggg gca tgg ctg agc cgc aag ctg agc gtc ccc gcc ttt     144
Gly Val Val Gly Ala Trp Leu Ser Arg Lys Leu Ser Val Pro Ala Phe
         35                  40                  45 gcg tct tcc ctg acc tct tgc ggc ccc cga gcg ctg ctg aca ttg aga     192
Ala Ser Ser Leu Thr Ser Cys Gly Pro Arg Ala Leu Leu Thr Leu Arg
     50                  55                  60 cct ggt gtc agc ctt aca gga aca aaa cat aac cct ttc att tgt act     240
Pro Gly Val Ser Leu Thr Gly Thr Lys His Asn Pro Phe Ile Cys Thr
 65                  70                  75                  80 gcc tcc ttc cac acg agt gcc cct ttg gcc aaa gaa gat tat tat cag     288
Ala Ser Phe His Thr Ser Ala Pro Leu Ala Lys Glu Asp Tyr Tyr Gln
                 85                  90                  95 ata tta gga gtg cct cga aat gcc agc cag aaa gag atc aag aaa gcc     336
Ile Leu Gly Val Pro Arg Asn Ala Ser Gln Lys Glu Ile Lys Lys Ala
            100                 105                 110 tat tat cag ctt gcc aag aag tat cac cct gac aca aat aag gat gat     384
Tyr Tyr Gln Leu Ala Lys Lys Tyr His Pro Asp Thr Asn Lys Asp Asp
        115                 120                 125 ccc aaa gcc aag gag aag ttc tcc cag ctg gca gaa gcc tat gag gtt     432
Pro Lys Ala Lys Glu Lys Phe Ser Gln Leu Ala Glu Ala Tyr Glu Val
    130                 135                 140 ttg agt gat gag gtg aag agg aag cag tac gat gcc tac ggc tct gca     480
Leu Ser Asp Glu Val Lys Arg Lys Gln Tyr Asp Ala Tyr Gly Ser Ala
145                 150                 155                 160 ggc ttc gat cct ggg gcc agc ggc tcc cag cat agc tac tgg aag gga     528
Gly Phe Asp Pro Gly Ala Ser Gly Ser Gln His Ser Tyr Trp Lys Gly
                165                 170                 175 ggc ccc act gtg gac ccc gag gag ctg ttc agg aag atc ttt ggc gag     576
Gly Pro Thr Val Asp Pro Glu Glu Leu Phe Arg Lys Ile Phe Gly Glu
            180                 185                 190 ttc tca tcc tct tca ttt gga gat ttc cag acc gtg ttt gat cag cct     624
Phe Ser Ser Ser Ser Phe Gly Asp Phe Gln Thr Val Phe Asp Gln Pro
        195                 200                 205 cag gaa tac ttc atg gag ttg aca ttc aat caa gct gca aag ggg gtc     672
Gln Glu Tyr Phe Met Glu Leu Thr Phe Asn Gln Ala Ala Lys Gly Val
    210                 215                 220 aac aag gag ttc acc gtg aac atc atg gac acg tgt gag cgc tgc aac     720
Asn Lys Glu Phe Thr Val Asn Ile Met Asp Thr Cys Glu Arg Cys Asn
225                 230                 235                 240 ggc aag ggg aac gag ccc ggc acc aag gtg cag cat tgc cac tac tgt     768
Gly Lys Gly Asn Glu Pro Gly Thr Lys Val Gln His Cys His Tyr Cys
                245                 250                 255 ggc ggc tcc ggc atg gaa acc atc aac aca ggc cct ttt gtg atg cgt     816
Gly Gly Ser Gly Met Glu Thr Ile Asn Thr Gly Pro Phe Val Met Arg
            260                 265                 270 tcc acg tgt agg aga tgt ggt ggc cgc ggc tcc atc atc ata tcg ccc     864
Ser Thr Cys Arg Arg Cys Gly Gly Arg Gly Ser Ile Ile Ile Ser Pro
        275                 280                 285
```

-continued

| | | |
|---|---|---|
| tgt gtg gtc tgc agg gga gca gga caa gcc aag cag aaa aag cga gtg<br>Cys Val Val Cys Arg Gly Ala Gly Gln Ala Lys Gln Lys Lys Arg Val<br>290                         295                       300 | | 912 |
| atg atc cct gtg cct gca gga gtc gag gat ggc cag acc gtg agg atg<br>Met Ile Pro Val Pro Ala Gly Val Glu Asp Gly Gln Thr Val Arg Met<br>305                      310                      315                   320 | | 960 |
| cct gtg gga aaa agg gaa att ttc att acg ttc agg gtg cag aaa agc<br>Pro Val Gly Lys Arg Glu Ile Phe Ile Thr Phe Arg Val Gln Lys Ser<br>                    325                       330                   335 | | 1008 |
| cct gtg ttc cgg agg gac ggc gca gac atc cac tcc gac ctc ttt att<br>Pro Val Phe Arg Arg Asp Gly Ala Asp Ile His Ser Asp Leu Phe Ile<br>              340                       345                       350 | | 1056 |
| tct ata gct cag gct ctt ctt ggg gga aca gcc aga gcc cag ggc ctg<br>Ser Ile Ala Gln Ala Leu Leu Gly Gly Thr Ala Arg Ala Gln Gly Leu<br>355                         360                       365 | | 1104 |
| tac gag acg atc aac gtg acg atc ccc cct ggg act cag aca gac cag<br>Tyr Glu Thr Ile Asn Val Thr Ile Pro Pro Gly Thr Gln Thr Asp Gln<br>370                         375                       380 | | 1152 |
| aag att cgg atg ggt ggg aaa ggc atc ccc cgg att aac agc tac ggc<br>Lys Ile Arg Met Gly Gly Lys Gly Ile Pro Arg Ile Asn Ser Tyr Gly<br>385                         390                       395                   400 | | 1200 |
| tac gga gac cac tac atc cac atc aag ata cga gtt cca aag agg cta<br>Tyr Gly Asp His Tyr Ile His Ile Lys Ile Arg Val Pro Lys Arg Leu<br>                          405                       410                       415 | | 1248 |
| acg agc cgg cag cag agc ctg atc ctg agc tac gcc gag gac gag aca<br>Thr Ser Arg Gln Gln Ser Leu Ile Leu Ser Tyr Ala Glu Asp Glu Thr<br>                    420                       425                   430 | | 1296 |
| gat gtg gag ggg acg gtg aac ggc gtc acc ctc acc agc tct gga aaa<br>Asp Val Glu Gly Thr Val Asn Gly Val Thr Leu Thr Ser Ser Gly Lys<br>              435                       440                       445 | | 1344 |
| aga tcc act gga aac tag<br>Arg Ser Thr Gly Asn<br>    450 | | 1362 |

<210> SEQ ID NO 4
<211> LENGTH: 1242
<212> TYPE: DNA
<213> ORGANISM: Homo sapiens

<400> SEQUENCE: 4

| | |
|---|---|
| gtcagcctta caggaacaaa acataaccct ttcatttgta ctgcctcctt ccacacgagt | 60 |
| gccccttggg ccaaagaaga ttattatcag atattaggag tgcctcgaaa tgccagccag | 120 |
| aaagagatca agaaagccta ttatcagctt gccaagaagt atcaccctga cacaaataag | 180 |
| gatgatccca agccaagga gaagttctcc cagctggcag aagcctatga ggttttgagt | 240 |
| gatgaggtga agaggaagca gtacgatgcc tacggctctg caggcttcga tcctggggcc | 300 |
| agcggctccc agcatagcta ctggaaggga ggccccactg tgaccccga ggagctgttc | 360 |
| aggaagatct ttgcgagtt ctcatcctct tcatttggag atttccagac cgtgtttgat | 420 |
| cagcctcagg aatacttcat ggagttgaca ttcaatcaag ctgcaaaggg ggtcaacaag | 480 |
| gagttcaccg tgaacatcat ggacacgtgt gagcgctgca acggcaaggg gaacgagccc | 540 |
| ggcaccaagg tgcagcattg ccactactgt ggcggctccg gcatggaaac catcaacaca | 600 |
| ggccctttg tgatgcgttc cacgtgtagg agatgtggtg gccgcggctc catcatcata | 660 |
| tcgccctgtg tggtctgcag gggagcagga caagccaagc agaaaaagcg agtgatgatc | 720 |
| cctgtgcctg caggagtcga ggatggccag accgtgagga tgcctgtggg aaaagggaa | 780 |

```
atttcatta cgttcagggt gcagaaaagc cctgtgttcc ggagggacgg cgcagacatc        840
cactccgacc tctttatttc tatagctcag gctcttcttg ggggaacagc cagagcccag        900
ggcctgtacg agacgatcaa cgtgacgatc ccccctggga ctcagacaga ccagaagatt        960
cggatgggtg ggaaaggcat ccccggatt aacagctacg gctacggaga ccactacatc        1020
cacatcaaga tacgagttcc aaagaggcta acgagccggc agcagagcct gatcctgagc        1080
tacgccgagg acgagacaga tgtggagggg acggtgaacg gcgtcaccct caccagctct        1140
ggtggcagca ccatggatag ctccgcagga agcaaggcta ggcgtgaggc tggggaggac        1200
gaggagggat tcctttccaa acttaagaaa atgtttacct ca        1242
```

<210> SEQ ID NO 5
<211> LENGTH: 1161
<212> TYPE: DNA
<213> ORGANISM: Homo sapiens

<400> SEQUENCE: 5

```
gtcagcctta caggaacaaa acataaccct ttcatttgta ctgcctcctt ccacacgagt        60 gccccttttgg ccaaagaaga ttattatcag atattaggag tgcctcgaaa tgccagccag        120
aaagagatca agaaagccta ttatcagctt gccaagaagt atcaccctga cacaaataag        180
gatgatccca agccaagga gaagttctcc cagctggcag aagcctatga ggttttgagt        240
gatgaggtga agaggaagca gtacgatgcc tacggctctg caggcttcga tcctggggcc        300
agcggctccc agcatagcta ctggaaggga ggccccactg tggaccccga ggagctgttc        360
aggaagatct ttggcgagtt ctcatcctct tcatttggag atttccagac cgtgttttgat        420 cagcctcagg aatacttcat ggagttgaca ttcaatcaag ctgcaaaggg ggtcaacaag        480
gagttcaccg tgaacatcat ggacacgtgt gagcgctgca acggcaaggg gaacgagccc        540
ggcaccaagg tgcagcattg ccactactgt ggcggctccg gcatggaaac catcaacaca        600
ggcccttttg tgatgcgttc cacgtgtagg agatgtggtg gccgcggctc catcatcata        660
tcgccctgtg tggtctgcag gggagcagga caagccaagc agaaaaagcg agtgatgatc        720
cctgtgcctg caggagtcga ggatggccag accgtgagga tgcctgtggg aaaaagggaa        780 atttcatta cgttcagggt gcagaaaagc cctgtgttcc ggagggacgg cgcagacatc        840
cactccgacc tctttatttc tatagctcag gctcttcttg ggggaacagc cagagcccag        900
ggcctgtacg agacgatcaa cgtgacgatc ccccctggga ctcagacaga ccagaagatt        960
cggatgggtg ggaaaggcat ccccggatt aacagctacg gctacggaga ccactacatc        1020
cacatcaaga tacgagttcc aaagaggcta acgagccggc agcagagcct gatcctgagc        1080
tacgccgagg acgagacaga tgtggagggg acggtgaacg gcgtcaccct caccagctct        1140
ggaaaaagat ccactggaaa c        1161
```

<210> SEQ ID NO 6
<211> LENGTH: 99
<212> TYPE: DNA
<213> ORGANISM: Homo sapiens

<400> SEQUENCE: 6

```
ggcagcacca tggatagctc cgcaggaagc aaggctaggc gtgaggctgg ggaggacgag        60
gagggattcc tttccaaact taagaaaatg tttacctca        99
```

<210> SEQ ID NO 7
<211> LENGTH: 18

```
<212> TYPE: DNA
<213> ORGANISM: Homo sapiens

<400> SEQUENCE: 7
aaaagatcca ctggaaac                                                  18

<210> SEQ ID NO 8
<211> LENGTH: 480
<212> TYPE: PRT
<213> ORGANISM: Homo sapiens

<400> SEQUENCE: 8
```

Met Ala Ala Arg Cys Ser Thr Arg Trp Leu Val Val Gly Thr
 1               5                  10                  15

Pro Arg Leu Pro Ala Ile Ser Gly Arg Gly Ala Arg Pro Arg Glu
             20                  25                  30

Gly Val Val Gly Ala Trp Leu Ser Arg Lys Leu Ser Val Pro Ala Phe
             35                  40                  45

Ala Ser Ser Leu Thr Ser Cys Gly Pro Arg Ala Leu Leu Thr Leu Arg
         50                  55                  60

Pro Gly Val Ser Leu Thr Gly Thr Lys His Asn Pro Phe Ile Cys Thr
 65                  70                  75                  80

Ala Ser Phe His Thr Ser Ala Pro Leu Ala Lys Glu Asp Tyr Tyr Gln
                 85                  90                  95

Ile Leu Gly Val Pro Arg Asn Ala Ser Gln Lys Glu Ile Lys Lys Ala
            100                 105                 110

Tyr Tyr Gln Leu Ala Lys Lys Tyr His Pro Asp Thr Asn Lys Asp Asp
        115                 120                 125

Pro Lys Ala Lys Glu Lys Phe Ser Gln Leu Ala Glu Ala Tyr Glu Val
    130                 135                 140

Leu Ser Asp Glu Val Lys Arg Lys Gln Tyr Asp Ala Tyr Gly Ser Ala
145                 150                 155                 160

Gly Phe Asp Pro Gly Ala Ser Gly Ser Gln His Ser Tyr Trp Lys Gly
                165                 170                 175

Gly Pro Thr Val Asp Pro Glu Glu Leu Phe Arg Lys Ile Phe Gly Glu
            180                 185                 190

Phe Ser Ser Ser Phe Gly Asp Phe Gln Thr Val Phe Asp Gln Pro
        195                 200                 205

Gln Glu Tyr Phe Met Glu Leu Thr Phe Asn Gln Ala Ala Lys Gly Val
    210                 215                 220

Asn Lys Glu Phe Thr Val Asn Ile Met Asp Thr Cys Glu Arg Cys Asn
225                 230                 235                 240

Gly Lys Gly Asn Glu Pro Gly Thr Lys Val Gln His Cys His Tyr Cys
                245                 250                 255

Gly Gly Ser Gly Met Glu Thr Ile Asn Thr Gly Pro Phe Val Met Arg
            260                 265                 270

Ser Thr Cys Arg Arg Cys Gly Gly Arg Gly Ser Ile Ile Ile Ser Pro
        275                 280                 285

Cys Val Val Cys Arg Gly Ala Gly Gln Ala Lys Gln Lys Lys Arg Val
    290                 295                 300

Met Ile Pro Val Pro Ala Gly Val Glu Asp Gly Gln Thr Val Arg Met
305                 310                 315                 320

Pro Val Gly Lys Arg Glu Ile Phe Ile Thr Phe Arg Val Gln Lys Ser
                325                 330                 335

Pro Val Phe Arg Arg Asp Gly Ala Asp Ile His Ser Asp Leu Phe Ile

-continued

```
                340                 345                 350
Ser Ile Ala Gln Ala Leu Leu Gly Gly Thr Ala Arg Ala Gln Gly Leu
                355                 360                 365

Tyr Glu Thr Ile Asn Val Thr Ile Pro Pro Gly Thr Gln Thr Asp Gln
    370                 375                 380

Lys Ile Arg Met Gly Gly Lys Gly Ile Pro Arg Ile Asn Ser Tyr Gly
385                 390                 395                 400

Tyr Gly Asp His Tyr Ile His Ile Lys Ile Arg Val Pro Lys Arg Leu
                405                 410                 415

Thr Ser Arg Gln Gln Ser Leu Ile Leu Ser Tyr Ala Glu Asp Glu Thr
                420                 425                 430

Asp Val Glu Gly Thr Val Asn Gly Val Thr Leu Thr Ser Ser Gly Gly
            435                 440                 445

Ser Thr Met Asp Ser Ser Ala Gly Ser Lys Ala Arg Arg Glu Ala Gly
            450                 455                 460

Glu Asp Glu Glu Gly Phe Leu Ser Lys Leu Lys Lys Met Phe Thr Ser
465                 470                 475                 480

<210> SEQ ID NO 9
<211> LENGTH: 453
<212> TYPE: PRT
<213> ORGANISM: Homo sapiens

<400> SEQUENCE: 9

Met Ala Ala Arg Cys Ser Thr Arg Trp Leu Leu Val Val Val Gly Thr
  1                 5                  10                  15

Pro Arg Leu Pro Ala Ile Ser Gly Arg Gly Ala Arg Pro Pro Arg Glu
                 20                  25                  30

Gly Val Val Gly Ala Trp Leu Ser Arg Lys Leu Ser Val Pro Ala Phe
             35                  40                  45

Ala Ser Ser Leu Thr Ser Cys Gly Pro Arg Ala Leu Leu Thr Leu Arg
         50                  55                  60

Pro Gly Val Ser Leu Thr Gly Thr Lys His Asn Pro Phe Ile Cys Thr
 65                  70                  75                  80

Ala Ser Phe His Thr Ser Ala Pro Leu Ala Lys Glu Asp Tyr Tyr Gln
                 85                  90                  95

Ile Leu Gly Val Pro Arg Asn Ala Ser Gln Lys Glu Ile Lys Lys Ala
                100                 105                 110

Tyr Tyr Gln Leu Ala Lys Lys Tyr His Pro Asp Thr Asn Lys Asp Asp
            115                 120                 125

Pro Lys Ala Lys Glu Lys Phe Ser Gln Leu Ala Glu Ala Tyr Glu Val
        130                 135                 140

Leu Ser Asp Glu Val Lys Arg Lys Gln Tyr Asp Ala Tyr Gly Ser Ala
145                 150                 155                 160

Gly Phe Asp Pro Gly Ala Ser Gly Ser Gln His Ser Tyr Trp Lys Gly
                165                 170                 175

Gly Pro Thr Val Asp Pro Glu Glu Leu Phe Arg Lys Ile Phe Gly Glu
            180                 185                 190

Phe Ser Ser Ser Ser Phe Gly Asp Phe Gln Thr Val Phe Asp Gln Pro
        195                 200                 205

Gln Glu Tyr Phe Met Glu Leu Thr Phe Asn Gln Ala Ala Lys Gly Val
    210                 215                 220

Asn Lys Glu Phe Thr Val Asn Ile Met Asp Thr Cys Glu Arg Cys Asn
225                 230                 235                 240
```

```
Gly Lys Gly Asn Glu Pro Gly Thr Lys Val Gln His Cys His Tyr Cys
                245                 250                 255
Gly Gly Ser Gly Met Glu Thr Ile Asn Thr Gly Pro Phe Val Met Arg
            260                 265                 270
Ser Thr Cys Arg Arg Cys Gly Arg Gly Ser Ile Ile Ile Ser Pro
        275                 280                 285
Cys Val Val Cys Arg Gly Ala Gly Gln Ala Lys Gln Lys Lys Arg Val
    290                 295                 300
Met Ile Pro Val Pro Ala Gly Val Glu Asp Gly Gln Thr Val Arg Met
305                 310                 315                 320
Pro Val Gly Lys Arg Glu Ile Phe Ile Thr Phe Arg Val Gln Lys Ser
                325                 330                 335
Pro Val Phe Arg Arg Asp Gly Ala Asp Ile His Ser Asp Leu Phe Ile
                340                 345                 350
Ser Ile Ala Gln Ala Leu Leu Gly Gly Thr Ala Arg Ala Gln Gly Leu
            355                 360                 365
Tyr Glu Thr Ile Asn Val Thr Ile Pro Pro Gly Thr Gln Thr Asp Gln
        370                 375                 380
Lys Ile Arg Met Gly Gly Lys Gly Ile Pro Arg Ile Asn Ser Tyr Gly
385                 390                 395                 400
Tyr Gly Asp His Tyr Ile His Ile Lys Ile Arg Val Pro Lys Arg Leu
                405                 410                 415
Thr Ser Arg Gln Gln Ser Leu Ile Leu Ser Tyr Ala Glu Asp Glu Thr
            420                 425                 430
Asp Val Glu Gly Thr Val Asn Gly Val Thr Leu Thr Ser Ser Gly Lys
        435                 440                 445
Arg Ser Thr Gly Asn
        450

<210> SEQ ID NO 10
<211> LENGTH: 414
<212> TYPE: PRT
<213> ORGANISM: Homo sapiens

<400> SEQUENCE: 10

Val Ser Leu Thr Gly Thr Lys His Asn Pro Phe Ile Cys Thr Ala Ser
  1               5                  10                  15
Phe His Thr Ser Ala Pro Leu Ala Lys Glu Asp Tyr Tyr Gln Ile Leu
             20                  25                  30
Gly Val Pro Arg Asn Ala Ser Gln Lys Glu Ile Lys Lys Ala Tyr Tyr
         35                  40                  45
Gln Leu Ala Lys Lys Tyr His Pro Asp Thr Asn Lys Asp Asp Pro Lys
     50                  55                  60
Ala Lys Glu Lys Phe Ser Gln Leu Ala Glu Ala Tyr Glu Val Leu Ser
65                   70                  75                  80
Asp Glu Val Lys Arg Lys Gln Tyr Asp Ala Tyr Gly Ser Ala Gly Phe
                 85                  90                  95
Asp Pro Gly Ala Ser Gly Ser Gln His Ser Tyr Trp Lys Gly Gly Pro
            100                 105                 110
Thr Val Asp Pro Glu Glu Leu Phe Arg Lys Ile Phe Gly Glu Phe Ser
        115                 120                 125
Ser Ser Ser Phe Gly Asp Phe Gln Thr Val Phe Asp Gln Pro Gln Glu
    130                 135                 140
Tyr Phe Met Glu Leu Thr Phe Asn Gln Ala Ala Lys Gly Val Asn Lys
145                 150                 155                 160
```

-continued

```
Glu Phe Thr Val Asn Ile Met Asp Thr Cys Glu Arg Cys Asn Gly Lys
                165                 170                 175

Gly Asn Glu Pro Gly Thr Lys Val Gln His Cys His Tyr Cys Gly Gly
            180                 185                 190

Ser Gly Met Glu Thr Ile Asn Thr Gly Pro Phe Val Met Arg Ser Thr
        195                 200                 205

Cys Arg Arg Cys Gly Gly Arg Gly Ser Ile Ile Ser Pro Cys Val
    210                 215                 220

Val Cys Arg Gly Ala Gly Gln Ala Lys Gln Lys Arg Val Met Ile
225                 230                 235                 240

Pro Val Pro Ala Gly Val Glu Asp Gly Gln Thr Val Arg Met Pro Val
                245                 250                 255

Gly Lys Arg Glu Ile Phe Ile Thr Phe Arg Val Gln Lys Ser Pro Val
            260                 265                 270

Phe Arg Arg Asp Gly Ala Asp Ile His Ser Asp Leu Phe Ile Ser Ile
        275                 280                 285

Ala Gln Ala Leu Leu Gly Gly Thr Ala Arg Ala Gln Gly Leu Tyr Glu
    290                 295                 300

Thr Ile Asn Val Thr Ile Pro Pro Gly Thr Gln Thr Asp Gln Lys Ile
305                 310                 315                 320

Arg Met Gly Gly Lys Gly Ile Pro Arg Ile Asn Ser Tyr Gly Tyr Gly
                325                 330                 335

Asp His Tyr Ile His Ile Lys Ile Arg Val Pro Lys Arg Leu Thr Ser
            340                 345                 350

Arg Gln Gln Ser Leu Ile Leu Ser Tyr Ala Glu Asp Glu Thr Asp Val
        355                 360                 365

Glu Gly Thr Val Asn Gly Val Thr Leu Thr Ser Ser Gly Gly Ser Thr
    370                 375                 380

Met Asp Ser Ser Ala Gly Ser Lys Ala Arg Arg Glu Ala Gly Glu Asp
385                 390                 395                 400

Glu Glu Gly Phe Leu Ser Lys Leu Lys Lys Met Phe Thr Ser
                405                 410

<210> SEQ ID NO 11
<211> LENGTH: 387
<212> TYPE: PRT
<213> ORGANISM: Homo sapiens

<400> SEQUENCE: 11

Val Ser Leu Thr Gly Thr Lys His Asn Pro Phe Ile Cys Thr Ala Ser
  1               5                  10                  15

Phe His Thr Ser Ala Pro Leu Ala Lys Glu Asp Tyr Tyr Gln Ile Leu
                 20                  25                  30

Gly Val Pro Arg Asn Ala Ser Gln Lys Glu Ile Lys Lys Ala Tyr Tyr
             35                  40                  45

Gln Leu Ala Lys Lys Tyr His Pro Asp Thr Asn Lys Asp Asp Pro Lys
         50                  55                  60

Ala Lys Glu Lys Phe Ser Gln Leu Ala Glu Ala Tyr Glu Val Leu Ser
 65                  70                  75                  80

Asp Glu Val Lys Arg Lys Gln Tyr Asp Ala Tyr Gly Ser Ala Gly Phe
                 85                  90                  95

Asp Pro Gly Ala Ser Gly Ser Gln His Ser Tyr Trp Lys Gly Gly Pro
            100                 105                 110

Thr Val Asp Pro Glu Glu Leu Phe Arg Lys Ile Phe Gly Glu Phe Ser
```

-continued

```
                115                 120                     125
Ser Ser Ser Phe Gly Asp Phe Gln Thr Val Phe Asp Gln Pro Gln Glu
        130                 135                 140

Tyr Phe Met Glu Leu Thr Phe Asn Gln Ala Ala Lys Gly Val Asn Lys
145                 150                 155                 160

Glu Phe Thr Val Asn Ile Met Asp Thr Cys Glu Arg Cys Asn Gly Lys
                165                 170                 175

Gly Asn Glu Pro Gly Thr Lys Val Gln His Cys His Tyr Cys Gly Gly
            180                 185                 190

Ser Gly Met Glu Thr Ile Asn Thr Gly Pro Phe Val Met Arg Ser Thr
        195                 200                 205

Cys Arg Arg Cys Gly Arg Gly Ser Ile Ile Ser Pro Cys Val
    210                 215                 220

Val Cys Arg Gly Ala Gly Gln Ala Lys Gln Lys Arg Val Met Ile
225                 230                 235                 240

Pro Val Pro Ala Gly Val Glu Asp Gly Gln Thr Val Arg Met Pro Val
                245                 250                 255

Gly Lys Arg Glu Ile Phe Ile Thr Phe Arg Val Gln Lys Ser Pro Val
            260                 265                 270

Phe Arg Arg Asp Gly Ala Asp Ile His Ser Asp Leu Phe Ile Ser Ile
        275                 280                 285

Ala Gln Ala Leu Leu Gly Gly Thr Ala Arg Ala Gln Gly Leu Tyr Glu
        290                 295                 300

Thr Ile Asn Val Thr Ile Pro Pro Gly Thr Gln Thr Asp Gln Lys Ile
305                 310                 315                 320

Arg Met Gly Gly Lys Gly Ile Pro Arg Ile Asn Ser Tyr Gly Tyr Gly
                325                 330                 335

Asp His Tyr Ile His Ile Lys Ile Arg Val Pro Lys Arg Leu Thr Ser
            340                 345                 350

Arg Gln Gln Ser Leu Ile Leu Ser Tyr Ala Glu Asp Glu Thr Asp Val
        355                 360                 365

Glu Gly Thr Val Asn Gly Val Thr Leu Thr Ser Ser Gly Lys Arg Ser
    370                 375                 380

Thr Gly Asn
385

<210> SEQ ID NO 12
<211> LENGTH: 480
<212> TYPE: PRT
<213> ORGANISM: Homo sapiens

<400> SEQUENCE: 12

Met Ala Ala Arg Cys Ser Thr Arg Trp Leu Val Val Val Gly Thr
1               5                   10                  15

Pro Arg Leu Pro Ala Ile Ser Gly Arg Gly Ala Arg Pro Arg Glu
            20                  25                  30

Gly Val Val Gly Ala Trp Leu Ser Arg Lys Leu Ser Val Pro Ala Phe
        35                  40                  45

Ala Ser Ser Leu Thr Ser Cys Gly Pro Arg Ala Leu Leu Thr Leu Arg
    50                  55                  60

Pro Gly Val Ser Leu Thr Gly Thr Lys His Asn Pro Phe Ile Cys Thr
65                  70                  75                  80

Ala Ser Phe His Thr Ser Ala Pro Leu Ala Lys Glu Asp Tyr Tyr Gln
                85                  90                  95
```

```
Ile Leu Gly Val Pro Arg Asn Ala Ser Gln Lys Glu Ile Lys Lys Ala
            100                 105                 110
Tyr Tyr Gln Leu Ala Lys Lys Tyr His Pro Asp Thr Asn Lys Asp Asp
        115                 120                 125
Pro Lys Ala Lys Glu Lys Phe Ser Gln Leu Ala Glu Ala Tyr Glu Val
    130                 135                 140
Leu Ser Asp Glu Val Lys Arg Lys Gln Tyr Asp Ala Tyr Gly Ser Ala
145                 150                 155                 160
Gly Phe Asp Pro Gly Ala Ser Gly Ser Gln His Ser Tyr Trp Lys Gly
                165                 170                 175
Gly Pro Thr Val Asp Pro Glu Glu Leu Phe Arg Lys Ile Phe Gly Glu
            180                 185                 190
Phe Ser Ser Ser Phe Gly Asp Phe Gln Thr Val Phe Asp Gln Pro
        195                 200                 205
Gln Glu Tyr Phe Met Glu Leu Thr Phe Asn Gln Ala Ala Lys Gly Val
    210                 215                 220
Asn Lys Glu Phe Thr Val Asn Ile Met Asp Thr Cys Glu Arg Cys Asn
225                 230                 235                 240
Gly Lys Gly Asn Glu Pro Gly Thr Lys Val Gln His Cys His Tyr Cys
                245                 250                 255
Gly Gly Ser Gly Met Glu Thr Ile Asn Thr Gly Pro Phe Val Met Arg
            260                 265                 270
Ser Thr Cys Arg Arg Cys Gly Gly Arg Gly Ser Ile Ile Ile Ser Pro
        275                 280                 285
Cys Val Val Cys Arg Gly Ala Gly Gln Ala Lys Gln Lys Lys Arg Val
    290                 295                 300
Met Ile Pro Val Pro Ala Gly Val Glu Asp Gly Gln Thr Val Arg Met
305                 310                 315                 320
Pro Val Gly Lys Arg Glu Ile Phe Ile Thr Phe Arg Val Gln Lys Ser
                325                 330                 335
Pro Val Phe Arg Arg Asp Gly Ala Asp Ile His Ser Asp Leu Phe Ile
            340                 345                 350
Ser Ile Ala Gln Ala Leu Leu Gly Gly Thr Ala Arg Ala Gln Gly Leu
        355                 360                 365
Tyr Glu Thr Ile Asn Val Thr Ile Pro Pro Gly Thr Gln Thr Asp Gln
    370                 375                 380
Lys Ile Arg Met Gly Gly Lys Gly Ile Pro Arg Ile Asn Ser Tyr Gly
385                 390                 395                 400
Tyr Gly Asp His Tyr Ile His Ile Lys Ile Arg Val Pro Lys Arg Leu
                405                 410                 415
Thr Ser Arg Gln Gln Ser Leu Ile Leu Ser Tyr Ala Glu Asp Glu Thr
            420                 425                 430
Asp Val Glu Gly Thr Val Asn Gly Val Thr Leu Thr Ser Ser Gly Gly
        435                 440                 445
Ser Thr Met Asp Ser Ser Ala Gly Ser Lys Ala Arg Arg Glu Ala Gly
    450                 455                 460
Glu Asp Glu Glu Gly Phe Leu Ser Lys Leu Lys Lys Met Phe Thr Ser
465                 470                 475                 480

<210> SEQ ID NO 13
<211> LENGTH: 33
<212> TYPE: PRT
<213> ORGANISM: Homo sapiens

<400> SEQUENCE: 13
```

```
Gly Ser Thr Met Asp Ser Ser Ala Gly Ser Lys Ala Arg Arg Glu Ala
 1               5                  10                  15

Gly Glu Asp Glu Glu Gly Phe Leu Ser Lys Leu Lys Lys Met Phe Thr
                20                  25                  30

Ser
```

<210> SEQ ID NO 14
<211> LENGTH: 6
<212> TYPE: PRT
<213> ORGANISM: Homo sapiens

<400> SEQUENCE: 14

```
Lys Arg Ser Thr Gly Asn
 1               5
```

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Cys Phe Ile Thr Lys Ala Leu Gly Ile Ser Tyr Gly Arg Lys Lys Arg
 1               5                  10                  15

Arg Gln Arg Arg Arg Pro Pro Gln Gly Ser
                20                  25
```

<210> SEQ ID NO 16
<211> LENGTH: 12
<212> TYPE: PRT
<213> ORGANISM: Unknown Organism
<220> FEATURE:
<223> OTHER INFORMATION: Description of Unknown Organism: EGF derived
      peptide

<400> SEQUENCE: 16

```
Cys Met His Ile Glu Ser Leu Asp Ser Tyr Thr Cys
 1               5                  10
```

<210> SEQ ID NO 17
<211> LENGTH: 12
<212> TYPE: PRT
<213> ORGANISM: Unknown Organism
<220> FEATURE:
<223> OTHER INFORMATION: Description of Unknown Organism: EGF derived
      peptide

<400> SEQUENCE: 17

```
Cys Met Tyr Ile Glu Ala Leu Asp Lys Tyr Ala Cys
 1               5                  10
```

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      internalizing peptide

<400> SEQUENCE: 18

```
Glu Ala Ala Leu Ala Glu Ala Leu Ala Glu Ala Leu Ala Glu Ala Leu
 1               5                  10                  15
```

```
Ala Glu Ala Leu Ala Glu Ala Leu Glu Ala Leu Ala Ala
            20                  25

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Illustrative
      peptide

<400> SEQUENCE: 19

Gly Asn Ala Ala Ala Ala Arg Arg
  1               5

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
cgagacagat gtggaggggga                                                      20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21
gaataattta aacacact                                                         18

<210> SEQ ID NO 22
<211> LENGTH: 36
<212> TYPE: PRT
<213> ORGANISM: Homo sapiens

<400> SEQUENCE: 22

Ser Ser Gly Gly Ser Thr Met Asp Ser Ser Ala Gly Ser Lys Ala Arg
  1               5                  10                  15

Arg Glu Ala Gly Glu Asp Glu Glu Gly Phe Leu Ser Lys Leu Lys Lys
             20                  25                  30

Met Phe Thr Ser
          35

<210> SEQ ID NO 23
<211> LENGTH: 9
<212> TYPE: PRT
<213> ORGANISM: Homo sapiens

<400> SEQUENCE: 23

Ser Ser Gly Lys Arg Ser Thr Gly Asn
  1               5

<210> SEQ ID NO 24
<211> LENGTH: 33
<212> TYPE: PRT
<213> ORGANISM: Homo sapiens

<400> SEQUENCE: 24

Gly Ser Thr Met Asp Ser Ser Ala Gly Ser Lys Ala Arg Arg Glu Ala
  1               5                  10                  15
```

```
Gly Glu Asp Glu Glu Gly Phe Leu Ser Lys Leu Lys Lys Met Phe Thr
            20                  25                  30

Ser

<210> SEQ ID NO 25
<211> LENGTH: 33
<212> TYPE: PRT
<213> ORGANISM: Mus sp.

<400> SEQUENCE: 25

Gly Arg Thr Met Asp Ser Ser Ala Glu Ser Lys Asp Arg Arg Glu Ala
 1               5                  10                  15

Gly Glu Asp Asn Glu Gly Phe Leu Ser Lys Leu Lys Lys Ile Phe Thr
            20                  25                  30

Ser

<210> SEQ ID NO 26
<211> LENGTH: 6
<212> TYPE: PRT
<213> ORGANISM: Homo sapiens

<400> SEQUENCE: 26

Lys Arg Ser Thr Gly Asn
 1               5

<210> SEQ ID NO 27
<211> LENGTH: 6
<212> TYPE: PRT
<213> ORGANISM: Mus sp.

<400> SEQUENCE: 27

Lys Arg Ser Thr Gly Asn
 1               5
```

METHODS AND REAGENTS TO REGULATE APOPTOSIS

CROSS-REFERENCE TO RELATED APPLICATIONS

This application claims the benefit of U.S. Provisional Application No. 60/219,718, filed Jul. 19, 2000 and U.S. Provisional Application No. 60/219,537, filed Jul. 20, 2000, the contents of which are specifically incorporated herein by reference.

BACKGROUND OF THE INVENTION

The term apoptosis first appeared in the biomedical literature to delineate a structurally distinctive mode of cell death. The cardinal morphological features are cell shrinkage, accompanied by bubbling and blebbing from the surface, and culminating in separation of the cell into a cluster of membrane-bounded bodies. Organellar structure is usually preserved intact, but the nucleus undergoes a characteristic condensation of chromatin, initiated at sublamellar foci and often extending to generate toroidal or caplike, densely heterochromatic regions. Changes in several cell surface molecules also ensure that, in tissues, apoptotic cells are immediately recognized and phagocytosed by their neighbors. The result is that many cells can be deleted from tissues in a relatively short time with little to show for it in conventional microscopic sections.

This process is responsible for cell death in development, normal tissue turnover, atrophy induced by endocrine and other stimuli, negative selection in the immune system, and a substantial proportion of T-cell killing. It also accounts for many cell deaths following exposure to cytotoxic compounds, hypoxia or viral infection. It is a major factor in the cell kinetics of tumors, both growing and regressing. Many cancer therapeutic agents exert their effects through initiation of apoptosis, and even the process of carcinogenesis itself seems sometimes to depend upon a selective, critical failure of apoptosis that permits the survival of cells after mutagenic DNA damage. Apoptosis probably contributes to many chronic degenerative processes, including Alzheimer's disease, Parkinson's disease and heart failure.

Programmed cell death serves as a major mechanism for the precise regulation of cell numbers and as a defense mechanism to remove unwanted and potentially dangerous cells. Despite the heterogeneity of cell death induction pathways, the execution of the death program is often associated with characteristic morphological and biochemical changes, and this form of programmed cell death has been termed apoptosis. Key elements of the apoptotic pathway include:

Death receptors: Apoptosis has been found to be induced via the stimulation of several different cell surface receptors in association with caspase activation. For example, the CD95 (APO-1, Fas) receptor ligand system is a critical mediator of several physiological and pathophysiological processes, including homeostasis of the peripheral lymphoid compartment and CTL-mediated target cell killing. Upon cross-linking by ligand or agonist antibody, the Fas receptor initiates a signal transduction cascade which leads to caspase-dependent programmed cell death.

Membrane alterations: In the early stages of apoptosis, changes occur at the cell surface and plasma membrane. One of these plasma membrane alterations is the translocation of phosphatidylserine (PS) from the inner side of the plasma membrane to the outer layer, by which PS becomes exposed at the external surface of the cell.

Protease cascade: Signals leading to the activation of a family of intracellular cysteine proteases, the caspases, (Cysteinyl-aspartate-specific proteinases) play a pivotal role in the initiation and execution of apoptosis induced by various stimuli. At least 11 different members of caspases in mammalian cells have been identified. Among the best-characterized caspases is caspase-1 or ICE (Interleukin-1b-Converting Enzyme), which was originally identified as a cysteine protease responsible for processing of interleukin Mitochondrial changes: Mitochondrial physiology is disrupted in cells undergoing either apoptosis or necrosis. During apoptosis mitochondrial permeability is altered and apoptosis specific protease activators are released from mitochondria. Specifically, the discontinuity of the outer mitochondrial membrane results in the redistribution of cytochrome C to the cytosol followed by subsequent depolarization of the inner mitochondrial membrane. Cytochrome C (Apaf-2) release further promotes caspase activation by binding to Apaf-1 and therefore activating Apaf-3 (caspase 9). AIF (apoptosis inducing factor), released in the cytoplasm, has proteolytic activity and is by itself sufficient to induce apoptosis.

DNA fragmentation: The biochemical hallmark of apoptosis is the fragmentation of the genomic DNA, an irreversible event that commits the cell to die and occurs before changes in plasma membrane permeability (prelytic DNA fragmentation). In many systems, this DNA fragmentation has been shown to result from activation of an endogenous $Ca^{2+}$ and $Mg^{2+}$-dependent nuclear endonuclease. This enzyme selectively cleaves DNA at sites located between nucleosomal units (linker DNA) generating mono- and oligonucleosomal DNA fragments.

Genetic studies in Caenorhabditis elegans had led to the identification of cell death genes (ced). The genes ced-3 and ced-4 are essential for cell death; ced-9 antagonizes the activities of ced-3 and ced-4, and thereby protects cells that should survive from any accidental activation of the death program. Caspases (cysteine aspartases) are the mammalian homologues of CED-3. CED-9 protein is homologous to a family of many members termed the Bcl-2 family (Bcl-2s) in reference to the first discovered mammalian cell death regulator. In both worm and mammalian cells, the anti-apoptotic members of the Bcl-2 family act upstream of the execution caspases somehow preventing their proteolytic processing into active killers.

Caspases appear to be present in most if not all cells in inactive proenzyme form, awaiting activation by cleavage. One of the killing mechanisms of cytotoxic T cells is a protease, granzyme B, that is delivered to the target cell by the T cell granules and triggers these latent proenzymes. There are endogenous triggers also, and the first to be discovered—the *C. elegans* CED4 protein and its mammalian homologue—is particularly intriguing because of its mitochondrial origin. Thus CED4 could be the signal that initiates apoptosis under conditions of shutdown of cellular energy metabolism, or when there is a critical level of cell injury affecting mitochondrial respiration. In this way CED4 may act as the link between agents long known to be associated with mitochondrial injury, such as calcium and reactive oxygen species, and the initiation of apoptosis.

A second mitochondrial protein of enormous significance in apoptosis is BCL2, a mammalian homologue of the nematode CED9 protein. BCL2 has the tertiary structure of a bacterial pore-forming protein, and inserts into the outer membrane of mitochondria. Two main mechanisms of action have been proposed to connect Bcl-2s to caspases. In the first one, anti-apoptotic Bcl-2s would maintain cell survival by dragging caspases to intracellular membranes (probably the mitochondrial membrane) and by preventing their activation. The recently described mammalian protein Apaf-1 (apoptosis protease-activating factor 1) could be the mammalian equivalent of CED-4 and could be the physical link between Bcl-2s and caspases. In the second one, Bcl-2 would act by regulating the release from mitochondria of some caspases activators: cytochrome c and/or AIF (apoptosis-inducing factor). This crucial position of mitochondria in programmed cell death control is reinforced by the observation that mitochondria contribute to apoptosis signaling via the production of reactive oxygen species. Although for a long time the absence of mitochondrial changes was considered as a hallmark of apoptosis, mitochondria appear today as the central executioner of programmed cell death.

There are other sources of death transducers, e.g., which activate the caspase cascade because of injury to or signals arising in other parts of the cell than mitochondria. For instance, the onco-suppressor protein p53 is activated following some types of DNA damage and can trigger apoptosis. One way—but only one of several—whereby this happens is through transcriptional activation of BAX7. The second messenger ceramide, a product of membrane-linked acid sphingomyelinase activation, may act as a signal for plasma membrane damage. And a powerful caspase-activating system is mediated by cytokine receptors of the tumor necrosis factor family, notably fas/apo1/CD95, TNF receptor I, and others. These receptors, on receiving a death stimulus from binding their ligand, initiate a series of protein-protein interactions, building a complex (the death initiating signaling complex or DISC) which eventually recruits and activates caspase.

Apoptosis plays an important role in the homeostasis and development of all tissues within an organism. In contrast to necrosis (cell death by accident), apoptosis is a well regulated physiological process. Any disturbance of the balance between cell proliferation and cell death maintained by apoptosis can result in serious disease, in particular cancer.

There is a need in the art for methods for the identification and analysis of compounds and biological factors which modulate apoptosis, such as those which can increase the rate of apoptosis, as well as compounds and biological factors which interfere with the induction of apoptosis, e.g., in Th cells.

SUMMARY OF THE INVENTION

Here, we report that TID1 encodes two mitochondrial matrix localized splice variants of 43 and 40 kDa, which we have named hTid-$1_L$ and hTid-$1_S$, respectively. Both hTid-$1_L$ and hTid-$1_S$ retain their respective J domains and coimmunoprecipitate with mitochondrial Hsp70(mtHsp70). Expression of these proteins does not induce apoptosis, but surprisingly, expression of each of the two splice variants has opposing effects on a cell's ability to respond to an exogenous apoptotic stimulus. hTid-$1_L$ expression increases apoptosis triggered by both tumor necrosis factor (TNF) and the DNA-damaging agent mitomycin c (MMC). A J domain mutant of hTid-$1_L$ is able to suppress apoptosis to levels well below control cells. In sharp contrast, hTid-$1_S$ is able to suppress apoptosis, and a J domain mutant of hTid-$1_S$ increases apoptosis. Expression of hTid-$1_L$ and hTid-$1_S$ affect cytochrome c release from the mitochondria and caspase 3 activation, both of which are downstream of the mitochondria in TNF signaling. However, hTid-$1_L$ and hTid-$1_S$ do not affect the rate of caspase 8 activation, which is upstream of the mitochondria. Hence, hTid-$1_L$ and hTid-$1_S$ are two mitochondrial matrix-localized proteins that can regulate apoptotic signal transduction and may comprise a mechanism by which the mitochondria amplify or dampen apoptotic signals.

We have found that mTid-$1_S$, the murine homolog of the anti-apoptotic human TID1 encoded splice variant, hTid-$1_S$, is specifically upregulated in Th2 cells upon activation induced with either anti-CD3ε antibodies, or with PMA/ionomycin treatment. No upregulation is observed in Th1 cells upon activation. When a dominant negative mutant of hTid-$1_S$ is introduced into Th2 cells, these cells grow normally, but lose much of their resistance to AICD, and exhibit dramatically increased caspase 3 activity in response to anti-CD3ε stimulation. Thus, activation-induced accumulation of hTid-$1_S$ contributes to resistance to AICD of Th2 cells.

Accordingly, in certain embodiment, the present invention specifically contemplates the use of agents which alter the ratio of Tid-1L to Tid-1S and/or selectively inhibit the activity of one of the splicing isoforms in order to sensitize or desensitize a cell to an apoptotic signal. For instance, compounds which inhibit the formation or activity of the Tid-1L form may be useful in desensitizing cells to apoptotic signals. Such agents may be useful in promoting the survival of tissue subject to degeneration, e.g., such agents may be protective against neurodegenerative disorders. Conversely, agents which selectively inhibit formation or activity of the Tid-1S form may be useful in sensitizing cells to apoptotic signals. Such agents may be useful in conjunction with chemotherapeutics or to enhance the body's own ability to kill, e.g., virally infected cells or cancer cells.

BRIEF DESCRIPTION OF THE FIGURES

FIG. 3C. Fluorescence micrographs of Hoechst-stained U2OS cells that inducibly express the indicated protein after 24-hour treatment with 60 μM MMC. Apoptotic cells display condensed and fragmented chromatin.

FIG. 5 shows the nucleotide sequence encoding the long (SEQ ID NO: 2) and the short form (SEQ ID NO: 3) of the human Tid1 protein.

FIG. 7F. Analysis of mTid-1 protein expression upon activation of the murine Th1 cell lines 7A5 and D1.1 and the Th2 lines HAE 4A6 and CDC 35 with cells with anti-CD3ε antibody for 24 hours. Actin blots as loading controls and quantitations are shown underneath.

FIG. 10 shows the amino acid sequences of the mouse Tid-1L (SEQ ID NO: 28) and Tid-1S (SEQ ID NO: 29) proteins. "Xs" represent unknown amino acids.

DETAILED DESCRIPTION OF THE INVENTION

Figure 1A:
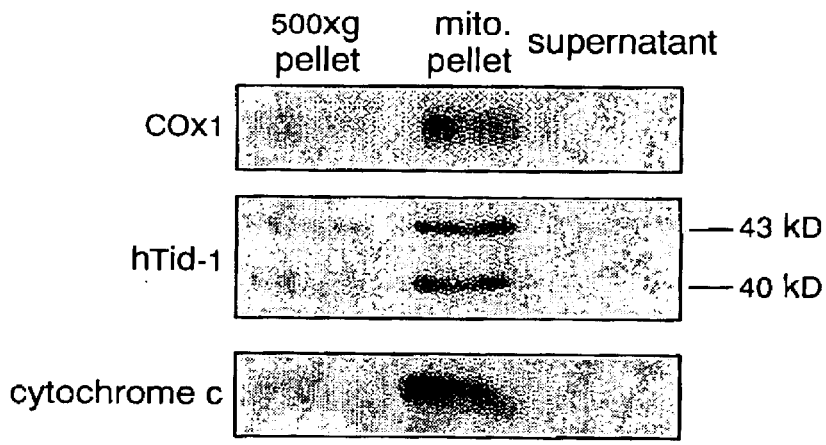
FIG. 1A. TID1 encodes two mitochondrial localized proteins, hTid-$1_L$ and hTid-$1_S$. SAOS-2 cells were homogenized, and nuclei were pelleted at 500×g. Mitochondria were pelleted at 10,000×g. Supernatant, 500×g pellet, and 10,000×g pellet were analyzed by immunoblot for the presence of COx1, hTid-1, and cytochrome c.

The invention provides isolated nucleic acids and encoded polypeptides which play a role in modulation of apoptosis, as well as diagnostic and therapeutic methods.

(i) Overview

The Drosophila l(2)tid gene has been classified as a tumor suppressor and encodes Tid56, a 56-kDa protein that is processed to a 50-kDa mitochondrial localized protein. (Kurzik-Dumke, U. et al. (1995) *Dev. Genet.* 16:64–76; Kurzik-Dumke, U. et al. (1997) in *Guidebook to Molecular*

Chaperones and Protein-Folding Catalysts, ed. Gething, M. J. (Oxford Univ. Press, Oxford), 117–121; Kurzik-Dumke, U. et al. (1998) Cell Stress Chaperones 3:12–27). Null mutants of Tid56 exhibit a lethal phenotype in which cells of the imaginal discs fail to differentiate and grow into lethal tumors. TID1 encodes two differentially spliced proteins, hTid-1S and hTid-1L, with strong homology to Tid56. (Schilling, B. et al. (1998) Virology 247:74–85).

hTid-1 and Tid56 are members of the DnaJ family of proteins. DnaJ proteins act as cochaperones and specificity factors for DnaK proteins and their eukaryotic homologs, the Hsp70 family. (Bukau, B. et al. (1998) Cell 92:351–366; Caplan, A. J. et al. (1993) Mol. Biol. Cell 4:555–563; Cyr, D. et al. (1994) Trends Biochem. Sci. 19:176–181; Misselwitz, B. et al. (1998) Mol. Cell 2:593–603). This protein family is characterized by a J domain, a highly conserved tetrahelical domain that binds to Hsp70 chaperones and activates their ATPase activity. The canonical J domain protein, DnaJ, was cloned from Escherichia coli as a mutant that cannot support the replication of bacteriophage. (Bardwell, J. C. et al. (1986) J. Biol. Chem. 261:1782–1785; Ohki, M. et al. (1986) J. Biol. Chem. 261:1778–1781). DnaJ/Hsp70 systems are involved in protein folding, (Georgopoulos, C. et al. (1993) Annu. Rev. Cell Biol. 9:601–734), protein degradation, assembly and disassembly of multiprotein complexes, (Cyr, D. et al. (1994) Trends Biochem. Sci. 19:176–181), and translocation of proteins across membranes. (Pfanner, N. et al. (1994) Trends Biochem. Sci. 19: 368–372).

The hyperproliferative phenotype of l(2)tid mutant embryos suggests that the Tid56 protein is involved in regulation of cell growth or death. Given the mitochondrial localization of Tid56 and the important role of mitochondria in regulating apoptosis, (Kroemer, G. et al. (1997) Immunol. Today 18:44–51; Green, D. R. et al. (1998) Science 281:1309–1312), the tumorous imaginal discs phenotype may reflect a failure of imaginal disc cells to properly integrate stimuli of cell death and survival. Several mitochondrial activities have been implicated in transducing, amplifying, and repressing apoptotic signals, including the release of cytochrome c and Apoptosis-Inducing Factor from the mitochondrial intermembrane space, the production of reactive oxygen species, and the loss of inner membrane potential. In addition, mitochondrial localization is important for the function of many of the Bcl-2 family of apoptosis regulators.

TID1 is a nuclear gene that encodes two alternatively spliced mitochondrial matrix-localized proteins, hTid-$1_L$ and hTid-$1_S$. (Syken, J. et al. (1999) Proc Natl Acad Sci U S A 96:8499–8504). Both hTid-$1_L$ and hTid-$1_S$ are homologs of the Drosophila tumor suppressor Tid56, (Schilling, B. et al. (1998) Virology 247:74–85; Kurzik-Dumke, U. et al. (1992) Differentiation 51:91–104; Kurzik-Dumke, U. et al. (1995) Dev Genet 16: 64–76), which is also localized to the mitochondria. (Kurzik-Dumke, U. et al. (1998) Cell Stress Chaperones 3:12–27). Loss of expression of Tid56 leads to the growth of lethal tumors in the imaginal discs of Drosophila larvae. Tid56, as well as hTid-$1_L$ and hTid-$1_S$, are members of the DnaJ family of molecular chaperones. (Silver, P. A. et al. (1993) Cell 74:5–6; Caplan, A. J. et al. (1993) Mol Biol Cell 4:555–563; Cyr, D. M. et al. (1994) Trends Biochem Sci 19:176–181). DnaJ proteins are characterized by a conserved J domain, and act as co-chaperones and specificity factors for Hsp70 family proteins. hTid-$1_L$ and hTid-$1_S$ have opposing, J domain-dependent effects on apoptosis; hTid-$1_L$ expression enhances apoptosis and hTid-$1_S$ expression suppresses apoptosis. (Syken, J. et al. (1999) Proc Natl Acad Sci USA 96:8499–8504). Mitochondria can act as regulators of apoptotic signal transduction, suggesting that the relative abundance or activity of these proteins may determine whether mitochondria amplify or dampen apoptotic or survival signals. Hence, we postulated that cells respond to certain physiological signals for death or survival by modulation of endogenous hTid-1 levels.

The death of T cells in response to extracellular signals has been studied extensively. When T helper (Th) cells are activated, they undergo a form of apoptotic cell death, known as activation-induced cell death (AICD). AICD results from repeated stimulation of the CD3/T cell receptor (TCR) complex, which results in the activation of the death receptor Fas and its downstream signaling components. AICD is involved in the deletion of self reactive T cells and the deletion of active T cells in order to terminate an immune response. (Green, D. R. et al. (1994) W. Curr Opin Immunol 6:476–487). Different sub-populations of Th cells exist. Th1 and Th2 cells produce distinct sets of cytokines and consequently have different functions. Upon activation, Th1 cells undergo AICD within 12 to 48 hours, while Th2 cells are more resistant to AICD. (Varadhachary, A. S. et al. (1997) Proc Natl Acad Sci USA 94:5778–5783; Zhang, X. et al. (1997) J Exp Med 185:1837–1849; Carter, L. L. et al. (1998) J Immunother 21:181–187). The mechanism underlying Th2 cell resistance to AICD is not clear, but is thought to involve inductive signaling through the CD3/TCR complex. (Varadhachary, A. S. et al. (1997) Proc Natl Acad Sci U S A 94:5778–5783).

Mitochondria have emerged as central regulators of apoptosis. Here, we show that TID1, a human homolog of the Drosophila tumor suppressor lethal (2) tumorous imaginal discs, l(2)tid, encodes two mitochondrial matrix proteins, designated hTid-$1_L$ and hTid-$1_S$. These splice variants are both highly conserved members of the DnaJ family of proteins, which regulate the activity of and confer substrate specificity to Hsp70 proteins. Both hTid-$1_L$ and hTid-$1_S$ coimmunoprecipitate with mitochondrial Hsp70. Expression of hTid-$1_L$ or hTid-$1_S$ have no apparent capacity to induce apoptosis but have opposing effects on apoptosis induced by exogenous stimuli. Expression of hTid-$1_L$ increases apoptosis induced by both the DNA-damaging agent mitomycin c and tumor necrosis factor alpha. This activity is J domain-dependent, because a J domain mutant of hTid-$1_L$ can dominantly suppress apoptosis. In sharp contrast, expression of hTid-$1_S$ suppresses apoptosis, whereas expression of a J domain mutant of hTid-$1_S$ increases apoptosis. Hence, we propose that TID1 gene products act to positively and negatively modulate apoptotic signal transduction or effector structures within the mitochondrial matrix.

We show that mTid-$1_S$, the murine homolog of the human, anti-apoptotic splice variant hTid-$1_S$ is induced in Th2 helper T cells by stimuli that promote activation. Th2 cells are refractory to a form of apoptosis known as activation-induced cell death (AICD). Expression of a dominant negative mutant Tid-$1_S$ protein abrogates resistance of Th2 cells to AICD, and allows for efficient activation of pro-caspase 3 in response to CD3 ligation. Hence, activation-induced accumulation of mTid-$1_S$ in Th2 cells may provide a novel mechanism that contributes to resistance to AICD.

The contents of Syken et al. (1999) PNAS 96:8499 are incorporated by reference herein. All other articles, patents and patent applications cited herein are also incorporated by reference herein.

(ii) Definitions

For convenience, certain terms employed in the specification, examples, and appended claims are collected here.

The term "TID1" refers to a gene encoding a Tid-1 polypeptide.

The terms "hTid-1$_L$" and "hTid-1$_S$" are used interchangeably herein with "hTid-1L" and "hTid-1S", respectively. The prefix "h" indicates that the protein or gene referred to is human, whereas the prefix "m" indicates that the protein or gene referred to is murine.

A "Tid-1 polypeptide" refers to a polypeptide having a significant sequence homology with a Tid-1 polypeptide having SEQ ID NO: 8 or 9 and differing from other polypeptides, and having at least one biological activity or antagonizing at least one biological activity of a wild-type Tid-1 polypeptide. Thus, Tid-1 polypeptides include full length wild-type polypeptides having SEQ ID NO: 8 and 9, and portions thereof containing sequences that are essentially specific to Tid-1 polypeptides. Polypeptides having at least 90% identity with the full length sequence set forth in SEQ ID NO: 8 and 9 are also referred to herein as Tid-1 polypeptides.

"Tid-1" nucleic acid is a nucleic acid encoding a Tid-1 polypeptide, or which presents a significant sequence homology to the full length SEQ ID NO: 1, 2, or 3, or to portions thereof which are significantly specific to nucleic acids having SEQ ID NO: 1, 2, 3 and differing from sequences of other genes.

"Agonists" of a Tid-1 polypeptide include Tid-1 polypeptides having at least one biological activity of a wildtype Tid-1 polypeptide (such as those having an amino acid sequence set forth in SEQ ID NO: 8 or 9), as well as compounds, which stimulate the expression or the activity of a wild-type Tid-1 polypeptide. A "Tid-1 polypeptide agonist" refers to a Tid-1 polypeptide which acts as an agonist.

"Antagonists" of a Tid-1 polypeptide include Tid-1 polypeptides antagonizing at least one biological activity of a wildtype Tid-1 polypeptide (such as those having an amino acid sequence set forth in SEQ ID NO: 8 or 9), as well as compounds, which inhibit the expression or the activity of a wild-type Tid-1 polypeptide. A "Tid-1 polypeptide antagonist" refers to a Tid-1 polypeptide which acts as an antagonist.

Apoptosis (or "normal" or "programmed" cell death) is the physiological process by which unwanted or useless cells are eliminated during development and other normal biological processes.

Apoptosis, is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy.

Cells undergoing apoptosis show characteristic morphological and biochemical features. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

Cytotoxicity is the cell-killing property of a chemical compound (such as a food, cosmetic, or pharmaceutical) or a mediator cell (cytotoxic T cell). In contrast to necrosis and apoptosis, the term cytotoxicity does not indicate a specific cellular death mechanism. For example, cell-mediated cytotoxicity (that is, cell death mediated by either cytotoxic T lymphocytes [CTL] or natural killer [NK] cells) combines some aspects of both necrosis and apoptosis.

A "chimeric protein" refers to a protein which includes polypeptide sequences from at least two different and distinct proteins. A chimeric protein can be a fusion protein, or the different polypeptide sequences can be covalently linked by a non-peptide bond, e.g., a cross-linking agent.

As used herein, the term "fusion protein" is art recognized and refer to a chimeric protein which is at least initially expressed as single chain protein comprised of amino acid sequences derived from two or more different proteins, e.g., the fusion protein is a gene product of a fusion gene.

The art term "fusion gene" refers to a nucleic acid in which two or more genes are fused resulting in a single open reading frame for coding two or more proteins that as a result of this fusion are joined by one or more peptide bonds.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exonic and (optionally) intronic sequences.

As used herein, the term "transfection" means the introduction of a heterologous nucleic acid, e.g., an expression vector, into a recipient cell by nucleic acid-mediated gene transfer. "Transformation", as used herein with respect to transfected nucleic acid, refers to a process in which a cell's genotype is changed as a result of the cellular uptake of exogenous DNA or RNA, and, for example, the transformed cell expresses a recombinant form of a Tid-1 polypeptide of the present invention.

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a fusion protein of the present invention) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes The ability to replicate in a host, usually conferred by an origin of replication, and a selection gene to facilitate recognition of transformants may additionally be incorporated. Vectors derived from viruses, such as retroviruses, adenoviruses, and the like, may be employed.

"Transcriptional regulatory sequence" is a generic term used throughout the specification to refer to DNA sequences, such as initiation signals, enhancers, and promoters and the like which induce or control transcription of protein coding sequences with which they are operably linked. In preferred embodiments, transcription of the fusion gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of one of the naturally-occurring forms of a Tid-1 protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of the immune system, e.g. Th2 cells, or cells of a neural origin, e.g. neuronal cells. The term also covers so-called "leaky" promoters, which regulate expression of a selected DNA primarily in one tissue, but cause expression in other tissues as well.

"Operably linked" when describing the relationship between two DNA regions simply means that they are functionally related to each other. For example, a promoter or other transcriptional regulatory sequence is operably linked to a coding sequence if it controls the transcription of the coding sequence.

"Recombinant host cells" refers to cells which have been transformed or transfected with vectors constructed using recombinant DNA techniques. As relevant to the present invention, recombinant host cells are those which produce Tid-1 proteins by virtue of having been transformed with expression vectors encoding these proteins.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a Tid-1 protein. The term "chimeric animal" is used herein to refer to animals in which the recombinant gene is found, or in which the recombinant is expressed in some but not all cells of the animal. The term "tissue-specific chimeric animal" indicates that the recombinant gene is present and/or expressed in some tissues but not others.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparision; a reference sequence may be a subset of a larger sequence, for example, as a segment of a full-length cDNA or gene sequence given in a sequence listing, such as a polynucleotide sequence of SEQ ID NO: 1–3, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (U.S.A.)* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human Tid-1 polynucleotide sequence shown in or the full-length murine or bovine $_c$ cDNA sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Nucleic Acids of the Invention:

The invention provides nucleic acids encoding TID1 proteins or fragments thereof, e.g., biologically active fragments, and the polypeptides encoded thereby. For simplicity, set forth below is the identification of the nucleotide and amino acid sequences presented in the sequence listing:

SEQ ID NO: 1 represents the nucleotide sequence of the full length human TID1 cDNA, as published in Schilling et al. (1998) Virology 247: 74. The sequence can be found in GenBank, under Accession No. NM_005147 and Accession No. AF061749.

SEQ ID NO: 2 represents the nucleotide sequence of the coding sequence of human TID1 cDNA represented in SEQ ID NO: 1 (nucleotides 32 to 1474) which encodes hTid-1L.

SEQ ID NO: 3 represents the nucleotide sequence of the coding sequence of the human TID1 cDNA encoding hTid-1S.

SEQ ID NO: 4 represents the nucleotide sequence of the coding sequence of the human TID1 cDNA encoding hTid-1L lacking the N-terminal 66 amino acids.

SEQ ID NO: 5 represents the nucleotide sequence of the coding sequence of the human TID1 cDNA encoding hTid-1S lacking the N-terminal 66 amino acids.

SEQ ID NO: 6 represents the nucleotide sequence of SEQ ID NO: 2 which encodes the 33 amino acid sequence of the carboxy terminus of hTid-1L.

SEQ ID NO: 7 represents the nucleotide sequence of SEQ ID NO: 3 which encodes the 6 amino acid sequence of the carboxy terminus of hTid-1S.

SEQ ID NO: 8 represents the amino acid sequence of hTid-1L.

SEQ ID NO: 9 represents the amino acid sequence of hTid-1S.

SEQ ID NO: 10 represents the amino acid sequence of hTid-1L lacking the N-terminal 66 amino acids.

SEQ ID NO: 11 represents the amino acid sequence of hTid-1S lacking the N-terminal 66 amino acids.

SEQ ID NO: 12 represents the amino acid sequence encoded by SEQ ID NO: 1.

SEQ ID NO: 13 represents the 33 amino acid carboxy terminus of htid-1L.

SEQ IDNO: 14 represents the 6 amino acid sequence of the carboxy terminus of hTid-1S.

The invention provides isolated Tid-1 nucleic acids, homologs thereof, and portions thereof. Preferred nucleic acids have a sequence at least 70%, and more preferably 75% homologous or identical and more preferably 80% and even more preferably at least 85% homologous with a nucleotide sequence of a TID1 gene or Tid-1 nucleic acid sequence set forth herein, e.g., such as a sequence shown in one of SEQ ID NOs: 1–7 and 12–16 or complement thereof. Nucleic acids at least 90%, more preferably 95%, and most preferably at least about 98–99% homologous with a nucleic sequence represented in one of the sequence set forth herein or complement thereof are of course also within the scope of the invention. In preferred embodiments, the nucleic acid is mammalian and in particularly preferred embodiments, includes all or a portion of the nucleotide sequence corresponding to the coding region. Even more preferred embodiments provide nucleic acids encoding Tid-1L or Tid-1S, or portions thereof.

The invention also pertains to isolated nucleic acids comprising a nucleotide sequence encoding Tid-1 polypeptides, variants and/or equivalents of such nucleic acids. The term "equivalent" is understood to include nucleotide sequences encoding functionally equivalent Tid-1 polypeptides or functionally equivalent peptides having an activity of a Tid-1 protein such as described herein. Equivalent nucleotide sequences will include sequences that differ by one or more nucleotide substitution, addition or deletion, such as allelic variants; and will, therefore, include sequences that differ from the nucleotide sequence of the Tid-1 genes herein due to the degeneracy of the genetic code.

Preferred nucleic acids are vertebrate Tid-1 nucleic acids. Particularly preferred vertebrate Tid-1 nucleic acids are mammalian. Regardless of species, particularly preferred Tid-1 nucleic acids encode polypeptides that are at least 70%, 80%, 90%, or 95% similar or identical to an amino acid sequence of a vertebrate Tid-1 protein, e.g., Tid-1$_L$ or Tid-1$_S$. In one embodiment, the nucleic acid is a cDNA encoding a polypeptide having at least one bio-activity of the subject Tid-1 polypeptide. Preferably, the nucleic acid includes all or a portion of the nucleotide sequence having SEQ ID No. 3.

Still other preferred nucleic acids of the present invention encode a Tid-1 polypeptide which is comprised of at least 2, 5, 10, 25, 50, 100, 150 or 200 amino acid residues. For example, such nucleic acids can comprise about 50, 60, 70, 80, 90, or 100 base pairs. Also within the scope of the invention are nucleic acid molecules for use as probes/primer or antisense molecules (i.e. noncoding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid represented by any of the sequences set forth herein, such as SEQ ID NO: 3 or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a Tid-1 nucleic acid of the present invention will bind to one of the nucleotide sequence disclosed herein, such as SEQ ID NO: 3 or complement thereof under moderately stringent conditions, for example at about 2.0×SSC and about 40° C. In a particularly preferred embodiment, a Tid-1 nucleic acid of the present invention will bind to one of SEQ ID NOs: 3 or 7 or complement thereof under high stringency conditions. High stringency hybridization refers to conditions wherein the hybridization is conducted in a solution comprising 2×SSC at about 65° C. and a wash in 0.2× SSC and 0.1% SDS at about 65° C.

Nucleic acids having a sequence that differs from the nucleotide sequences shown in any of the sequences disclosed herein, e.g., SEQ ID NO: 3 or complement thereof due to degeneracy in the genetic code are also within the scope of the invention. Such nucleic acids encode functionally equivalent peptides (i.e., a peptide having a biological activity of a Tid-1 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an TID-1 polypeptide. However, it is expected that DNA sequence polymorphisms that do lead to changes in the amino acid sequences of the subject Tid-1 polypeptides will exist among mammals. One skilled in the art will appreciate that these variations in one or more nucleotides (e.g., up to about 3–5% of the nucleotides) of the nucleic acids encoding polypeptides having an activity of a Tid-1 polypeptide may exist among individuals of a given species due to natural allelic variation.

Nucleic acids of the invention can encode one or more of the following domains of a Tid-1 protein: the 66 amino acid N-terminal sequence that is cleaved upon entry into the mitochondria; the J-domain (corresponding to amino acids 89 to 168 of SEQ ID Nos: 8 and 9); the 33 amino acid C-terminal portion of a Tid-1L protein (amino acids 448 to 480 of SEQ ID NO: 8); and the 6 amino acid C-terminal portion of the Tid-1S protein (amino acids 448 to 452 of SEQ ID NO: 9).

Yet other preferred nucleic acids are those which encode a mutant Tid-1 protein or portion thereof, wherein, e.g., the J-domain is mutated. A preferred mutation includes the substitution of the Histidine at position 121 of SEQ ID NO: 8 and 9.

Other nucleic acids of the invention include those encoding a J-domain from other J-domain containing proteins, shown e.g., in Schilling et al. (1998) *Virology* 247:74, which is incorporated herein by reference. Thus, in certain embodiments, a nucleic acid encoding a polypeptide comprising a J-domain from these proteins can be used instead of using J-domains from Tid-1 proteins. Such substitution is possible in view of the high degree of conservation in this domain in various proteins.

The polynucleotide sequence of the present invention may encode for a "mature" form of a Tid-1 portein, i.e., a form of Tid-1 which does not comprise the N-terminal 66 amino acids that are cleaved upon entry of the peptide into a mitochondria. However, generally, the nucleic acids of the invention will encode a Tid-1 polypeptide comprising a mitochondrial targeting sequence, such as amino acids 1–66 of the Tid-1 sequences disclosed herein. Mitochondrial targeting sequences from other proteins expressed in mitochondria may, of course, also be used.

The polynucleotide sequence may also encode a leader sequence, in situations in which it is desired to attach a Tid-1 polypeptide to a cell membrane or to obtain a soluble Tid-1 polypeptide secreted from a cell. The term "leader sequence" is used interchangeably herein with the term "signal peptide".

The polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150–21157) which includes a 10-residue sequence from c-myc, the pFLAG system (International Biotechnologies, Inc.), the pEZZ-protein A system (Pharmacia, NJ), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified.

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J Chromatography* 411:177; Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Ausubel et al. (1992) *Current Protocols in Molecular Biology*, eds. John Wiley & Sons).

Other preferred Tid-1 fusion proteins include Tid-1-immunoglobulin (Tid-1-Ig) polypeptide. Tid-1-Ig fusion proteins can be prepared as described e.g., in U.S. Pat. No. 5,434,131.

Figure 11:
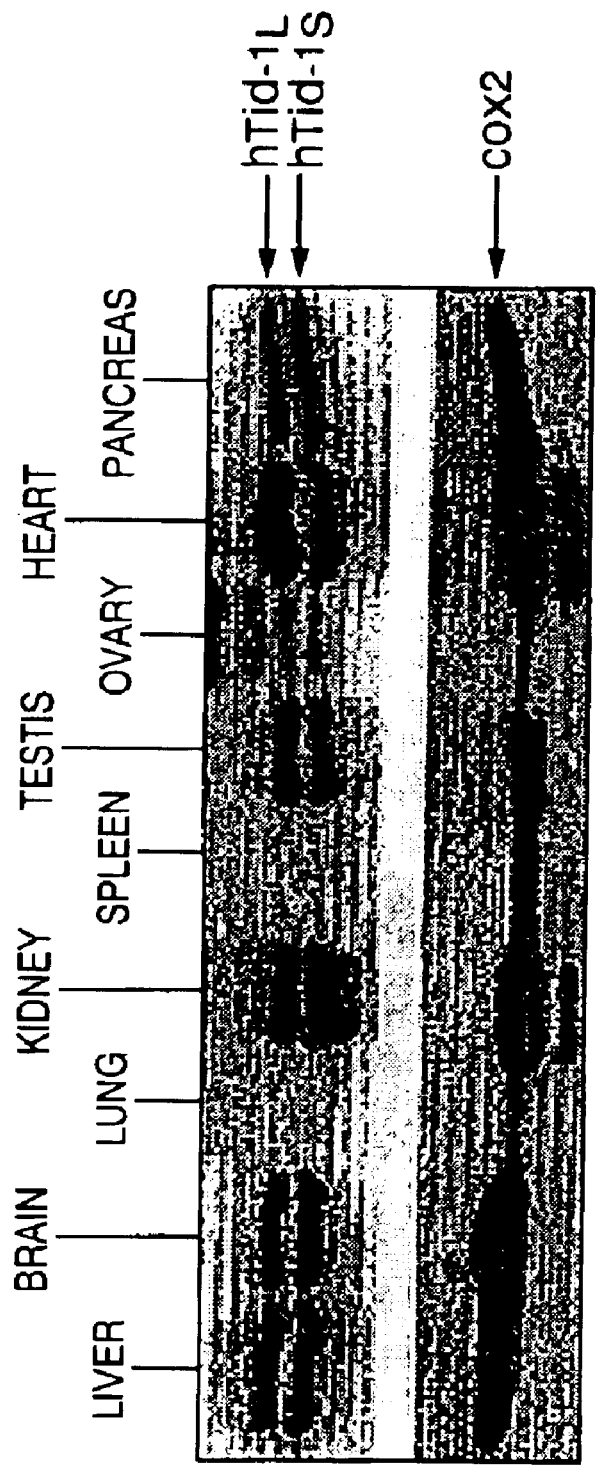
FIG. 11 shows expression of Tid-1 mRNA in several tissues.

Tid-1 protein-encoding nucleic acids can be obtained from mRNA present in any of a number of eukaryotic cells, e.g., from cardiac tissue or kidney (see FIG. 11 for additional tissues expressing high levels of Tid-1 proteins). It is also possible to obtain nucleic acids encoding Tid-1 polypeptides of the present invention from genomic DNA from both adults and embryos. For example, a gene encoding a Tid-1 protein can be cloned from either a cDNA or a genomic library in accordance with protocols described herein, as well as those generally known to persons skilled in the art. cDNA encoding a Tid-1 protein can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a Tid-1 protein can also be cloned using established polymerase chain reaction techniques in accordance with the nucleotide sequence information provided by the invention. The nucleic acid of the invention can be DNA or RNA or analogs thereof.

Preferred nucleic acids encode a vertebrate Tid-1 polypeptide comprising an amino acid sequence that is at least about 60% homologous, more preferably at least about 70% homologous and most preferably at least about 80% homologous with an amino acid sequence contained in any of the amino acid sequence set forth herein, e.g., SEQ ID No: 9. Nucleic acids which encode polypeptides at least about 90%, more preferably at least about 95%, and most preferably at least about 98–99% homology with an amino acid sequence represented in any of the sequence disclosed herein, e.g., SEQ ID No: 9 are also within the scope of the invention. In one embodiment, the nucleic acid is a cDNA encoding a peptide having at least one activity of the subject vertebrate Tid-1 polypeptide.

Preferred nucleic acids encode a bioactive fragment of a vertebrate Tid-1 polypeptide comprising an amino acid sequence at least about 60% homologous or identical, more preferably at least about 70% homologous or identical and most preferably at least about 80% homologous or identical with an amino acid sequence disclosed herein, e.g., SEQ ID No: 9. Nucleic acids which encode polypeptides which are at least about 90%, more preferably at least about 95%, and most preferably at least about 98–99% homologous or identical, with an amino acid sequence disclosed herein are also within the scope of the invention.

Bioactive fragments of Tid-1 polypeptides can be polypeptides having one or more of the following biological activities: the ability to modulate, e.g., enhance or decrease, apoptosis in a cell, the ability to interact with another molecule, and to catalyze a biological reaction. The interaction with another molecule can be an interaction mediated by the J-domain, or an interaction mediated by the 33 amino acid C-terminal domain of a Tid-1L polypeptide or by the 6 amino acid C-terminal domain of a Tid-1S polypeptide. Assays for determining whether a Tid-1 polypeptide has any of these or other biological activities are known in the art and are further described herein.

Nucleic acids encoding modified forms or mutant forms of Tid-1 are also within the scope of the invention. Preferred mutated forms are those encoding dominant negative mutants, examples of which are provide in the Examples. Other mutants include having mutated glycosylation sites, such that either the encoded Tid-1 protein is not glycosylated, partially glycosylated and/or has a modified glycosylation pattern. Amino acid sequence motifs required for the attachment of a sugar unit are well known in the art.

Other preferred nucleic acids of the invention include nucleic acids encoding derivatives of Tid-1 polypeptides which lack one or more biological activities of Tid-1 polypeptides. Also within the scope of the invention are nucleic acids encoding yet other splice variants or nucleic acids representing transcripts synthesized from an alternative transcriptional initiation site, such as those whose transcription was initiated from a site in an intron. Such homologs can be cloned by hybridization or PCR, as further described herein.

In preferred embodiments, the Tid-1 nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup B. et al. (1996) *Bioorganic & Medicinal Chemistry* 4(1):5-23). As used herein, the terms "peptide nucleic acids" or "PNAS" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *PNAS* 93:14670–675.

PNAs of Tid-1 can be used in therapeutic and diagnostic applications and are further described herein. Such modified nucleic acids can be used as antisense or antigene agents for sequence-specific modulation of gene expression or in the analysis of single base pair mutations in a gene by, e.g., PNA directed PCR clamping or as probes or primers for DNA sequence and hybridization (Hyrup B. et al (1996) supra; Perry-O'Keefe supra).

PNAs of Tid-1 can further be modified, e.g., to enhance their stability or cellular uptake, e.g., by attaching lipophilic or other helper groups to the Tid-1 PNA, by the formation of PNA-DNA chimeras, or by the use of liposomes or other techniques of drug delivery known in the art. Tid-1 PNAs can also be linked to DNA as described, e.g., in Hyrup B. (1996) supra and Finn P. J. et al. (1996) *Nucleic Acids Research* 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA. (Mag, M. et al. (1989) *Nucleic Acid Res*. 17:5973–88). PNA monomers are then coupled in a stepwise manner to produce a chimeric molecule with a 5'PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) *Bioorganic Med Chem. Lett*. 5:1119–11124).

In other embodiments, Tid-1 nucleic acids may include other appended groups such as peptides (e.g., for targeting host cell receptors in vivo), or agents that facilitate transport across the cell membrane as further described herein.

Probes and Primers

The nucleotide sequences of Tid-1 genes from mammalian organisms will further allow for the generation of probes and primers designed for use in identifying and/or cloning of Tid-1 homologs in other cell types, e.g., from other tissues, as well as Tid-1 homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence of any of the nucleotide sequences disclosed herein or naturally occurring mutants thereof. For instance, primers based on the nucleic acid represented in SEQ ID NOs: 6 or 7 can be used in PCR reactions to determine the presence of the long or the short form of a Tid-1 polypeptide or mRNA, respectively.

Likewise, probes based on the subject Tid-1 sequences can be used to detect transcripts or genomic sequences encoding the same or homologous proteins, for use, e.g., in prognostic or diagnostic assays (further described below). In preferred embodiments, the probe further comprises a label group attached thereto and able to be detected, e.g., the label group is selected from amongst radioisotopes, fluorescent compounds, enzymes, and enzyme co-factors.

Probes and primers can be prepared and modified as described in the other sections herein relating to nucleic acids.

Antisense Ribozyme and Triplex Techniques

Another aspect of the invention relates to the use of the Tid-1 nucleic acid in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject Tid-1 proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a Tid-1 protein. Alternatively, the antisense construct is an oligonucleotide probe which is generated ex vivo and which, when introduced into the cell causes inhibition of expression by hybridizing with the mRNA and/or genomic sequences of a Tid-1 gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *BioTechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the Tid-1 nucleotide sequence of interest, are preferred.

Antisense approaches may involve the design of oligonucleotides (either DNA or RNA) that are complementary to Tid-1 mRNA. The antisense oligonucleotides will bind to the Tid-1 mRNA transcripts and prevent translation. Thus, depending on the choice of antisense molecule, translation of the short or the long form of Tid-1 or both can be achieved. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. (1994) *Nature* 372:333). Therefore, oligonucleotides complementary to either the 5' or 3' untranslated, non-coding regions of a Tid-1 gene could be used in an antisense approach to inhibit translation of endogenous a Tid-1 mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of Tid-1 mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al. (1989) *Proc. Natl. Acad. Sci. U.S.A.* 86:6553–6556; Lemaitre et al. (1987) *Proc. Natl. Acad. Sci.* 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) *Bio Techniques* 6:958–976) or intercalating agents. (See, e.g., Zon (1988), *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) *Proc. Natl. Acad. Sci. U.S.A.* 93:14670 and in Eglom et al. (1993) *Nature* 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) *Nucl. Acids Res.* 15:6625–6641). The oligonucleotide is a 2'-0-methylribonucleotide (Inoue et al. (1987) *Nucl. Acids Res.* 15:6131–6148), or a chimeric RNA-DNA analogue (Inoue et al. (1987) *FEBS Lett.* 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) *Nucl. Acids Res.* 16:3209, methylphosphonate olgonucleotides can be prepared by use of controlled pore glass polymer supports. (Sarin et al. (1988) *Proc. Natl. Acad. Sci. U.S.A.* 85:7448–7451), etc.

The antisense molecules can be delivered to cells which express Tid-1 in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous Tid-1 transcripts and thereby prevent translation of the Tid-1 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region, (Bernoist et al. (1981) *Nature* 290:304–310), the promoter contained in the 3' long terminal repeat of Rous sarcoma virus (Yamamoto et al. (1980) *Cell* 22:787–797), the herpes thymidine kinase promoter (Wagner et al. (1981) *Proc. Natl. Acad. Sci. U.S.A.* 78:1441–1445), the regulatory sequences of the metallothionein gene (Brinster et al. (1982) *Nature* 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systematically).

Ribozyme molecules designed to catalytically cleave TID-1 mRNA transcripts can also be used to prevent translation of Tid-1 mRNA and expression of the long or the short form of Tid-1 polypepiptide, or both (See, e.g., PCT International Publication WO90/11364, published Oct. 4, 1990; Sarver et al. (1990) *Science* 247:1222–1225 and U.S. Pat. No. 5,093,246). While ribozymes that cleave mRNA at site specific recognition sequences can be used to destroy Tid-1 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) *Nature* 334:585–591. There are a number of potential hammerhead ribozyme cleavage sites within the nucleotide sequence of human Tid-1 cDNA. Preferably the ribozyme is engineered so that the cleavage recognition site is located near the 5' end of the Tid-1 mRNA; i.e., to increase efficiency and minimize the intracellular accumulation of non-functional mRNA transcripts. Use of a cleavage recognition site located in the sequence encoding the C-terminal 33 or 6 amino acid domains of the long and short forms of Tid-1, respectively, would allow the selective targeting of one or the other form of Tid-1, and thus, e.g., the increase or decrease of apoptosis in a cell.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) *Science* 224:574–578;

Zaug, et al. (1986) *Science* 231:470–475; Zaug, et al. (1986) *Nature* 324:429–433; published International patent application No. WO88/04300 by University Patents Inc.; Been, et al. (1986) *Cell* 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an Tid-1 gene.

As in the antisense approach, the ribozymes can be composed of modified oligonucleotides (e.g., for improved stability, targeting, etc.) and should be delivered to cells which express the Tid-1 gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous Tid-1 messages and inhibit translation. Because ribozymes unlike antisense molecules, are catalytic, a lower intracellular concentration is required for efficiency.

Endogenous Tid-1 gene expression or expression of a splice form thereof can also be reduced by inactivating or "knocking out" the Tid-1 gene or its promoter or a specific exon, e.g., the exon encoding the 33 amino acid C-terminal region of the long form of Tid-1 or the exon encoding the 6 amino aicd C-terminal region of the short form of Tid-1, using targeted homologous recombination. (E.g., see Smithies et al. (1985) *Nature* 317:230–234; Thomas, et al. (1987) *Cell* 51:503–512; Thompson et al. (1989) *Cell* 5:313–321; each of which is incorporated by reference herein in its entirety). For example, a mutant, non-functional Tid-1 (or a completely unrelated DNA sequence) flanked by DNA homologous to the endogenous Tid-1 gene (either the coding regions or regulatory regions of the Tid-1 gene) can be used, with or without a selectable marker and/or a negative selectable marker, to transfect cells that express Tid-1 in vivo. Insertion of the DNA construct, via targeted homologous recombination, results in inactivation of the Tid-1 gene or a splice form thereof. Such approaches are particularly suited in the agricultural field where modifications to ES (embryonic stem) cells can be used to generate animal offspring with an inactive Tid-1 (e.g., see Thomas, et al. (1987) and Thompson (1989) supra). However this approach can be adapted for use in humans provided the recombinant DNA constructs are directly administered or targeted to the required site in vivo using appropriate viral vectors.

Nucleic acid molecules to be used in triple helix formation for the inhibition of transcription of Tid-1 genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Vectors Encoding Tid-1 Proteins and Tid-1 Expressing Cells

The invention further provides plasmids and vectors encoding a Tid-1 protein, e.g., an agonist or antagonist polypeptide, which can be used to express a Tid-1 protein in a host cell. The host cell may be any prokaryotic or eukaryotic cell. Thus, a nucleotide sequence derived from the cloning of mammalian Tid-1 proteins, encoding all or a selected portion of the full-length protein or mutant forms thereof, can be used to produce a recombinant form of a Tid-1 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures well known in the art.

Vectors that allow expression of a nucleic acid in a cell are referred to as expression vectors. Typically, expression vectors used for expressing a Tid-1 protein, e.g., a dominant negative protein, or one of the long or the short form of the human Tid-1 protein contain a nucleic acid encoding a Tid-1 polypeptide, operably linked to at least one transcriptional regulatory sequence. Regulatory sequences are art-recognized and are selected to direct expression of the subject Tid-1 proteins. Transcriptional regulatory sequences are described in Goeddel, (1990) *Gene Expression Technology: Methods in Enzymology* 185, Academic Press, San Diego, Calif. In one embodiment, the expression vector includes a recombinant gene encoding a peptide having an agonistic activity of a subject Tid-1 polypeptide, or alternatively, encoding a peptide which is an antagonistic form of a Tid-1 protein.

Suitable vectors for the expression of Tid-1 polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) *Experimental Manipulation of Gene Expression*, ed. M. Inouye Academic Press 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, a Tid-1 polypeptide is produced recombinantly utilizing an expression vector generated by sub-cloning a nucleic acid comprising the nucleotide sequence set forth in SEQ ID Nos: 2 or 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, $2^{nd}$ Ed., ed. by Sambrook, Fritsch and Maniatis (Cold Spring Harbor Laboratory Press: 1989) Chapters 16 and 17.

In some instances, it may be desirable to express the recombinant Tid-1 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In addition to viral transfer methods, non-viral methods can also be employed to cause expression of a subject Tid-1 polypeptide in the tissue of an animal. Most non-viral methods of gene transfer rely on normal mechanisms used by mammalian cells for the uptake and intracellular transport of macromolecules. In preferred embodiments, non-viral targeting means of the present invention rely on endocytic pathways for the uptake of the subject Tid-1 polypeptide gene by the targeted cell. Exemplary targeting means of this type include liposomal derived systems, poly-lysine conjugates, and artificial viral envelopes.

In other embodiments transgenic animals, described in more detail below could be used to produce recombinant proteins.

Polypeptides of the Present Invention

The present invention makes available isolated Tid-1 polypeptides which are isolated from, or otherwise substantially free of other cellular proteins. The term "substantially free of other cellular proteins" (also referred to herein as "contaminating proteins") or "substantially pure or purified preparations" are defined as encompassing preparations of TID-1 polypeptides having less than about 20% (by dry weight) contaminating protein, and preferably having less than about 5% contaminating protein. Functional forms of the subject polypeptides can be prepared, as purified preparations by using a cloned gene as described herein.

Preferred Tid-1 proteins of the invention have an amino acid sequence which is at least about 60%, 70%, 80%, 85%, 90%, or 95% identical or homologous to an amino acid sequence of any of the sequences set forth herein. Even more preferred Tid-1 proteins comprise an amino acid sequence which is at least about 97, 98, or 99% homologous or identical to an amino acid sequence disclosed herein, e.g., SEQ ID NO: 9. Such proteins can be recombinant proteins, and can be, e.g., produced in vitro from nucleic acids comprising a nucleotide sequence set forth in SEQ ID NO: 3, or homologs thereof. For example, recombinant polypeptides preferred by the present invention can be encoded by a nucleic acid, which is at least 85% homologous and more preferably 90% homologous and most preferably 95% homologous with a nucleotide sequence set forth in any sequence disclosed herein, e.g., SEQ ID NO: 3. Polypeptides which are encoded by a nucleic acid that is at least about 98-99% homologous one of these sequences are also within the scope of the invention.

In a preferred embodiment, a Tid-1 protein of the present invention is a mammalian Tid-1 protein. In a particularly preferred embodiment a Tid-1 protein is set forth as SEQ ID No: 8 or 9. In particularly preferred embodiment, a Tid-1 protein has a Tid-1 bioactivity.

Full length proteins or fragments corresponding to one or more particular motifs and/or domains or to arbitrary sizes, for example, at least 5, 10, 25, 50, 75 and 100, amino acids in length are within the scope of the present invention.

For example, isolated Tid-1 polypeptides can be encoded by all or a portion of a nucleic acid sequence shown in any of SEQ ID NOs: 1, 2 or 3. Isolated peptidyl portions of Tid-1 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a Tid-1 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") Tid-1 protein. Such fragments could function as dominant negative mutants and selectively inhibit the activity of the long or the short form of a Tid-1 polypeptide.

Preferred portions of Tid-1 polypeptides are those that have a biological activity and act either as an antagonist or an agonist or the short or the long form of a Tid-1 protein, or both. An agonist of Tid-$1_L$ or Tid-$1_S$ can be, e.g., a polypeptide having the amino acid sequence set forth in SEQ ID Nos: 8 and 9, respectively. Alternatively, agonists can also be modified forms of these polypeptides, e.g., shorter polypeptides, or polypeptides having amino acid substitutions, deletions or additions. The activity of Tid-1 polypeptides can be tested as described herein. For example, the interaction with another molecule, e.g., a polypetpide can be determined in an in vitro assay measuring the interaction between the two polypeptides. Antagonist polypeptides can be obtained, e.g., by mutation of specific amino acids, which, e.g., inhibit the interaction of Tid-1 polypeptides with another polypeptide, either in the J-domain or in the C-terminal 33 amino acid or 6 amino acid domains. An antagonist can be, e.g., a dominant negative mutant. Exemplary antagonists are provided in the examples.

Other preferred proteins of the invention are those encoded by the nucleic acids set forth in the section pertaining to nucleic acids of the invention. In particular, the invention provides fusion proteins, which can provide, e.g., enhanced stability and solubility of Tid-1 proteins and may thus be useful in therapy. Fusion proteins can also be used to produce an immunogenic fragment of a Tid-1 protein. For example, the VP6 capsid protein of rotavirus can be used as an immunologic carrier protein for portions of a Tid-1 polypeptide, either in the monomeric form or in the form of a viral particle. The nucleic acid sequences corresponding to the portion of a subject Tid-1 protein to which antibodies are to be raised, e.g., the 33 or 6 amino acid C-terminal domains, can be incorporated into a fusion gene construct which includes coding sequences for a late vaccinia virus structural protein to produce a set of recombinant viruses expressing fusion proteins comprising Tid-1 epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a Tid-1 protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

In addition to utilizing fusion proteins to enhance immunogenicity, it is widely appreciated that fusion proteins can also facilitate the expression of proteins, and accordingly, can be used in the expression of the Tid-1 polypeptides of the present invention. For example, Tid-1 polypeptides can be generated as glutathione-S-transferase (GST-fusion) proteins. Such GST-fusion proteins can enable easy purification of the Tid-1 polypeptide, as for example by the use of glutathione-derivatized matrices (see, for example, *Current Protocols in Molecular Biology*, eds. Ausubel et al. (N.Y.: John Wiley & Sons, 1991)).

The present invention further pertains to methods of producing the subject Tid-1 polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant Tid-1 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant Tid-1 polypeptide is a fusion protein containing a domain which facilitates its purification, such as GST fusion protein.

Homologs of each of the subject Tid-1 proteins can be generated by mutagenesis, such as by discrete point mutation(s), or by truncation. For instance, mutation can give rise to homologs which retain substantially the same, or merely a subset, of the biological activity of the Tid-1 polypeptide from which it was derived.

The recombinant Tid-1 polypeptides of the present invention also include homologs of the wildtype Tid-1 proteins, such as versions of those protein which are resistant to proteolytic cleavage, as for example, due to mutations which alter ubiquitination or other enzymatic targeting associated with the protein.

Tid-1 polypeptides may also be chemically modified to create Tid-1 derivatives by forming covalent or aggregate conjugates with other chemical moieties, such as glycosyl groups, lipids, phosphate, acetyl groups and the like. Covalent derivatives of Tid-1 proteins can be prepared by linking the chemical moieties to functional groups on amino acid sidechains of the protein or at the N-terminus or at the C-terminus of the polypeptide.

Modification of the structure of the subject Tid-1 polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the Tid-1 polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, W H Freeman and Co.: 1981). Whether a change in the amino acid sequence of a peptide results in a functional TID-1 homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject Tid-1 proteins as well as truncation mutants, and is especially useful for identifying potential variant sequences (e.g., homologs). The purpose of screening such combinatorial libraries is to generate, for example, novel Tid-1 homologs which can act as either agonists or antagonist, or alternatively, possess novel activities all together. Thus, combinatorially-derived homologs can be generated to have an increased potency relative to a naturally occurring form of the protein.

In one embodiment, the variegated library of Tid-1 variants is generated by combinatorial mutagenesis at the nucleic acid level, and is encoded by a variegated gene library. For instance, a mixture of synthetic oligonucleotides can be enzymatically ligated into gene sequences such that the degenerate set of potential Tid-1 sequences are expressible as individual polypeptides, or alternatively, as a set of larger fusion proteins (e.g., for phage display) containing the set of Tid-1 sequences therein.

There are many ways by which such libraries of potential Tid-1 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential Tid-1 sequences. The synthesis of degenerate oligonucleotides is well known in the art (see for example, Narang, SA (1983) Tetrahedron 39:3; Itakura et al. (1981) Recombinant DNA, Proc $3^{rd}$ Cleveland Sympos. Macromolecules, ed. AG Walton, Amsterdam: Elsevier 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249:404–406; Cwirla et al. (1990) PNAS 87:6378–6382; as well as U.S. Pat. Nos. 5,223,409, 5,198,346, and 5,096,815).

Likewise, a library of coding sequence fragments can be provided for an Tid-1 clone in order to generate a variegated population of Tid-1 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an Tid-1 coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of Tid-1 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Tid-1 sequences created by combinatorial mutagenesis techniques.

Combinatorial mutagenesis has a potential to generate very large libraries of mutant proteins, e.g., in the order of 1026 molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin, et al. (1992) PNAS USA 89:7811–7815; Yourvan et al. (1992) Parallel Problem Solving from Nature 2, In Maenner and Manderick, eds., Elsevir Publishing Co., Amsterdam, 401-410; Delgrave et al. (1993) Protein Engineering 6(3):327–331).

The invention also provides for reduction of the Tid-1 proteins to generate mimetics, e.g., peptide or non-pepide agents, such as small molecules, which are able to disrupt binding of a Tid-1 polypeptide of the present invention with a molecule, e.g. target peptide. Thus, such mutagenic techniques as described above are also useful to map the determinants of the Tid-1 proteins which participate in protein-protein interactions involved in, for example, binding of the subject Tid-1 polypeptide to a target peptide. To illustrate, the critical residues of the C-terminal domain of a subject Tid-1 polypeptide which are involved in molecular interaction with another polypetpide can be determined and used to generate Tid-1 derived peptidomimetics or small molecules which competitively inhibit binding of the authentic Tid-1 protein with that moiety. By employing, for example, scanning mutagenesis to map the amino acid residues of the subject Tid-1 proteins which are involved in binding other proteins, peptidomimetic compounds can be generated which mimic those residues of the Tid-1 protein which facilitate the interaction. Such mimetics may then be used to interfere with the normal function of a Tid-1 protein. For instance, non-hydrolyzable peptide analogs of such residues can be generated using benzodiazepine (e.g., see Freidinger et al. (1988) Peptides: Chemistry and Biology, G. R. Marshall ed., ESCOM Publisher: Leiden, Netherlands), azepine (e.g., see Huffman et al. (1988) Peptides: Chemistry and Biology, G. R. Marshall ed., ESCOM Publisher: Leiden, Netherlands), substituted gamma lactam rings (Garvey et al. (1988) Peptides: Chemistry and Biology, G. R. Marshall ed., ESCOM Publisher: Leiden, Netherlands), keto-methylene pseudopeptides (Ewenson et al. (1986) J Med Chem 29:295; and Ewenson et al. (1985) Peptides: Structure and Function (Proceedings of the $9^{th}$ American Peptide Symposium) Pierce Chemical Co. Rockland, Ill.), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun 126:419; and Dann et al. (1986) Biochem Biophys Res Commun 134:71).

Another aspect of the present invention pertains to chimeric polypeptides which includes a heterologous peptide sequence ("internalizing peptide") which drives the translocation of an extracellular form of a thereapeutic polypeptide sequence across a cell membrane in order to facilitate intracellular localization of the thereapeutic polypeptide. In this regard, the therapeutic polypeptide sequence is one which is active intracellularly, such as a tumor suppressor polypeptide, transcription factor or the like. The internalizing peptide, by itself, is capable of crossing a cellular membrane by, e.g., transcytosis, at a relatively high rate. The internalizing peptide is conjugated, e.g., as a fusion protein, to a therapeutic polypeptide. The resulting chimeric polypeptide is transported into cells at a higher rate relative to the polypeptide alone to thereby provide an means for enhancing the introduction of inhibitory polypeptides into surrounding cells, e.g., to enhance gene therapy and/or topical applications of the therapeutic polypeptide. For convenience, the transcellular therapeutic polypeptides are described below as fusion proteins including Tid-1 polypeptide sequences, though as also described herein, many other protein domains can be used in place of the Tid-1 polypeptide.

In one embodiment, the internalizing peptide is derived from the *drosopholia antepennepedia* protein, or homologs thereof. The 60 amino acid long homeodomain of the homeo-protein antepennepedia has been demonstrated to translocate through biological membranes and can facilitate the translocation of heterologous polypeptides to which it is couples. See for example Derossi et al. (1994) *J Biol Chem* 269:10444–10450; Perez et al. (1992) *J Cell Sci* 102:717–722. Recently, it has been demonstrated that fragments as small as 16 amino acids long of this protein are sufficient to drive internalization. See Derossi et al. (1996) *J Biol Chem* 271:18188–18193. The present invention contemplates a chimeric protein comprising at least one J-domain and optionally a 33 or 6 amino acid C-terminal motif and at least a portion of the antepennepedia protein (or homolog thereof) sufficient to increase the transmembrane transport of the chimeric protein, relative to the Tid-1 protein alone, by a statistically significant amount.

Another example of an internalizing peptide is the HIV transactivator (TAT) protein. This protein appears to be divided into four domains (Kuppuswamy et al. (1989) *Nucl. Acids Res.* 17:3551–3561). Purified TAT protein is taken up by cells in tissue culture (Frankel, et al. (1989) *Cell* 55:1189–1193), and peptides, such as the fragment corresponding to residues 37–62 of TAT, are rapidly taken up by cell in vitro (Green, et al. (1989) *Cell* 55:1179–1188). The highly basic region mediates internalization and targeting of the internalizing moiety to the nucleus (Ruben et al. (1989) *J. Virol.* 63:1–8). Peptides or analogs that include a sequence present in the highly basic region, such as CFITKALGISYGRKKRRQRRRPPQGS, are conjugated to Tid-1 polypeptides (or portions thereof) to aid in internalization and targeting those proteins to the intracellular millieu.

Another exemplary transcellular Tid-1 polypeptide can be generated to include a sufficient portion of mastoparan (T. Higashijima et al. (1990) *J. Biol. Chem.* 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefor serve as an internalizing peptide for the subject transcellular Tid-1 polypeptides. Preferred growth factor-derived internalizing peptides include EGF (epidermal growth factor)-derived peptides, such as CMHIESLDSYTC and CMYIEALDKYAC; TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0–5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of Tid-1 polypeptides, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5–7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA(EALA)4-EALEALAA-amide, which represents a modification of the peptide sequence of Subbarao et al. (*Biochemistry* 26:2964 (1987)). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2–3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked Tid-1 polypeptide into the cell cytoplasm. Such internalizing peptides may be modeled after sequences identified in, e.g., Pseudomonas exotoxin A, clathrin, or Diphtheria toxin.

Pore-forming proteins or peptides may also serve as internalizing peptides herein. Pore forming proteins or peptides may be obtained or derived from, for example, C9 complement protein, cytolytic T-cell molecules or NK-cell molecules. These moieties are capable of forming ring-like structures in membranes, thereby allowing transport of attached Tid-1 polypeptide through the membrane and into the cell interior.

Mere membrane intercalation of an internalizing peptide may be sufficient for translocation of the Tid-1 polypeptide across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (Eubanks et al. (1988) *Peptides. Chemistry and Biology*, Garland Marshall (ed.), ESCOM, Leiden 566–69). In this construct, an internalizing, peptide would be attached to the C-terminus of the accessory peptide, since the N-terminal glycine is critical for the accessory moiety's activity. This hybrid peptide, upon attachment to a Tid-1 polypeptide at its C-terminus, is N-myristylated and will be translocated across the cell membrane.

Anti-Tid-1 Antibodies and Uses Therefor

Another aspect of the invention pertains to an antibody specifically reactive with a mammalian Tid-1 protein, e.g., a wild-type or mutated Tid-1 protein. For example, by using immunogens derived from a Tid-1 protein, e.g., based on the cDNA sequences, anti-protein/anti-peptide antisera or monoclonal antibodies can be made by standard protocols (See, for example, *Antibodies: A Laboratory Manual ed.* by Harlow and Lane (Cold Spring Harbor Press: 1988)). A mammal, such as a mouse, a hamster or rabbit can be immunized with an immunogenic form of the peptide (e.g., a mammalian Tid-1 polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of an Tid-1 protein can be administered in the presence of adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of Tid-1 protein of a mammal, e.g., antigenic determinants of a protein set forth in SEQ ID No: 8 or 9 or closely related homologs (e.g., at least 90% homologous, and more preferably at least 94% homologous). Preferred antibodies are those which selectively bind to either the long or the short form of a Tid-1 polypeptide. This can be achieved by preparing antibodies that are reactive against the C-terminal 33 or 6 amino acid domain of the long, or the short, form of Tid-1, respectively.

Following immunization of an animal with an antigenic preparation of an Tid-1 polypeptide, anti-Tid-1 antisera can be obtained and, if desired, polyclonal anti-Tid-1 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler, et al. (1975) *Nature*, 256:495–497), the human B cell hybridoma technique (Kozbar et al. (1983) *Immunology Today* 4:72), and the EBV-hybridoma technique to produce human monoclonal antibodies (Cole et al. (1985) *Monoclonal Antibodies and Cancer Therapy*, Alan R. Liss, Inc. 77–96). Hybridoma cells can be screened immunochemically for production of antibodies specifically reactive with a mammalian Tid-1 polypeptide of the present invention and monoclonal antibodies isolated from a culture comprising such hybridoma cells.

The term antibody as used herein is intended to include fragments thereof which are also specifically reactive with one of the subject mammalian Tid-1 polypeptides. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for an Tid-1 protein conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

One application of anti-Tid-1 antibodies of the present invention, in addition to diagnostic and therapeutic applications, is in the immunological screening of cDNA libraries constructed in expression vectors such as gt11, gt 18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a Tid-1 protein, e.g., other orthologs of a particular Tid-1 protein or other paralogs from the same species, can then be detected with antibodies, as, for example, reacting nitrocellulose filters lifted from infected plates with anti-Tid-1 antibodies. Positive phage detected by this assay can then be isolated from the infected plate. Thus, the presence of Tid-1 homologs can be detected and cloned from other animals, as can alternate isoforms (including splice variants) from humans.

Transgenic Animals

The invention further provides for transgenic animals, which can be used for a variety of purposes, e.g., to identify Tid-1 therapeutics. Transgenic animals of the invention include non-human animals containing a heterologous Tid-1 gene or fragment thereof under the control of an Tid-1 promoter or under the control of a heterologous promoter. Accordingly, the transgenic animals of the invention can be animals expressing a transgene encoding a wild-type Tid-1 protein or fragment thereof or variants thereof, including mutants and polymorphic variants thereof. Such animals can be used, e.g., to determine the effect of a difference in amino acid sequence of an Tid-1 protein from the sequence set forth in SEQ ID NO: 8 and 9, such as a polymorphic difference. These animals can also be used to determine the effect of expression of an Tid-1 protein in a specific site or for identifying Tid-1 therapeutics or confirming their activity in vivo.

Yet other non-human animals within the scope of the invention include those in which the expression of the endogenous Tid-1 gene or exon thereof has been mutated or "knocked out". These animals could be useful to further analyze the effect of the overexpression of a splice variant of Tid-1, in particular to determine whether these mice have or are likely to develop a specific disease, such as high susceptibility to inflammatory reactions. These animals are also useful for determining the effect of a specific amino acid difference in a Tid-1 gene. In fact these knock out animals can be crossed with transgenic animals expressing, e.g., a mutated form of Tid-1, thus resulting in an animal which expresses only the mutated protein and not the wild-type Tid-1 protein.

Methods for obtaining transgenic and knockout non-human animals are well known in the art.

Drug Screening Assays

According to one aspect of the present invention, Tid-1 genes and/or Tid-1 gene products are used for carrying out assays designed to identify agents which, by modulating the function of one or more of the Tid-1 genes, can be used to modify responses to apoptotic signals. As described in further detail below, test agents can be assessed in a cell-based or cell-free assay for ability to inhibit or potentiate the activity of all forms of the Tid-1 protein, or selectively inhibit or potentiate one of the particular splice variants. Merely to illustrate, the invention contemplates such drug-screening formats which detect compounds that, e.g., (1) modulate the interaction of the Tid-1 protein with other proteins (such as HSP-70 proteins or PV E7 proteins), nucleic acids, carbohydrates, lipids, organic molecules or other biological molecules, (2) modify an enzymatic activity of a Tid-1 protein, (3) modulate the half-life of a Tid-1 protein, (3) modulate the cellular localization of a Tid-1 protein, or (4) modulate the splicing of Tid-1 mRNA to either the Tid-1$_S$ or Tid-1$_L$ form. A variety of assay formats will suffice and, in light of the present inventions, will be comprehended by a skilled artisan.

Exemplary agents which can be tested in the subject drug screening assays include small organic molecules, e.g., having a molecular weight less than 2500 amu, more preferably less than less than 1000, 750 or 500 amu. Such molecules can include peptide and non-peptide moieties, nucleic acids, carbohydrates and the like. In many embodiments, it will be desirable to repeat the assay for a plurality of different test agents. For example, the subject assays can be repeated for at least 10 different test agents, and in other embodiments, for at least 100, or even at least 1000 different test agents.

(i) Cell-Free Assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements or with intrinsic enzymatic activity. Many forms of the Tid-1 proteins and Tid-1 splicing reactions identified herein will be amenable to some form of cell-free assay formats. Tid-1 polypeptides can be recombinantly expressed and at least partially purified, or provided as lysates, for use in cell-free assays. Membrane-associated proteins which may bind to Tid-1 can, in certain instances, be purified in detergent or liposomes, or isolated as part of a cell membrane fraction or organelle preparation.

Accordingly, in an exemplary screening assay of the present invention, a reaction mixture is generated including a Tid-1 polypeptide and one or more proteins (or other molecule) which interacts with the Tid-1 polypeptide, such molecules being referred to herein as "Tid-1-interacting partners" or "Tid-1-IP". Examples of Tid-1-IP include proteins that function upstream (including both activators and repressors of Tid-1 activity), and proteins or nucleic acids which function downstream of the Tid-1 polypeptide, whether they are positively or negatively regulated by it, e.g., such as an HSP-70 protein. The reaction mixture also includes one or more test compounds. Detection and quantification of complexes of the Tid-1 protein with upstream or downstream Tid-1-IP provide a means for determining a compound's efficacy at inhibiting or potentiating complex formation between Tid-1 and the Tid-1-IPs. The efficacy of the compound can be assessed by generating dose response curves from data obtained using various concentrations of the test compound. Moreover, a control assay can also be performed to provide a baseline for comparison. In one control assay, isolated and purified Tid-1 polypeptide is added to a composition containing the Tid-1-IP, and the formation of a complex is quantitated in the absence of the test compound.

Complex formation between the Tid-1 polypeptide and a binding partner may be detected by a variety of techniques. Modulation of the formation of complexes can be quantitated using, for example: detectably labeled proteins such as radiolabeled, fluorescently labeled, or enzymatically labeled proteins; by immunoassay; or by chromatographic detection.

Typically, it will be desirable to immobilize either Tid-1 or its interacting partner to facilitate separation of complexes from uncomplexed forms of one or both of the proteins, as well as to accommodate automation of the assay. Binding of the Tid-1 protein to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/Tid-1 (GST/Tid-1) fusion proteins can be adsorbed onto glutathione sepharose beads (Sigma Chemical, St. Louis, Mont.) or glutathione derivatized microtitre plates, which are then combined with a cell lysate or other preparation including the Tid-1-IP and the test compound, and the mixture incubated under conditions conducive to complex formation (in the absence of the test compound), e.g. at physiological conditions for salt and pH, though slightly more stringent conditions may be desired. Following incubation, the beads are washed to remove any unbound Tid-1-IP, and the matrix immobilized and the amount of Tid-1-IP in the matrix determined, or in the supernatant after the complexes are subsequently dissociated. Alternatively, the complexes can be dissociated from the matrix, separated by SDS-PAGE, and the level of Tid-1-IP found in the bead fraction quantitated from the gel using standard electrophoretic techniques.

Other techniques for immobilizing proteins or nucleic acids on matrices are also available for use in the subject assay. For instance, either Tid-1 or its cognate binding partner can be immobilized utilizing conjugation of biotin and streptavidin. For instance, biotinylated Tid-1 proteins can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the Tid-1 protein, but which do not interfere with binding of upstream or downstream binding partners, can be derivatized to the wells of the plate, and the Tid-1 protein trapped in the wells by antibody conjugation. As above, preparations of an Tid-1-IP and a test compound are incubated in the Tid-1-presenting wells of the plate, and the amount of complex trapped in the well can be quantitated. Exemplary methods for detecting such complexes, in addition to those described above for the GST-immobilized complexes, include immunodetection of complexes using antibodies reactive with the Tid-1 binding partner, or which are reactive with the Tid-1 protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with an Tid-1-IP. To illustrate, the Tid-1-IP can be chemically cross-linked or genetically fused with horseradish peroxidase, and the amount of polypeptide trapped in the complex can be assessed with a chromogenic substrate of the enzyme, e.g. 3,3'-diamino-benzadine tetrahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al. (1974) *J. Biol. Chem.* 249:7130).

For processes which rely on immunodetection for quantitating one of the proteins trapped in the complex, antibodies against the protein, such as anti-Tid-1 antibodies, can be used. Alternatively, the protein to be detected in the complex can be "epitope tagged" in the form of a fusion protein which includes a second polypeptide sequence for which antibodies are readily available (e.g. from commercial sources). For instance, the GST fusion proteins described above can also be used for quantification of binding using antibodies against the GST moiety. Other useful epitope tags include mycepitopes (e.g., see Ellison et al. (1991) *J. Biol. Chem.* 266:21150–21157) which includes a 10-residue sequence from c-myc, as well as the pFLAG system (International Biotechnologies, Inc.) or the pEZZ-protein A system (Pharmacia, N.J.).

In still another embodiment, the subject assay is derived to detect agents which can inhibit (or potentiate) the formation of a particular Tid-1 splice variant, e.g., by influencing the splicing event or the stability of the resulting transcript. In vitro versions of such assays can be carried out using splicing cocktails, e.g., cell lysates or reconstituted protein preparations, and detecting the formation of the mature transcript. For instance, alternative splicing can be detected by RNase protection assays, or simply by the quantity and size of PCR amplification products using primers which give amplimers including the unspliced, 1L and/or IS products. Alternatively, the presence of the short or the long proteins can be detected by, e.g., gel electrophoresis or by using antibodies that are specific for either form.

(ii) Cell Based Assays

In addition to cell-free assays, such as described above, the readily available of each of the Tid-1 variants provided by the present invention also facilitates the generation of cell-based assays for identifying small molecule agonists/antagonists and the like. The ability of a test agent to alter the activitiy of a Tid-1 protein in the cell may include directly detecting the formation of complexes including a Tid-1 protein, detecting an intrinic enzymatic activity of a Tid-1 protein, directly detecting a change in cellular localization of a Tid-1 protein, detecting a post-translational modification to a Tid-1 protein or a change in the stability of a Tid-1 protein, or detecting the downstream consequence of any one of such events—such as apoptosis of the test cell.

One aspect of the present invention provides a method for detecting changes in Tid-1 dependent permeability of mitochondria of a cell. In general, the method utilizes a cell engineered to express a reporter protein which is localized to the mitochondria of the cell, wherein the reporter protein is heterologous to the mitochondria and produces a detectable signal upon leakage from the mitochondria. The method involves detecting the level of the signal produced by the leakage of the reporter protein from the mitochondria. For instance, the method can be carried including such steps as (i) providing a cell engineered to express a reporter protein which is localized to the mitochondria of the cell, which reporter protein is heterologous to the mitochondria and is released from the mitochondria, and becomes sufficiently detectable in other cellular compartments, as part of an early event in apoptosis; and (ii) detecting the changes in the level of the reporter protein in the mitochondria or other cellular compartments, wherein a release of the reporter protein from the mitochondria indicates the induction of apoptosis. In certain preferred embodiments, the reporter protein is directly detectable upon release from the mitochondria. For instance, the reporter protein can have a fluorescence or intrinsic enzymatic activity.

In yet another embodiment, substrates for caspases activated as part of an apoptotic signal can be used, e.g., the assay detects the rate of conversion of the substrate to product. Exemplary caspase substrates are described in U.S. Pat. No. 5,976,822.

In yet another aspect of the invention, the subject drug screening assays can utilized the Tid-1 proteins to generate a "two hybrid" assay (see, for example, U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and PCT Publication No. WO 94/10300). Briefly, the two hybrid assay relies on reconstituting in vivo a functional transcriptional activator protein from two separate fusion proteins. In particular, the method makes use of chimeric genes which express hybrid proteins. To illustrate, a first chimeric gene can be generated with the coding sequence for a DNA-binding domain of a transcriptional activator fused in frame to the coding sequence for an Tid-1 protein. The second hybrid protein encodes a transcriptional activation domain fused in frame to another polypeptide, e.g., and Tid-1-IP, which binds to the Tid-1 protein. If the two fusion proteins are able to interact, e.g., form an Tid-1-dependent complex, they bring into close proximity the two domains of the transcriptional activator. This proximity is sufficient to cause transcription of a reporter gene which is operably linked to a transcriptional regulatory site which is bound by the DNA-binding domain of the first fusion proteins, and expression of the reporter gene can be detected and used to score for the interaction of the Tid-1 and sample proteins.

Diagnostic Methods of the Invention

The invention provides methods for determining whether a subject has or is likely to develop a condition that results from, or correlates, with an improper level or form or activity of a Tid-1 polypeptide. For example, it has been demonstrated herein that different splice variants of the TID1 gene encode Tid-1 polypeptides having different activities. More specifically, Tid-1L is a polypeptide, which enhances apoptosis caused by an exogenous stimulus, whereas Tid-1S is a polypeptide, which renders cells resistant to apoptosis induced by an exogenous stimulus. Furthermore, it has also been shown herein that Tid-1S has an anti-apoptotic effect in Th2 cells, but not in Th1 cells. Accordingly, a disregulation of the level or activity of one or more splice variants of TID1 is likely to result in a pathological condition, e.g., an immunological condition. For example, it is likely that a disease characterized by cell degeneration is caused at least in part by an abnormal level in one or more of the splice products of TID1, e.g., an increased level of Tid-1L and/or a decreased level of Tid-1S. An abnormal level or activity of polypeptides encoded by splice variants could result from mutations in the TID1 gene, in the coding, non-coding or regulatory, e.g., promoter region. In particular, since it has been shown that a mutation in the J-domain of Tid-1 polypeptides results in a dominant negative protein, it is likely that naturally-occurring mutations in this domain result in a disease or condition. Similarly, since the presence of the 33 amino acid and 6 amino acid C-terminal domains in a Tid-1 polypeptide give rise to a polypeptide having opposite biological activities, these domains play an important role in the biological activity of Tid-1 polypeptides, and a mutation in these domains is likely to cause a deregulation in the activity of these proteins.

Thus, the invention provides reagents and methods for determining the level and activity of Tid-1 polypeptides in cells and in subjects. In one embodiment, the method includes the detection of mutations in Tid-1 genes, using, e.g., nucleic acids described herein. In another embodiment, the method includes the detection of a Tid-1 polypeptide or mRNA, and, e.g., determination of its level in a cell. This particular method can be used with the antibodies described further herein.

Therapeutic Methods of the Invention

As described herein, TID-1 genes encode mRNAs which are differentially spliced and which encode polypeptides having either an enhancing, or an inhibitory effect on apoptosis. These polypeptides modulate apoptosis induced by various stimuli, including TNF-alpha and the DNA-damaging agent mitomycin c (MMC). In Th2 cells, the splice variant Tid-1S provides resistance of the cells to a form of apoptosis known as "activation-induced cell death" (AICD), which regulates the life span of Th2 cells, to ultimately regulate immune responses. In view of the wide tissue distribution of Tid-1 polypeptides, these polypeptides are likely to be involved in regulating apoptosis in numerous tissues. As discussed above, a deregulation of the level or activity of one or more Tid-1 splice variant is likely to be at least in part responsible for the generation of diseases or conditions, such as abnormal immune responses.

Such diseases can be treated by the administration of an agonist or antagonist of a Tid-1 polypeptide. For example, in a situation in which the activity of Tid-1S is abnormally low due to a mutation in the gene, the treatment would comprise administering to the subject a Tid-1 S polypeptide.

In addition to providing methods for treating diseases resulting from an abnormal level or activity of at least one splice variant of Tid-1, the invention also provides methods for regulating apoptosis, in particular mitochondrial apoptosis, in other situations. For example, the invention provides a method for treating diseases or disorders that are caused by an excessive antibody production, by inhibiting the activity and/or cell number of Th2 cells. The invention also provides methods for treating diseases or conditions that could be improved by increasing the production of antibodies, such as microbial infections.

Since it has also been reported that the number of Th cells of one type can be increased by a decrease in the number of Th cells of the other type, the invention also provides methods for regulating the number of Th1 cells by regulating the number of Th2 cells. Thus, the invention provides a method for treating a disease that is caused or that worsens due to an excessive number of Th1 cells, comprising increasing the number of Th2 cells. Alternatively, the invention also provides a method for treating a disease that is caused or contributed to by an abnormally low number of Th1 cells, comprising reducing the number of Th2 cells in the subject.

A decrease in the number of Th2 cells can be achieved by reducing the level and/or activity of Tid-1S and/or by increasing the level and/or activity of Tid-1L. Alternatively, an increase in the number of Th2 cells can be achieved by increasing the level or activity of Tid-1S and/or by decreasing the level and/or activity of Tid-1L. Thus, in one embodiment, the number of Th2 cells in a subject is decreased by introducing into the Th2 cells a dominant negative mutant of Tid-1S, such as a Tid-1S containing a functional mutation in the J-domain (see Examples). Alternatively, a small molecule drug which inhibits the activity of Tid-1S can be administered. Such a drug can, for example, inhibit the interaction of Tid-1S with another polypeptide. On the other hand, the number of Th2 cells can be increased by providing Tid-1S agonists, e.g., a Tid-1S polypeptide, which will prevent the Th2 cells to undergo apoptosis. The number of Th2 cells can also be increased by inhibiting the activity of Tid-1L, such as by introducing into the Th2 cells a Tid-1L dominant negative mutant (see Examples). Alternatively, a small molecule drug which inhibits the activity of Tid-1L can also be administered.

Diseases or conditions which are improved by an increase in Th2 cells include those in which an increased production of antibodies is desired. These include any infection by a microorganism which resides extracellularly for at least part of its life cycle, e.g., bacterial and viruses, e.g., papillomaviruses and herpes simplex viruses.

Other diseases in which an increase in Th2 is beneficial include inflammatory diseases of the central nervous system, e.g., demyleinating diseases, such as multiple sclerosis (see, e.g., Nagelkerken (1998) *Braz J. Med. Biol. Res.* 31:55).

Diseases or conditions which are improved by a decrease in Th2 cells include those in which antibodies are a cause of the disease. Such diseases include certain autoimmune diseases, e.g., arthritis Hashimoto's thyroiditis, lupus, diabetes.

Other conditions that can be improved by a reduction in Th2 cells include allergies, in particular asthma.

In a particular embodiment, the invention provides a method for treating or at least improving the symptoms of an infection by an immunodeficiency virus, e.g., HIV. It has in fact been observed that HIV-infected individuals undergo a shift from a Th1 response to a Th2 response, which seems to give inferior protection against further HIV infection, leading to a more rapid disease progression. Thus, a reduction of the number of Th2 cells according to the method of the invention would improve the status of HIV patients.

Based at least on the observation that Tid-1 polypeptides are present in numerous types of cells, the invention also provides methods for modulating apoptosis in these cells. For example, cancer may be improved by increasing apoptosis of cancer cells. The treatment may include contacting the cells with an agent inducing apoptosis and a Tid-1S agonist, and optionally a Tid-1L antagonist. Degenerative diseases, e.g., Alzheimer's disease, on the other hand may be improved by inhibiting apoptosis.

Thus, generally, the invention is useful for the treatment and/or prevention of any diseases/disorder which can be improved by increasing or decreasing apoptosis in cells, or by increasing or decreasing the sensitivity of cells to apoptosis. To further illustrate, some pathological situations exhibit a modified, if not deregulated, mechanism of apoptosis or a mechanism of apoptosis which does not provide for a deregulation of another biological phenomenon in order to achieve equilibrium. Thus, it has been reported that deliberate modulation of apoptosis, by inducing it or suppressing it, can make it possible to treat a large number of diseases such as diseases which are linked to an inadequate rate of apoptosis, as in the case of cancer, or to autoimmune diseases or allergies, or, on the contrary, diseases which are linked to an excessive rate of apoptosis, as in the cases of the human immunodeficiency virus (HIV) immunodeficiency syndrome, neurodegenerative diseases (Alzheimer's disease) or excessive damage which is induced during myocardial infarction.

For instance, apoptosis inhibitor identified by the assays of the present invention can be used as an agent for prophylaxis and treatment of a disease mediated by promotion of apoptosis in mammals (e.g., man, mouse, rat, rabbit, dog, cat, bovine, equine, swine, monkey, etc.). Examples of such disease includes viral diseases such as AIDS and fulminant hepatitis; neurodegenerative diseases such as Alzheimer's disease, Parkinson's disease, amyotrophic lateral sclerosis and other diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; graft rejections; and etc. The apoptosis inhibitor of the present invention is especially preferably used as an agent for prophylaxis or treatment of a neurodegenerative disease.

The composition according to the invention may be administered by the enteral, parenteral, topical or ocular route. Preferably, the pharmaceutical composition is packaged in a form which is suitable for administration by the systemic route (for injection or perfusion). Examples of dosage forms of the apoptosis inhibitor of the present invention include oral dosage forms such as tablets, capsules (inclusive of soft capsules and microcapsules), powders, granules, and syrups; and non-oral dosage forms such as injections, suppositories, pellets, and drip infusions. The dosage of the apoptosis inhibitor of the present invention differs depending on the subject, route of administration, clinical condition, etc.

Methods for administering drugs, including small molecules, polynucleotides and polypeptides are well known in the art. In particular, a seris of eukaryotic expression vectors are known for introducing and expressing genes in humans. Such vectors include adenoviruses, adeno-associated viruses, hybrids thereof, herpes simplex derived vectors and many others. Gene therapy trials using several of these vectors are currently ongoing, indicating that use of these vectors is believed to be sufficiently safe for use in humans.

Nucleic acids of the invention can be introduced into cells in a subject. Alternatively, cells of a subject can be obtained, and these cells transformed ex vivo with the constructs of the invention, and then administered to a subject. Such a method is applicable, e.g., to bone marrow that is obtained from a subject and administered to the same or another subject.

Other Applications of the Invention

Also within the scope of the invention are methods for regulating the half life of cells in culture. In one embodiment, cells which are grown in culture, e.g., primary cells, are treated such as to increase the level or activity of Tid-1S in the cells, such as to decrease their susceptibility to cell death triggered by an external or internal stimulus. In particular, this technique allows the prolonged maintenance in culture of Th2 cells. This technique would benefit the culture of any type of cell that is susceptible to apoptosis. In an illustrative embodiment, a cell culture is transformed with a nucleic acid encoding Tid-1S or an agonist thereof, and optionally with a Tid-1L antagonist. Alternatively, cells can be incubated with a compound that increases gene expression or activity of Tid-1S and/or a compound that decreases gene expression or activity of Tid-1L.

Kits of the Invention

The invention further provides kits for using in the diagnostic or therapeutic methods of the invention. Such kits comprise, e.g., nucleic acid probes for detecting one or more splice products of a TID-1 gene. Other kits comprise one or more antibodies. Yet other kits comprise Tid-1 polypeptides and/or mimetics thereof for treating diseases or conditions, or generally for modulating apoptosis in cells.

The present invention is further illustrated by the following examples which should not be construed as limiting in any way. The contents of all cited references including literature references, issued patents, published or non published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); Oligonucleotide Synthesis (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986) (Cold Spring Harbor Laboratory Press, Cold Spring Harbor, N.Y., 1986).

Exemplification

The invention now being generally described, it will be more readily understood by reference to the following examples which are included merely for purposes of illustration of certain aspects and embodiments of the present invention, and are not intended to limit the invention.

EXAMPLE 1

TID1 Encodes Two Mitochondria-Localized Splice Variants, hTid-1$_L$ and hTid-1$_S$ To detect endogenous TID1 related proteins, human osteosarcoma SAOS-2 cells were fractionated and analyzed by immunoblot by using hTid-1-specific mAbs. The major proteins detected by two independent mAbs, which we have named hTid-1$_L$ and hTid-1$_S$, have apparent molecular masses of 43 kDa and 40 kDa, respectively. Both hTid-1$_L$ and hTid-1$_S$ fractionate with the mitochondrial proteins cytochrome c and COx1 (FIG. 1A). This result is consistent with immunofluorescence and immunoelectron microscopy experiments, which show that like Tid56, TID$_1$-encoded proteins colocalize with mitochondria.

Figure 1B:
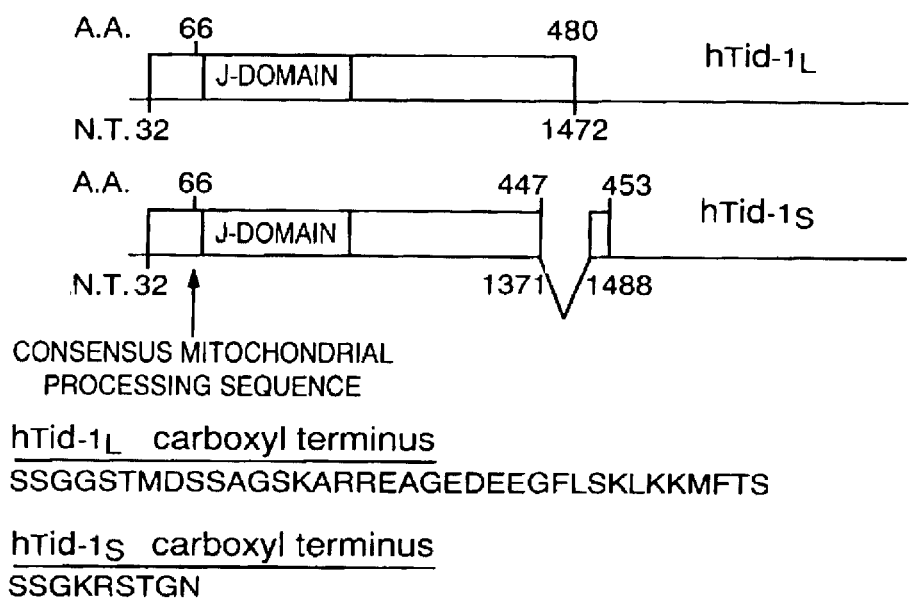
FIG. 1B. hTid-$1_L$ and hTid-$1_S$ are splice variants of TID1. hTid-$1_L$ mRNA encodes a protein with a predicted molecular mass of 52 kDa, which is cleaved at its amino terminus to form hTid-$1_L$. Mature hTid-$1_L$ migrates with an apparent molecular mess of 43 kDa on SDS/PAGE. hTid-$1_S$ is encoded by an mRNA in which an exon encoding the carboxyl-terminal 33 aa (SEQ ID NO: 22) of hTid-$1_L$ is removed and replaced with an exon from the 3'-untranslated region of hTid-$1_L$ mRNA, which encodes 6 aa and a stop codon (SEQ ID NO: 23). hTid-$1_S$ mRNA encodes a protein with a predicted molecular weight of 49.5 kDa, which is cleaved at its amino terminus to form hTid-$1_S$. Mature hTid-$1_S$ migrates with an apparent molecular mass of 40 kDa on SDS/PAGE. Both hTid-$1_L$ and hTid-$1_S$ have a consensus mitochondrial cleavage site at amino acid position 66.
Figure 1C:
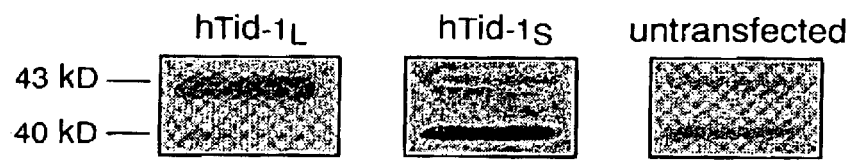
FIG. 1C. Expression of a cDNA of hTid-$1_L$ (Left) or hTid-$1_S$ (Center) gives rise to proteins of 43 and 40 kDa, respectively, that comigrate on SDS/PAGE with the endogenous hTid-1 polypeptides from untransfected U2OS cells (Right).

Evidence from expressed sequence tag database searches suggested that hTid-1$_L$ and hTid-1$_S$ may represent the protein products derived from two alternatively spliced mRNAs. (Schilling, B. et al. (1998) *Virology* 247:74–85). PCR analysis of a human embryonic brain-derived cDNA library revealed two TID1 cDNAs. The long form matched the TID1 cDNA originally cloned, whereas the shorter form represents the alternatively spliced form of TID1 predicted from analysis of the expressed sequence tag database. In the alternatively spliced cDNA, an exon encoding the carboxyl-terminal 33 aa and the stop codon from the original clone is replaced with an exon located within the 3'-untranslated region of the original clone that encodes 6 aa and a stop codon (FIG. 1B). Expression of the originally published TID1 cDNA clone, including the 3'-untranslated region, leads to the production of both hTid-1$_L$ and hTid-1$_S$. Expression of a TID1 cDNA in which the 3'-untranslated region has been removed leads to the production of only the 43-kDa band, which comigrates with endogenous hTid-1$_L$ on SDS/PAGE. Expression of the alternatively spliced form in cells leads to production of a 40-kDa band that comigrates with endogenous hTid-1$_S$ (FIG. 1C). Hence, we conclude that hTid-1$_L$ and hTid-1$_S$ are encoded by alternatively spliced mRNAs of the TID1 gene. Most mitochondrial matrix proteins encoded by nuclear DNA are cleaved at their amino terminus on entering the mitochondria. Both hTid-1$_L$ and hTid-1$_S$ have a predicted mitochondrial processing sequence (LRP-GV), (Gavel, Y. et al. (1990) *Protein Eng.* 4:33–37), that would result in cleavage at amino acid 66 on entry into the mitochondria. The predicted mature hTid-1$_L$ and hTid-1$_S$ proteins consist of 415- and 388-aa residues and have predicted molecular masses of 45.6 and 42.7 kDa, respectively. Hence, the mature hTid-1$_L$ and hTid-1$_S$ represent cleavage products of cytoplasmic pre-proteins.

EXAMPLE 2 hTid-1$_L$ and hTid-1$_S$ are Localized to the Mitochondria Matrix and Interact with mtHsp70

Figure 2A:
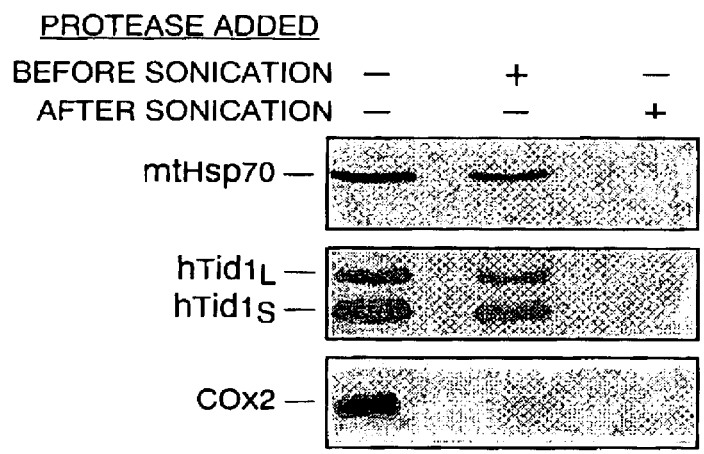
FIG. 2A. hTid-$1_L$ and hTid-$1_S$ are localized to the mitochondrial matrix and form complexes with mtHsp70. U2OS cells were homogenized, and mitochondria were isolated. Mitochondria were swelled in hypotonic buffer to burst the outer mitochondrial membrane. Samples went untreated or were treated with proteinase K before or after sonication, which disrupts the mitochondrial inner membrane. Samples were analyzed by immunoblot for the presence of matrix-localized mtHsp70, hTid-1, and the mitochondrial inner membrane protein COx2. COx2 is digested before sonication, indicating that the inner mitochondrial membrane is exposed to protease. hTid-1 $_L$, hTid-$1_S$, and mtHsp70 are only digested when proteinase K is added after the mitochondrial inner membrane is disrupted by sonication.

To determine the submitochondrial localization of hTid-1$_L$ and hTid-1$_S$, mitochondria were subjected to a proteinase protection assay. Mitochondria were swelled in hypotonic buffer, which causes the outer membrane to rupture, and then treated with proteinase K before or after sonication, which ruptures the inner membrane. The samples were then analyzed by immunoblotting for the presence of hTid-1, matrix-localized mtHsp70 and the mitochondrial inner membrane protein COx2 (FIG. 2A). Addition of proteinase K before sonication left hTid-1$_L$, hTid-1$_S$, and mtHsp70 intact, but led to the proteolytic digestion of COx2, indicating that the intermembrane space was exposed to protease. Addition of proteinase K after sonication, however, led to complete proteolytic digestion of hTid-1$_L$, hTid-1$_S$, and mtHsp70. These results indicate that, like mtHsp70, hTid-1$_L$ and hTid-1$_S$ are mitochondrial matrix-localized proteins, because they are only vulnerable to proteinase after physical disruption of the inner mitochondrial membrane.

Figure 2B:
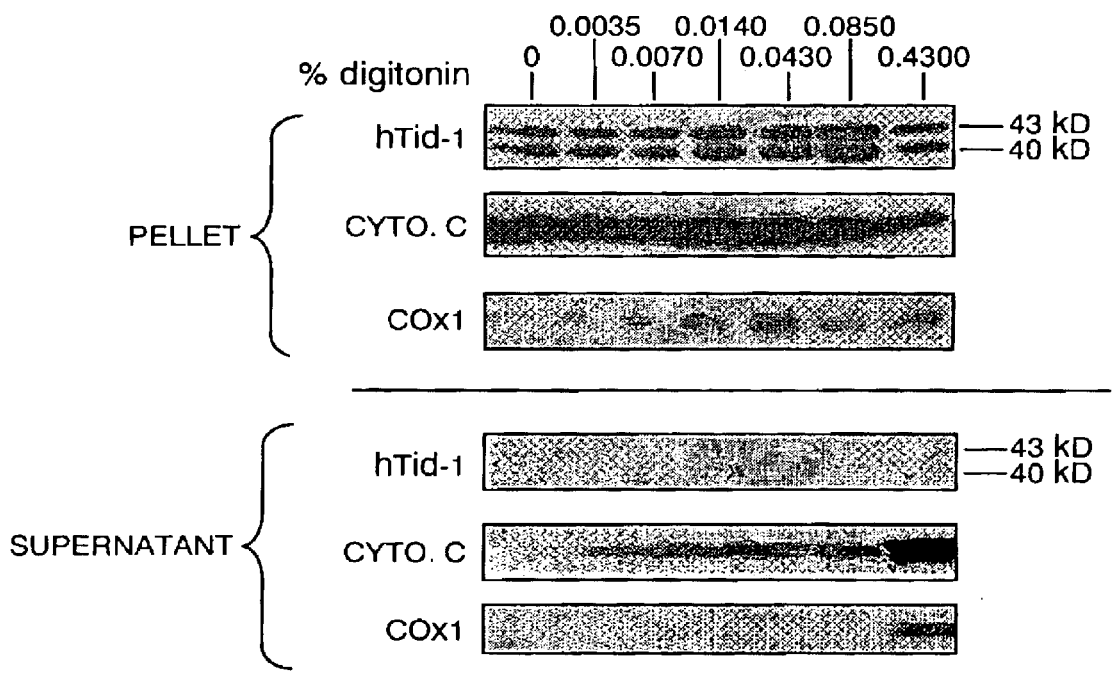
FIG. 2B. Digitonin extraction of mitochondrial proteins. Mitochondria were isolated from SAOS-2 cells and treated with the indicated amount of digitonin. The intermembrane space protein cytochrome c (cyto. c), and the integral inner membrane protein COx1 are extracted from the mitochondria, whereas hTid-$1_L$ and hTid-$1_S$ are held in the pellet by a digitonin-resistant membrane.

To confirm that hTid-1$_L$ and hTid-1$_S$ reside within the mitochondrial matrix, we extracted intermembrane proteins from isolated mitochondria with digitonin. Digitonin can selectively solubilize mitochondrial outer membranes while leaving inner membranes intact. (Hartl, F. U. et al. (1986) *Cell* 47:939–951). Mitochondria were incubated with increasing amounts of digitonin, centrifuged, and analyzed for the presence of hTid-1, cytochrome c, and COx1 in both the pellet and supernatant (FIG. 2B). Cytochrome c levels in the supernatant increased with higher digitonin concentrations, as expected for an intermembrane space protein. The integral inner membrane protein COx1 was extracted only with the highest concentration of digitonin. In contrast, hTid-1$_L$ and hTid-1$_S$ were not efficiently extracted, even at the highest concentration, indicating that both hTid-1$_L$ and hTid-1$_S$ are protected by the digitonin-resistant inner mitochondrial membrane and thus reside in the mitochondrial matrix.

Figure 2C:
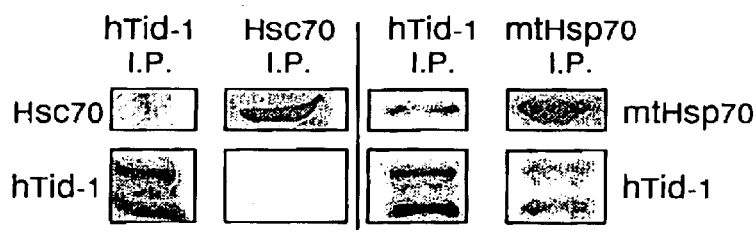
FIG. 2C. Endogenous hTid-$1_L$ and hTid-$1_S$ coimmunoprecipitate with mtHsp70. Immunoprecipitation experiments were performed from U2OS cells by using mAbs specific for either hTid-1, mtHsp70, or Hsc70. Immune complexes were analyzed by SDS/PAGE and Western blot with hTid-1-, mtHsp70-, or Hsc70-specific mAbs.

J domain proteins have been shown to interact with Hsp70-family proteins and activate their ATPase activity. Because hTid-1 proteins have extremely well conserved J domains, we suspected that they may be interacting with the mitochondrial Hsp70 homolog, mtHsp70 (GRP75), which is also localized to the mitochondrial matrix. We performed coimmunoprecipitation-immunoblot experiments by using mAbs specific for hTid-1, mtHsp70, or the constitutively expressed nonmitochondrial Hsp70 homolog Hsc70 as a control. hTid-1-specific mAbs immunoprecipitate endogenous hTid-1$_L$ and hTid-1$_S$ in complex with mtHsp70 from human U2OS cells. (FIG. 2C). In contrast, Hsc70 did not coimmunoprecipitate with hTid-1 proteins. The reverse experiment shows that mtHsp70 specific mAbs immunoprecipitate mtHsp70 in complex with hTid-1$_L$ and hTid-1$_S$. Hsc70 antibodies did not coimmunoprecipitate hTid-1 proteins. These results demonstrate that endogenous hTid-1$_L$ and hTid-1$_S$ interact specifically with a mitochondrial matrix-localized Hsp70 homolog and suggest that they may function as specificity factors in an Hsp70-like chaperone system in the mitochondrial matrix.

EXAMPLE 3 hTid-1$_L$, and hTid-1$_S$ have Opposing Effects on Apoptosis

Figure 3A:
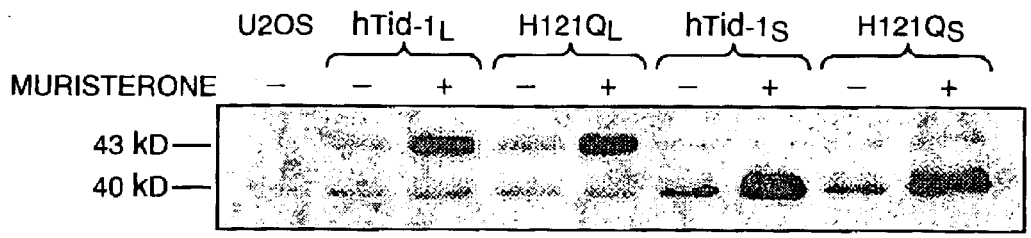
FIG. 3A. hTid-$1_L$ and hTid-$1_S$ regulate apoptosis induced by mitomycin c and TNF-. U2OS cells that express hTid-$1_L$, hTid-$1_S$, or J domain mutants (H121$Q_L$ and H121$Q_S$, respectively) from a muristerone-inducible promoter were treated with muristerone for 24 hours (+) or went untreated (−) and were analyzed by immunoblot for the presence of hTid-1 proteins.

Mitochondria are central regulators and amplifiers of apoptotic signal transduction. (Kroemer, G. et al. (1997) *Immunol. Today* 18, 44–51; Green, D. R. et al. (1998) *Science* 281, 1309–1312; Marchetti, P. et al. (1996) *J. Exp. Med.* 184, 1155–1160). On induction of apoptosis, mitochondria typically undergo a series of changes that are hallmarks of and functionally important for many forms of programmed cell death. Among these changes are the release of the caspase-activating protein cytochrome c, (Reed, J. C. (1997) *Cell* 91:559–562; Kluck, R. M. et al. (1997) *Science* 275:1132–1136; Liu, X. et al. (1996) *Cell* 86:147–157), and apoptosis inducing factor (Susin, S. A. et al. (1999) *Nature* (London) 397:441–446; Susin, S. A. et al. (1996) *J. Exp. Med.* 184:1331–1341, from the mitochondrial intermembrane space, the production of a burst of reactive oxygen species, and a dramatic permeability transition of the mitochondrial inner membrane. (Kroemer, G. et al. (1997) *Immunol. Today* 18:44–51). In addition, Bcl-2 and related apoptotic regulatory proteins localize to mitochondrial membranes and functionally regulate the mitochondrial permeability transition pore as well as cytochrome c release. (Kluck, R. M. et al. (1997) *Science* 275:1132–1136; Yang, J. et al. (1997) *Science* 275:1129–1132; Marzo, I. et al. (1998) *Science* 281:2027–2031). Given that hTid-1$_L$ and hTid-1$_S$ are localized to the mitochondrial matrix and are homologs of a Drosophila tumor suppressor, we tested whether expression of these proteins could affect apoptosis. We created a series of U2OS cells lines that express either wild-type hTid-1$_L$ or hTid-1$_S$, or J domain mutants of these proteins (H121Q$_L$ or H121 Q$_s$, respectively) from a muristerone-inducible promoter (FIG. 3A). This mutation of a highly conserved histidine residue is known to abrogate J domain-mediated activation of Hsp70 proteins in other systems. (Tsai, J. et al. (1996) *J. Biol. Chem.* 271:9347–9354; Wall, D. et al. (1994) *J. Biol. Chem.* 269:5446–5451). Because these mutations should not affect the ability of the protein to interact with substrate, they are predicted to act as dominant-negative forms of hTid-1$_L$ and hTid-1$_S$. The inducible system allowed for some basal expression of our hTid-1 constructs in the absence of muristerone, but induction of protein expression in these cells with muristerone produced protein levels approximately 5- to 10-fold above basal expression levels. On protein induction, no cytoplasmic hTid-1 proteins were detected, demonstrating that all induced proteins are targeted to the mitochondria.

Figure 3B:
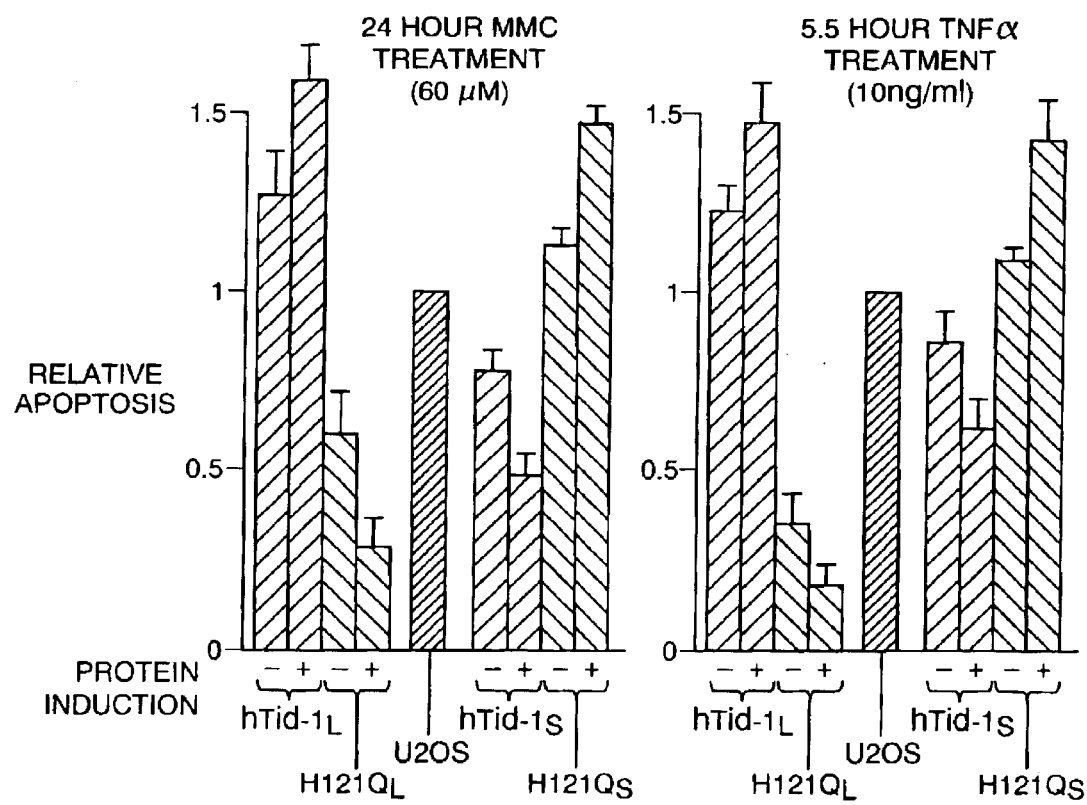
FIG. 3B. U2OS cells which express hTid-$1_L$, hTid-$1_S$ or J domain mutants from a muristerone inducible promoter were either treated with muristerone (+) or mock-treated (−) for 24 hours and treated with 60 μM MMC for 24 hours (Left), or 10 ng/ml TNF plus 30 μg/ml cycloheximide for 5.5 hours (Right), fixed, and stained with Hoechst. Apoptotic nuclei were counted and the numbers were compared with control cells. Rates of apoptosis in U2OS cells ranged from 20 to 30% for cells treated with MMC, and from 40 to 50% for cells treated with TNF. The average of at least three independent experiments is shown. Error bars are ±1 SD.

Induction of expression of protein per se did not elicit any detectable apoptosis in any of the four cell lines. However, when these cell lines were treated with either the DNA-damaging agent MMC or TNF-alpha, the cell line expressing hTid-1$_L$ showed markedly increased levels of apoptosis relative to control cells, whereas cells expressing the J domain mutant of hTid-1$_L$ (H121Q$_L$) showed decreased levels of apoptosis compared with control cells (FIGS. 3B and C). In contrast, cells expressing hTid-1$_S$ showed decreased levels of apoptosis relative to control cells, whereas cells expressing the corresponding J domain mutant (H121Q$_s$) showed increased levels of apoptosis. The various hTid-1 constructs had the greatest effects on enhancing or repressing an apoptotic response when protein was induced with muristerone. However, a more modest effect was also seen in the absence of protein induction. We attribute these effects to basal expression from the inducible promoters (FIG. 3A). Similar results were obtained with multiple independent U2OS cell lines expressing each of the four forms of hTid-1. In addition, a similar pattern of apoptosis modulation was observed in transient-transfection experiments with U2OS cells.

These results show that the two splice variants of TID1 have opposing effects on apoptosis. hTid-1$_L$ has proapoptotic activities, whereas hTid-1$_S$ has antiapoptotic activities. Significantly, these activities are J domain-dependent, because a mutation that is known to abrogate J domain-mediated activation of Hsp70 proteins in other systems (Tsai, J. et al. (1996) *J. Biol. Chem.* 271:9347–9354; Wall, D. et al. (1994) *J. Biol. Chem.* 269:5446–5451) is able to reverse the effects of the wild-type proteins, most likely by interfering with the activities of mitochondrial substrates that play important roles in propagating apoptotic signals. More specifically, we propose that because each of the mutant proteins has a different effect on apoptotic responses, each of the wild-type splice variants must have distinct cellular substrates and activities.

Figure 4A:
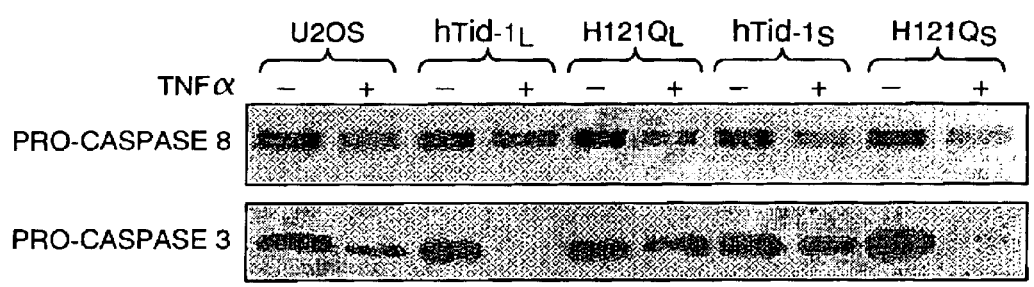
FIG. 4A. hTid-$1_L$ and hTid-$1_S$ affect the rates of caspase 3 activation and cytochrome c release but not the rate of caspase 8 activation. Inducible U2OS cells expressing hTid-$1_L$, hTid-$1_S$, or J domain mutants (H121$Q_L$ and H121$Q_S$, respectively) were treated with 10 ng/ml TNF and cycloheximide for 4.5 hours (+) or went untreated (−). Whole-cell lysates were analyzed by immunoblot for pro-caspase 8 and pro-caspase 3.
Figure 4B:
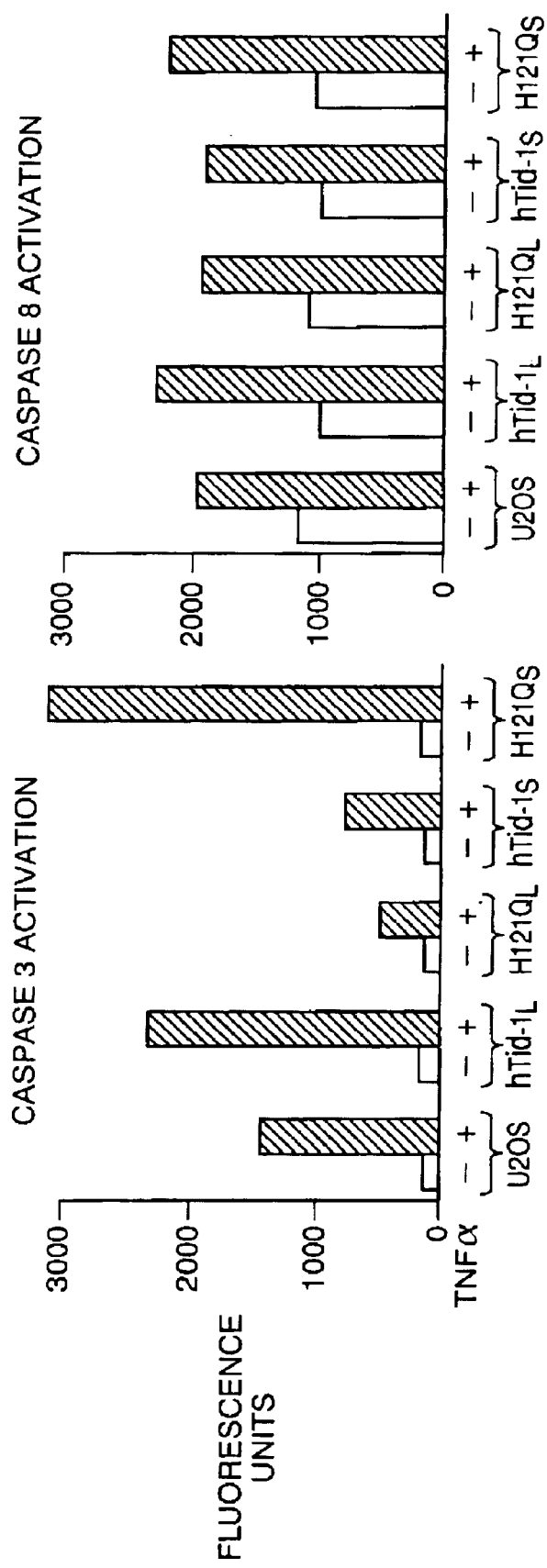
FIG. 4B. Lysates described in FIG. 4A were analyzed for ability to cleave fluorogenic caspase 8 (IETD-AFC) or caspase 3 substrates (DEVD-AFC).

EXAMPLE 4 hTid-1$_L$, and hTid-1$_S$ Affect Cytochrome c Release and Caspase 3 Activation but do not Affect Caspase 8 Activation The finding that hTid-1$_L$ and hTid-1$_S$ can modulate apoptotic signal transduction at the cellular level in response to diverse stimuli led us to examine biochemical markers to localize the effects to the mitochondria and its known downstream targets. In TNF signaling, pro-caspase 8 is cleaved and activated at the TNF receptor complex (28). Active caspase 8 cleaves Bid, which then localizes to the mitochondria and elicits a proapoptotic response, including the release of cytochrome c (Li, H. et al. (1998) *Cell* 94: 491–501; Luo, X. et al. (1998) *Cell* 94:481–490). Caspase 8 is therefore upstream of the mitochondria. Cleavage and activation of pro-caspase 3 is regulated by the release of cytochrome c from the mitochondria, (Kroemer, G. et al. (1997) *Immunol. Today* 18:44–51; Kluck, R. M. et al. (1997) *Science* 275:1132–1136; Liu, X. et al. (1996) *Cell* 86:147–157; Kluck, R. M. et al. (1997) *EMBO J.* 16:4639–4649), and is thus downstream of the mitochondria. Therefore, we examined the extent of pro-caspase 8 and pro-caspase 3 cleavage and activation in the four hTid-1-inducible cell lines on treatment with TNF by immunoblot and fluorogenic activity assays (FIGS. 4A and B). We found that cleavage and activation of pro-caspase 8 occurs at similar levels in the four cell lines. However, pro-caspase 3 was cleaved and activated more efficiently in the cell line expressing hTid-1$_L$ than in control cells and less efficiently in the H121Q$_L$ lines than in control cells. In contrast, hTid-1$_S$-expressing cells showed decreased cleavage and activation of pro-caspase 3 relative to control cells, whereas the lines expressing H121Q$_S$ showed increased activation of pro-caspase 3. Expression of hTid-1 proteins does not interfere with the normal turnover of pro-caspase 3 or 8, because their half-lives are similar in cells treated with cycloheximide alone (data not shown). These results indicate that expression of hTid-1$_L$ and hTid-1$_S$ affect apoptosis downstream of caspase 8 and upstream of caspase 3, which is consistent with a role as mitochondrial modulators of apoptosis.

Figure 4C:
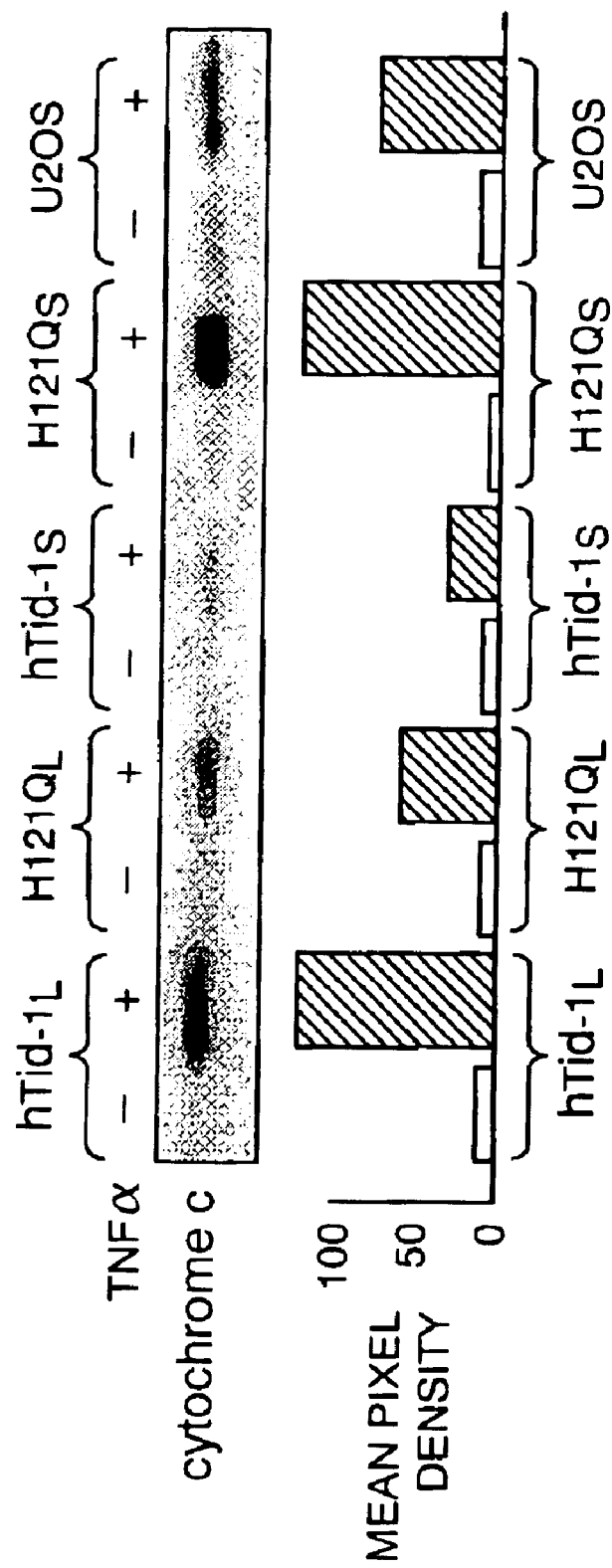
FIG. 4C. Cells described in FIG. 4A were suspended in sucrose buffer and homogenized. Samples were centrifuged at 10,000×g, and cytoplasmic extracts were analyzed by immunoblot for the presence of cytochrome c. Mean pixel densities of cytochrome c Western blot analysis are shown Lower.

We next examined the rate of cytochrome c release from mitochondria on treatment with TNF in the four inducible cell lines (FIG. 4C). Immunoblot analysis of cytoplasmic extracts of cells treated with TNF indicate that more cytochrome c is released from the mitochondria of cells expressing hTid-1$_L$ or H121Q$_S$ during apoptosis than control cells. In contrast, mitochondria from cells expressing hTid-1$_S$ or H121Q$_L$ release less cytochrome c than control cells. These results are consistent with the effects seen at the level of cell death and caspase 3 activation and further localize the activity of TID1-encoded proteins to the mitochondria.

To date, specific mitochondrial factors implicated in apoptotic function have been localized to either the outer or inner mitochondrial membrane, the intermembrane space, or part of a membrane-bound complex.

hTid-1$_L$ and hTid-1$_S$ represent a class of mitochondrial matrix-localized proteins able to modulate this process. The opposing effects of the splice variants suggest a possible regulatory mechanism in which the relative abundance of hTid-1$_L$ and hTid-1$_S$, or their cellular substrates, enable the mitochondria to either amplify or dampen apoptotic signals. Because expression of dominant-negative forms of hTid-1$_L$ and hTid-1$_S$ specifically dampen and enhance apoptotic responses, respectively, we suggest that each of the wild-type proteins has specific substrates and activities. Hence, hTid-1$_S$ is not simply a dominant negative form of hTid-1$_L$, but rather a protein with discrete activities and substrates. In addition, the different activities of the mutant splice variants rule out titration of a common binding partner, such as mtHsp70, as a mechanism of action.

The mechanism underlying the l(2)tid hyperproliferative phenotype is unclear. However, the emergence of mitochondria as regulators of apoptosis suggests that the l(2)tid imaginal disc tumors may result from a defect in mitochondrial control of apoptosis. TID1 is a highly conserved human homolog of l(2)tid and encodes two splice variants that exhibit opposing effects of apoptosis.

Hence, we propose that hTid-1$_L$ and hTid-1$_S$ modulate apoptotic effector structures in the inner mitochondrial membrane, such as components of the permeability transition pore, which is regulated by the proapoptotic Bcl-2 family member Bax (Marzo, I. et al. (1998) *Science* 281:2027–2031), or the F0F1 ATPase, which is implicated in Bax-mediated cell death. (Matsuyama, Q. et al. (1998) *Mol. Cell* 1:327–336). Alternatively, hTid-1$_L$ and hTid-1$_S$ may be part of an intramitochondrial signaling pathway that integrates disparate apoptotic initiating stimuli.

Materials and Methods:

Cell Lines and Reagents. U20S Cells were Cultured in DMEM Containing 10% Fetal Calf serum supplemented with 50 units/ml penicillin and 50 µg/ml streptomycin. Inducible hTid-1$_L$, hTid-1$_S$, H121Q$_L$, and H121Q$_S$ were expressed in U20S cells from a plasmid containing a muristerone-inducible promoter (Invitrogen). Inducible cells lines were cultured under constant selection with 50 µg/ml Zeocin (Invitrogen) and 300 µg/ml G418. Gene expression was induced with 1 µM muristerone (Invitrogen) for 24 hours. SAOS-2 cells were cultured in DMEM containing 15% fetal calf serum and 50 units/ml penicillin and 50 µg/ml streptomycin.

Antibodies.

The mAbs against hTid-1 (RS-13 and RS-11) were Produced by J. DeCaprio (Dana-Farber Cancer Institute, Boston, Mass.) by using standard methods and a glutathione S-transferase-hTid-1 fusion protein as the antigen. The cytochrome oxidase subunit 1 (COx1)- and cytochrome oxidase subunit 2 (COx2)-specific mAbs were purchased from Molecular Probes (A-6405 and A-6404, respectively). The anti-cytochrome c mAbs (65981A) and pro-caspase 8 mAbs (66231A) were purchased from PharMingen. The anti-pro-caspase 3 mAbs (C31720) were purchased from Transduction Laboratories (Lexington, Ky.). The anti-mtHsp70 mAbs (MA3-028) were purchased from Affinity Bioreagents (Golden, Colo.). The anti-Hsc70 mAbs were purchased from StressGen (Victoria, Canada) (SPA815).

PCR Cloning of hTid-1$_S$. Primers of Sequence 5'-cgagacagatgtggagggga-3' and 5'-gaataatttaaacacact-3' were used to amplify TID2-related sequences from a human fetal brain cDNA library (CLONTECH).

Subcellular and Submitochondrial Fractionation. For Subcellular Fractionation, SAOS-2 cells were trypsinized, washed in PBS, suspended in sucrose buffer (10 mM Tris HCl pH 7.5/1 mM EDTA/0.25 M sucrose/1 µg/ml each aprotinin and leupeptin/0.01% PMSF), and homogenized by 20 strokes of a Teflon tissue homogenizer (Glas-Col, Terre Haute, Id.). Nuclei were pelleted at 500×g. Mitochondria were pelleted at 10,000×g. hTid-1, COx1, and cytochromec were visualized by Western blot.

For proteinase protection assays, U2OS cells were trypsinized and homogenized in sucrose buffer, and mitochondria were isolated as described above. Mitochondrial pellet was resuspended in hypotonic buffer (5 mM Tris HCl/5 mM KCl/1.5 mM MgCl$_2$/0.1 mM EDTA/1 mM DTT, pH 7.4) for 20 minutes on ice. The sample was split into three fractions. The first fraction was left untreated. The second fraction was treated with proteinase K (50 µg/ml) for 20 minutes on ice. PMSF (0.03%) and EGTA (1 mM) were added and the fraction was subjected to sonication for 90 seconds on ice in a Sonic Dismembranator 550 (Fisher Scientific). The third fraction was subjected to sonication and treated with proteinase K as described above. The three samples were then analyzed by using SDS/PAGE and immunoblot for the presence of hTid-1, COx2, and mtHsp70.

For digitonin extraction, SAOS-2 cells were trypsinized, washed in PBS, and resuspended in sucrose buffer, and mitochondria were isolated as described above. Mitochondria were resuspended in sucrose buffer containing the indicated concentration of digitonin (Sigma) for 1 minute on ice. Fractions were then diluted 1:5 and centrifuged for 15 minutes at 10,000×g. Pellets and supernatants were then analyzed by Western blot for the presence of hTid-1, COx1, and cytochrome c.

Immunoprecipitation. One 10-cm Plate of SAOS-2 Cells was Trypsinized, Washed in PBS, and lysed in 1% NP40/150 mM NaCl/50 mM Tris HCl, pH 8.0/1 µg/ml each aprotinin and leupeptin/0.01% PMSF on ice. The sample was split into four fractions and incubated for 1 hour with either anti-hTid-1, anti-mtHsp70, or anti-Hsc70 mAbs. Immune complexes were collected on protein G agarose beads (GIBCO) and washed three times in 0.1% NP40 lysis buffer. Samples were then separated by SDS/PAGE, transferred to poly (vinylidene difluoride) membrane, and probed with either anti-mtHsp70, anti-Hsc70, or anti-hTid-1 mAbs. Proteins were visualized by ECL (Amersham Pharmacia) by using x-ray film.

Apoptosis Assays. Inducible U2OS Cells were Induced with 1 µM Muristerone for 24 hours, or went uninduced and were treated with either the indicated concentration of mitomycin c (Sigma) for 24 hours or the indicated concentration of TNF plus 30 µg/ml cycloheximide. Cells were fixed by exposure to methanol vapor for 10 minutes followed by immersion in methanol for at least 10 minutes. Cells were stained with 1 µg/ml Hoechst 33258 and 0.1% lowfat milk (Carnation) for 7 minutes and rinsed in water. Apoptotic nuclei were counted by using fluorescence microscopy. For transient-transfection experiments, U2OS cells were transfected by the calcium phosphate technique by using BES-buffered saline. (Sambrook, J. et al. (1989) *Molecular Cloning: A Laboratory Manual* (Cold Spring Harbor Laboratory Press, Plainview, N.Y.)). Six micrograms of the appropriate hTid-1 construct was transfected with 6 µg of green fluorescent protein DNA. Twenty-four hours after transfection, Hoechst 33342was added to the media at 1 µg/ml final concentration for 7 minutes. Media was then slowly removed. Cells expressing green fluorescent protein were counted and scored for apoptotic nuclei.

Caspase Activation and Cytochrome c Release Assays. U2OS Cells were Induced for 24 hours with 1 µM muristerone and treated for the indicated time with 10 ng/ml TNF plus 30 µg/ml cycloheximide. Cells were trypsinized, washed in PBS, and resuspended in lysis buffer (1% NP40/ 50 mM Tris HCl/150 mM NaCl, pH 8.0/1 µg/ml each aprotinin and leupeptin/0.01% PMSF), and protein concentration was analyzed by using the Bradford method (Bio-Rad). Sixty micrograms of total cell lysate was then analyzed by Western blot analysis using mAb specific for pro-caspase 3 and pro-caspase 8.

Caspase activity was measured by using fluorescent caspase 8 and caspase 3 activity assays (CLONTECH). Inducible U2OS cells were induced with muristerone for 24 hours and treated with 10 ng/ml TNF plus 30 µg/ml cycloheximide for 4.5 hours. Cells were trypsinized, combined with apoptotic cells in the tissue-culture media, counted, and assayed for caspase activity by the manufacturer's protocol on a fluorescent plate reader (excitiation 380 mn, emission 530 nm). For caspase 8 activity, 1×10$^6$ cells of each line were used, and for caspase 3 activity, 3.5×10$^5$ cells of each line were used.

For cytochrome c release assays, U2OS cells were induced with muristerone for 24 hours and treated with 10 ng/ml TNF plus 30 µg/ml cycloheximide for 4.5 hours. Cells were then trypsinized, resuspended in sucrose buffer, homogenized in a Teflon tissue homogenizer, and centrifuged at 10,000×g for 10 minutes as described above. Postmitochondrial supernatant (100 μg of protein) was then analyzed by Western blot analysis for the presence of cytoplasmic cytochrome c. Cytochrome c levels were quantitated by using NIH IMAGE software.

EXAMPLE 5
Mouse Tid1 Proteins

Figure 6:
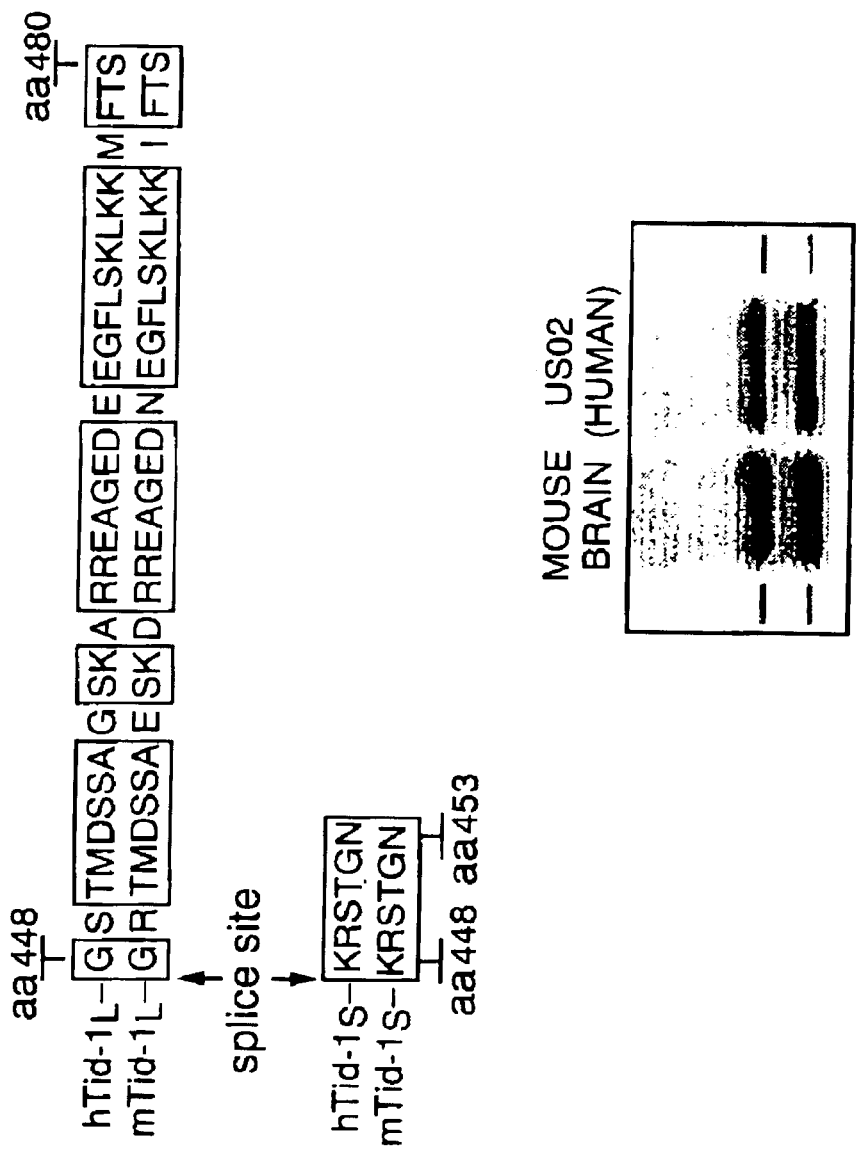
FIG. 6A. mTid-$1_L$ (SEQ ID NO: 25) and mTid-$1_S$ (SEQ ID NO: 27) are murine homologs of hTid-$1_L$ (SEQ ID NO: 24) and hTid-$1_S$ (SEQ ID NO: 26). Amino acid sequence alignment of hTid-$1_L$ and hTid-$1_S$ with the homologous murine sequences deduced from mouse EST sequences.
FIG. 6B. Detection of hTid-$1_L$ and hTid-$1_S$ in the human osteosarcoma cell lines U2OS (right) and co-migrating proteins mTid-$1_L$ and mTid-$1_S$ in murine brain tissue (left).
Figure 6B:
Figure 6A:
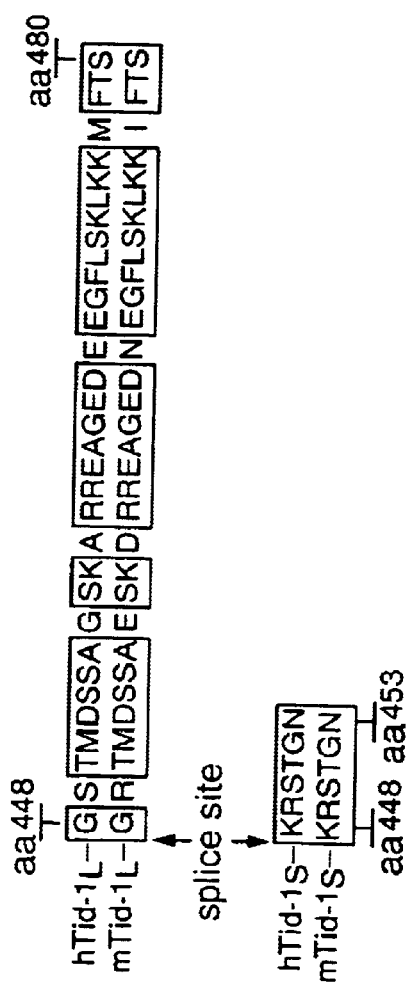

TID1 is a nuclear human gene that encodes two mitochondrial matrix localized proteins, hTid-$1_L$ and hTid-$1_S$. These two proteins differ only in their carboxyl termini; the C-terminal 33 amino acids of hTid-$1_L$ are encoded by an exon that is alternatively spliced and replaced by an exon encoding the final 6 amino acids of hTid-$1_S$. EST database searches revealed that murine homologs of both of these splice variants exist, and that their coding sequences, including their respective C-termini, are highly conserved (FIG. 6A). We analyzed mouse brain tissue by immunoblot using monoclonal antibodies specific for hTid-1 proteins. These antibodies specifically detect two proteins of 43 and 40 kD that co-migrate with hTid-$1_L$ and hTid-$1_S$, respectively on SDS-PAGE (FIG. 6B). Hence, we named these proteins mTid-$1_L$ and mTid-$1_S$.

EXAMPLE 6
Increase in Tid-$1_S$ Levels upon Th2, but not Th1, Activation

Figure 7A:
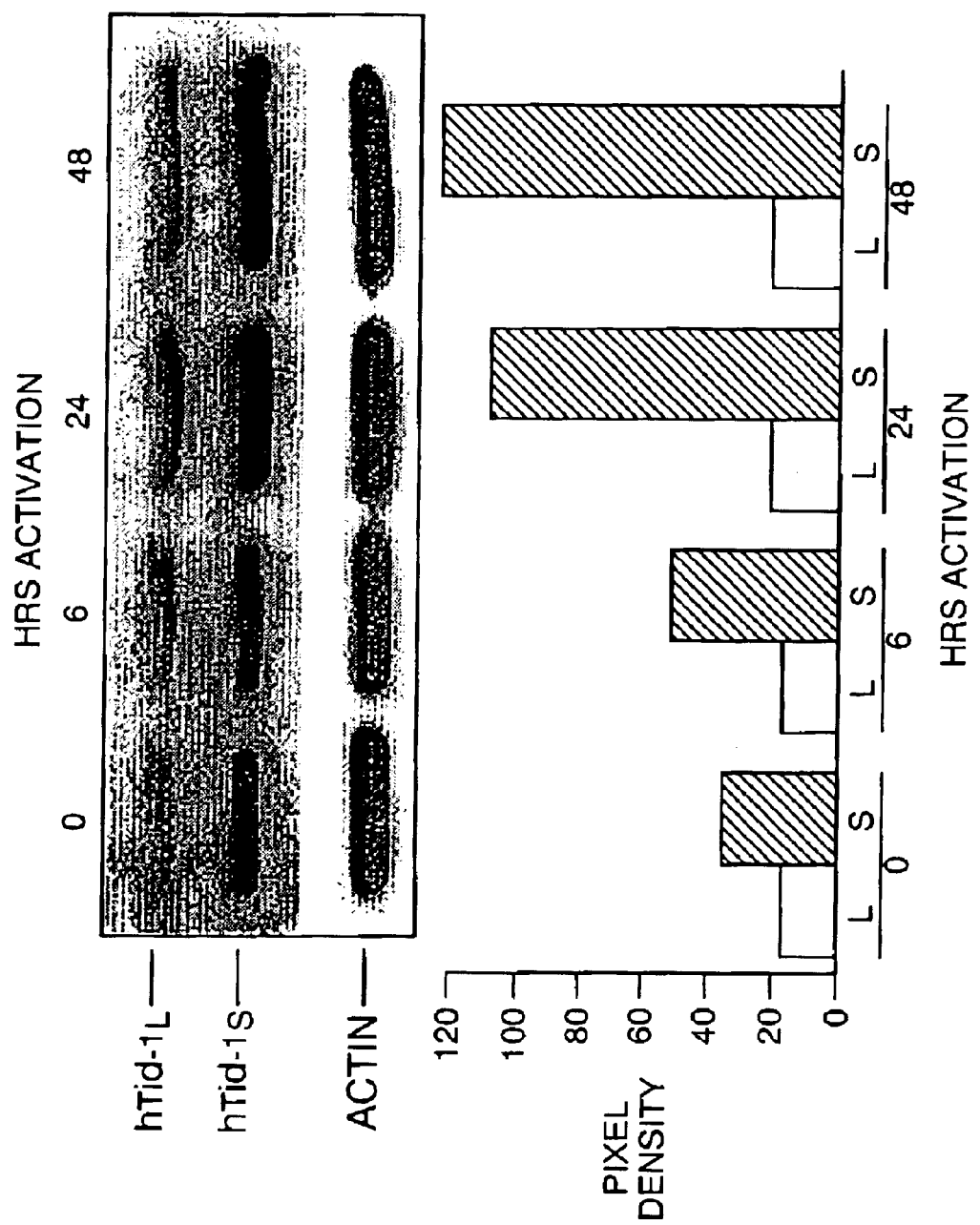
FIG. 7A. Up-regulation of hTid-$1_S$ and hTid-$1_L$ in Th2 cells during activation with PMA/ionomycin. D10 Th2 cells were activated with PMA and ionomycin over a 48 hour time course and mTid-1 levels evaluated by immunoblot analysis. Quantitation is shown underneath. The membrane was also probed with an actin antibody to ensure equal loading.
Figure 7B:
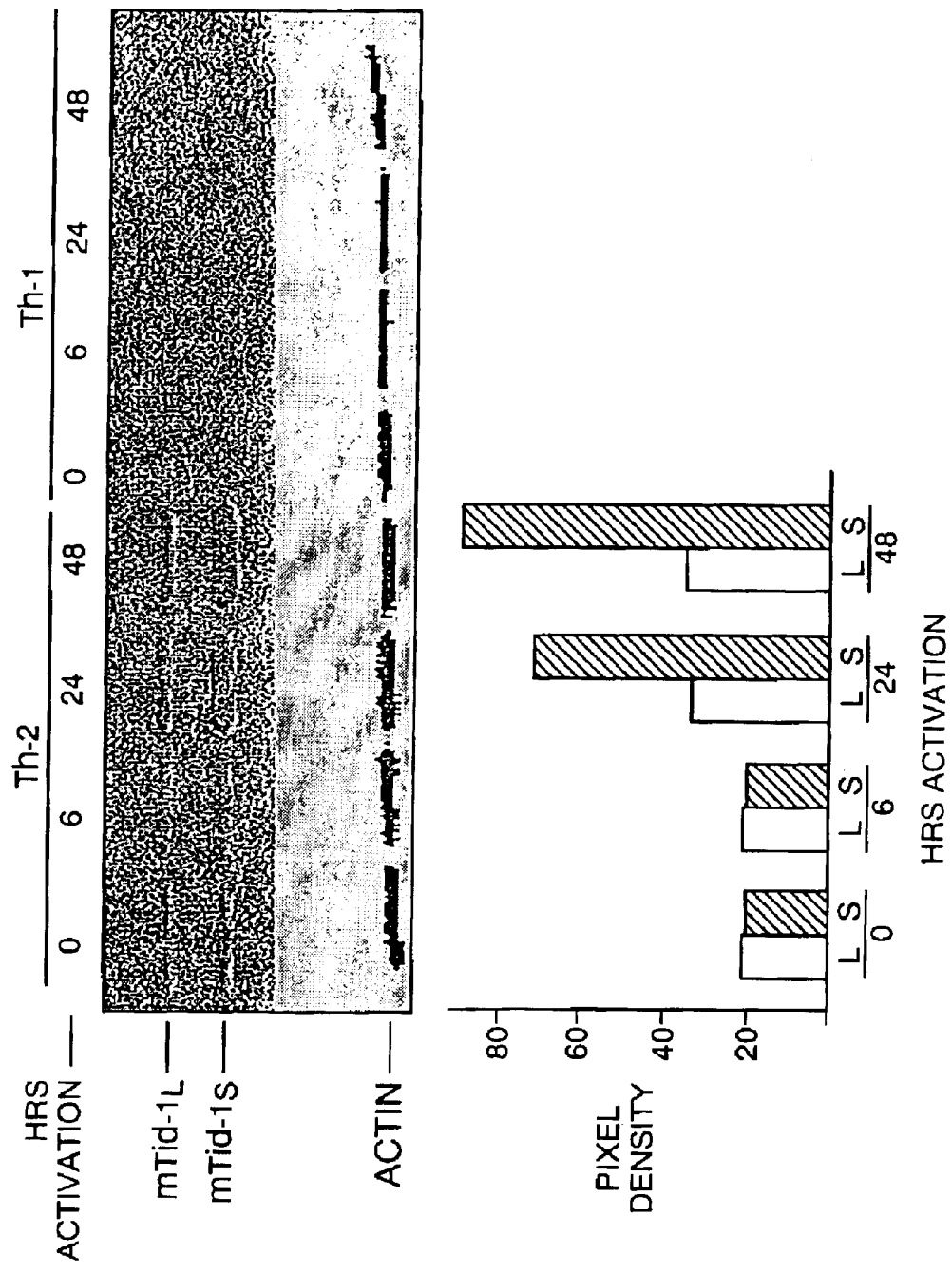
FIG. 7B. Comparison of mTid-1 levels in D10 Th2 cells (left) and D5 Th1 cells (right) during activation with PMA and ionomycin over a 48 hours time course. The membrane was also probed with an actin antibody to ensure equal loading. Quantitation is shown underneath.

The different propensities of Th1 and Th2 cells to undergo AICD led us to examine whether the relative levels of Tid-1 proteins are different in these two cell types, or if they change in response to activating signals. To this end, we activated the murine Th1 and Th2 clones D5 and D10 respectively, using the phorbolester PMA and the calcium ionophore, ionomycin. In Th2 cells, mTid-$1_S$ levels increase approximately 3 to 5 fold upon activation. Since there is no comparable increase of mTid-$1_L$ levels in Th2 cells during activation, the ratio of mTid-$1_S$ to mTid-$1_L$ protein levels is substantially altered (FIGS. 7A, B). The steady state levels of mTid-1 proteins are generally much lower in Th1 cells than in Th2 cells, and no substantial increase was observed upon activation with PMA and ionomycin (FIG. 7B and data not shown).

Figure 7C:
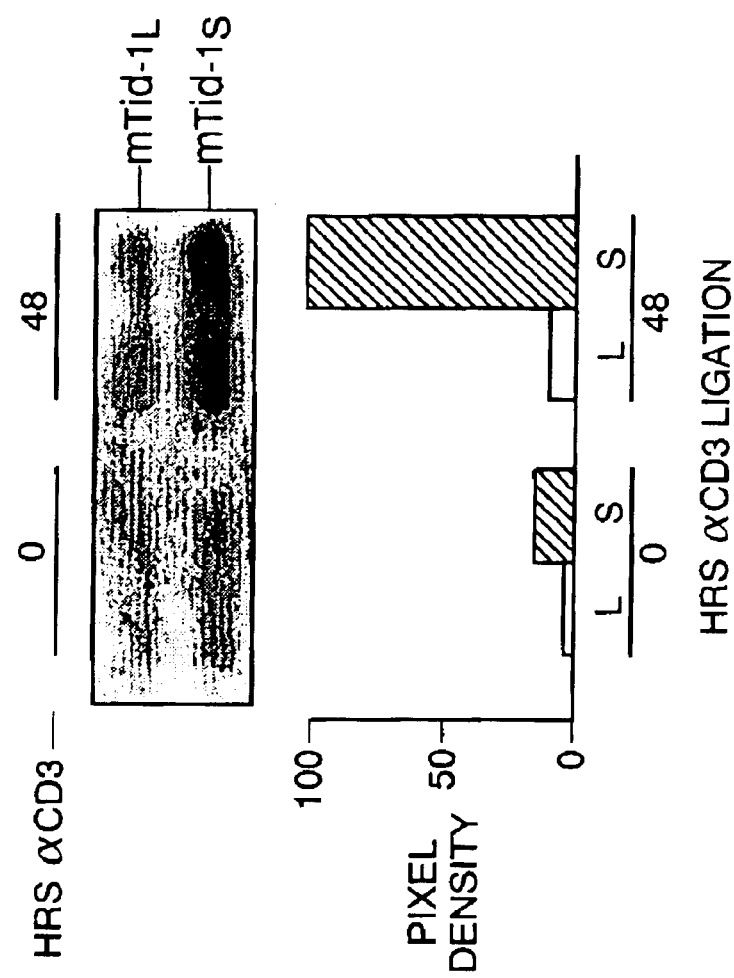
FIG. 7C. D10 Th2 cells were activated with anti-CD3ε antibody over a 48 hour time course and mTid-1 levels evaluated by immunoblot analysis. Quantitation is shown underneath.
Figure 7D:
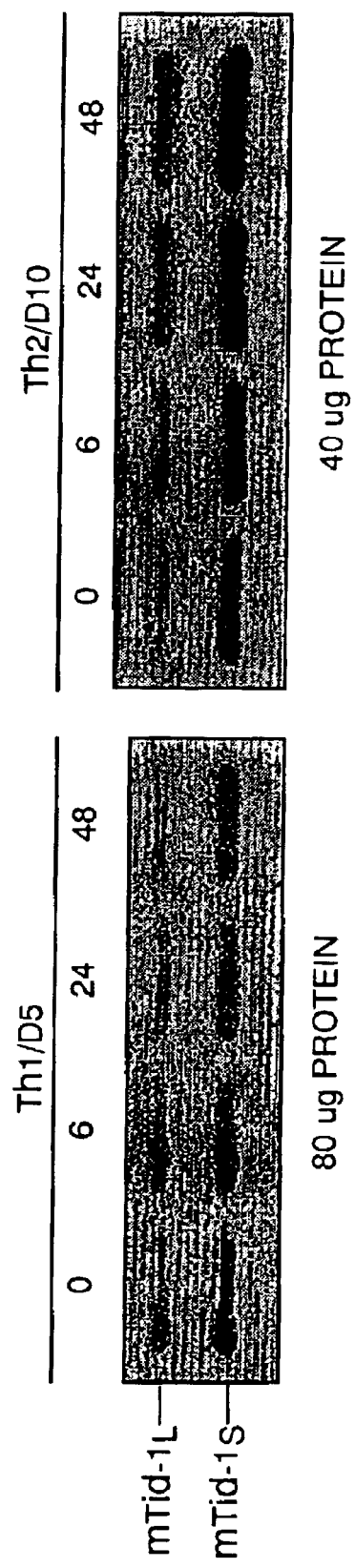
FIG. 7D. Comparison of mTid-1 levels and modulation of expression upon stimulation with anti-CD3ε antibody in D5 Th1 cells (left) and D10 Th2 cells (right). Note that 80 μg of total protein was used for the analysis in Th1 cells while 40μg was used for Th2 cells.

Though activation of helper T cells can cause cell death, activating signals generated by the TCR/CD3 complex can also result in the production of survival signals in the context of a Th2 cell. (Varadhachary, A. S. et al. (1997) *Proc Natl Acad Sci U S A* 94:5778–5783). It is thought that these TCR/CD3 generated inductive signals may be responsible for Th2 cell resistance to AICD. In order to determine if such a signal results in the upregulation of the anti-apoptotic protein hTid-$1_S$, we activated Th1 and Th2 cells by stimulating the T cell receptor complex with anti-CD3ε antibodies. Like PMA/ionomycin treatment, activation of Th2 cells with anti-CD3ε antibodies resulted in an 8 to 10 fold upregulation of mTid-$1_S$ in Th2, but not in Th1 cells (FIGS. 7C, D).

Figure 7E:
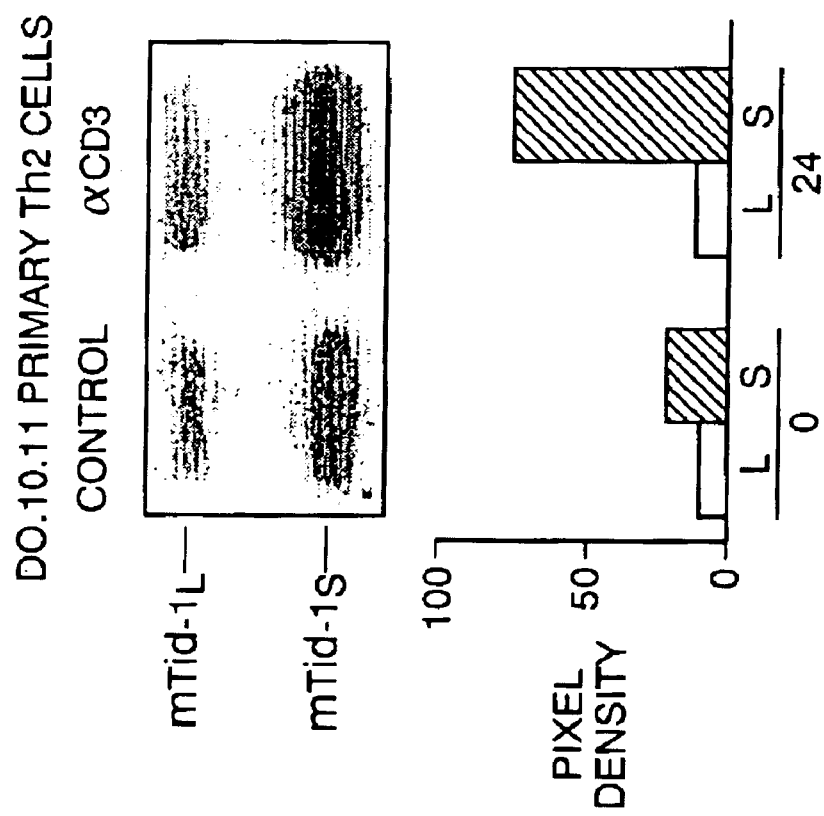
FIG. 7E. Analysis of mTid-1 protein expression upon activation of primary murine Th2 cells with anti-CD36ε antibody for 24 hours. Quantitation is shown on the right.

The D5 Th1 cells and the D10 Th2 cells are clonal T cell lines that have been used extensively to study T cell differentiation. Rao, A. et al. (1984) *J Exp Med* 159: 479–494; Agarwal, S. et al. (1998) *Immunity* 9:765–775; Kaye, J. et al. (1983) *J Exp Med* 158:836–856). In order to determine if the upregulation of mTid-$1_S$ in the D10 cells is a characteristic particular to this clone, or if occurs in other Th2 cells, we differentiated primary T cells towards a Th2 phenotype by a standard protocol. (Agarwal, S. et al. (1998) *Immunity* 9:765–775). We then activated these primary Th2 cells with anti-CD3ε antibodies, and determined mTid-1 expression. Like the Th2 cell line D10, these primary Th2 cells exhibit an increase in mTid-$1_S$ expression in response to CD3 ligation (FIG. 7E).

We also examined two additional clonal Th1 cell lines and two additional clonal Th2 cell lines for anti-CD3ε mediated induction of mTid-$1_S$ expression. Consistent with the results obtained with the D5 and D10 clones, the Th1 lines 7A5 and D1.1 exhibited no activation-induced upregulation of mTid-$1_S$. In contrast, treatment of the Th2 lines HAE 4A6 and CDC35 with anti-CD3ε for 24 hours resulted in the specific upregulation of mTid-$1_S$ (FIG. 7F).

EXAMPLE 7
Abrogation of Apoptosis Resistance by Introduction of a Tid-$1_S$ Dominant Negative Mutant The selective upregulation of the anti-apoptotic mTid-$1_S$ proteins upon activation of the AICD resistant Th2 cells suggested the possibility that mTid-$1_S$ may play a role in modulating AICD. To test this hypothesis, we transfected a plasmid encoding a mutant hTid-$1_S$ protein (H121$Q_S$) into D10 Th2 cells. This mutation of a highly conserved histidine residue in the J domain has been previously characterized and confers a dominant negative phenotype. (Syken, J. et al. (1999) *Proc Natl Acad Sci U S A* 96: 8499–8504). Mutations of homologous residues in other J-domain proteins have been shown to abolish interactions between J-domains and Hsp70 family proteins. Tsai, J. et al. (1996) *J Biol Chem* 271:9347–9354; Wall, D. et al. (1994) *J Biol Chem* 269:5446–5451). We predicted that if the activation-induced upregulation of mTid-$1_S$ contributes to establishment of resistance to AICD in Th2 cells, expression of the dominant negative H121$Q_S$ mutant should abrogate this resistance, and transfectants should die in response to activation.

Figure 8B:
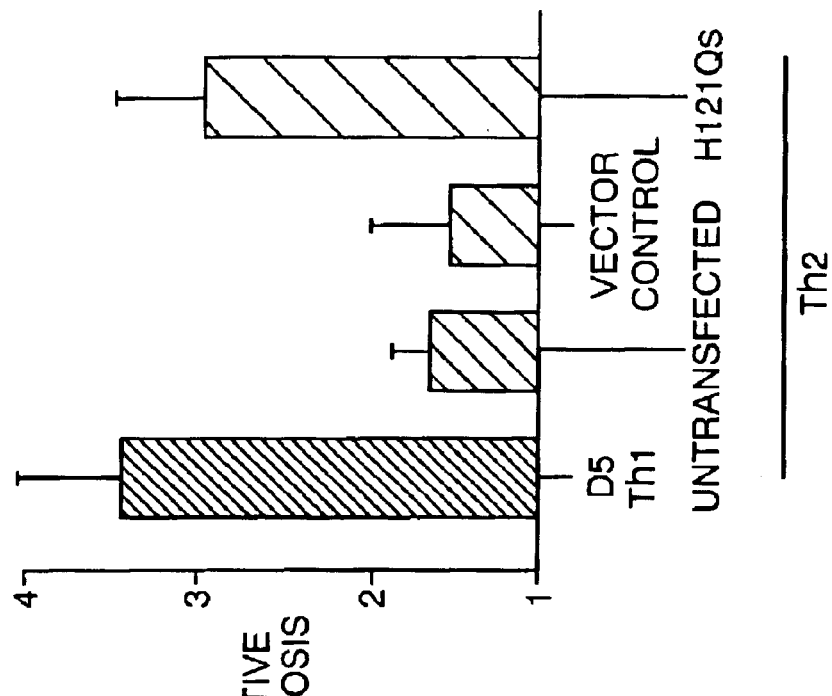
FIG. 8. The dominant negative hTid-$1_S$ mutant H121$Q_S$ abrogates resistance to AICD in D10 Th2 cells. D5 Th1 cells, untransfected D10 Th2 cells, as well as Th2 populations transfected with empty vector or a H121$Q_S$ expression vector were treated with anti-CD3ε antibody for 24 hours. Apoptosis was determined using am ELISA based assay and is presented as the relative ratio of death observed in treated versus untreated populations.
Figure 8A:

Pools of G418 resistant D10 Th2 cells transfected with either H121$Q_S$ or vector control were selected. These cells grow as well as untransfected cells, and do not exhibit increased levels of spontaneous apoptosis. Immunoblot analysis demonstrates that the cells transfected with H121$Q_S$ express the transfected protein at levels that are similar to those of the endogenous mTid-$1_S$ after activation (FIG. 8). We treated these cells, as well as vector-transfected D10 cells, untransfected D10 cells, and D5 Th1 cells with anti-CD3ε antibodies and assayed them for AICD. We found that, as reported in the literature, Th1 cells died at a higher rate than did the untransfected Th2 cells (FIG. 8A). The pool of G418-selected vector control cells died at a similarly low rate as untransfected Th2 cells. The Th2 cells expressing H121$Q_S$, however, died at an increased rate, similar to that observed for Th1 cells. These results suggest that interfering with normal mTid-$1_S$ function in Th2 cells can abrogate resistance to AICD.

Figure 9:
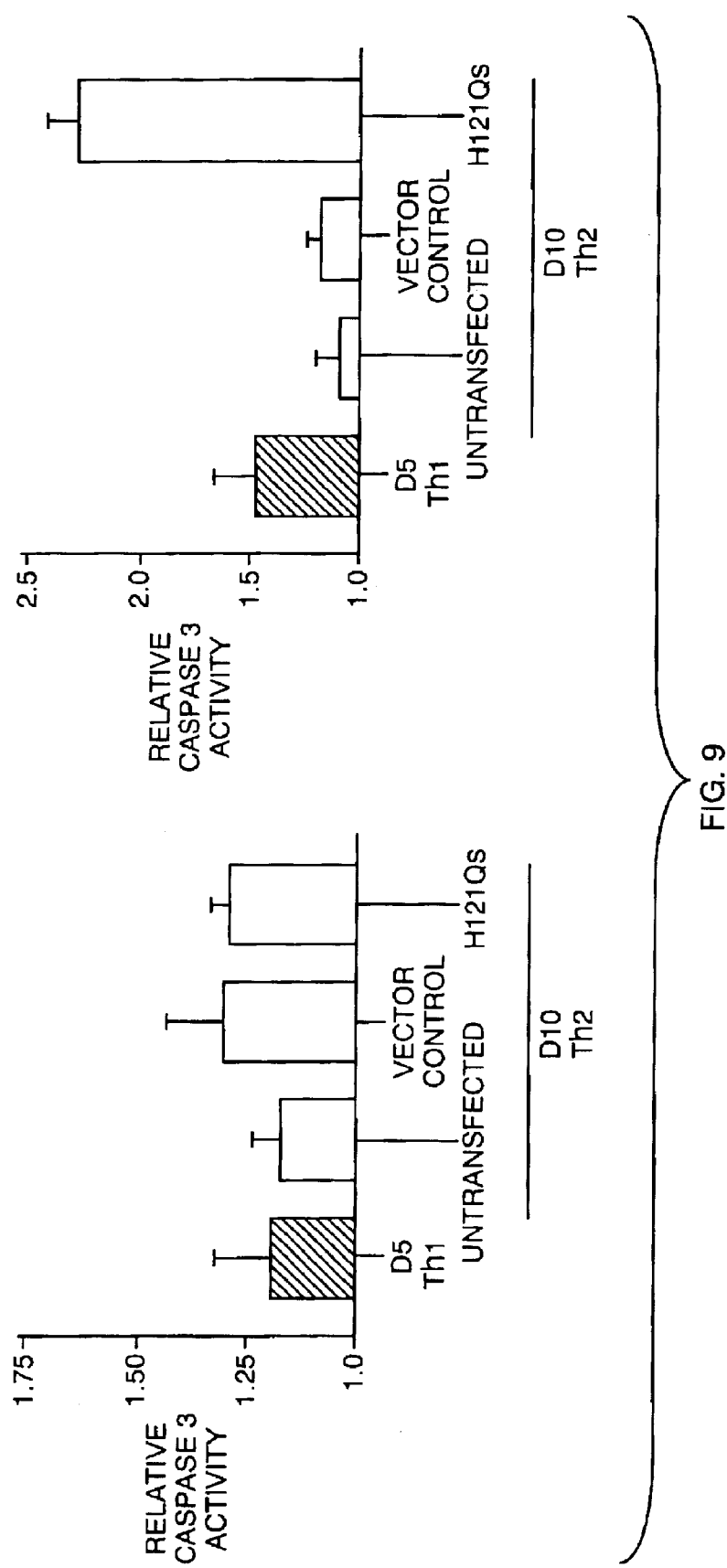
FIG. 9. Activation of caspases. D5 Th1 cells, untransfected D10 Th2 cells, as well as Th2 populations transfected with empty vector, or an H121 $Q_S$ expression vector, were treated with anti-CD3ε antibody for 24 hours. Activities of caspase 8 (left) and caspase 3 (right) were determined by specific fluorogenic activity assays.

EXAMPLE 8
Th2 Cells Expressing a Dominant Negative hTid-$1_S$ Mutant Exhibit Elevated Caspase 3 Activity In order to determine if the increased cell death observed in the H121$Q_S$ transfected pool is due altered mitochondria-dependent processes, we measured caspase activity in the different populations of T cells. Caspase 8 is activated at the Fas receptor complex. TCR/CD3 stimulation is thought to activate Fas receptors by an unknown mechanism, propagating signals through cleavage and activation of pro-caspase 8. Caspase 8 cleaves the pro-apoptotic Bcl-2 family member Bid, which then translocates to the mitochondria and elicits the release of cytochrome c. The release of cytochrome c from mitochondria leads to the activation of caspase 3 and ultimately to the demise of the cell. Thus, caspase 8 is upstream of mitochondria and caspase 3 is downstream of mitochondria. We used fluorogenic caspase activity assays to measure caspase 3 and caspase 8 activity in the H121Q$_S$ expressing D10 cells, as well as vector transfected D10 cells, untransfected D10 cells, and D5 Th1 cells at 24 hours after activation with anti-CD3ε. We found that caspase 8 activity is similar in each of the cell populations tested (FIG. 9), suggesting that a mechanism of resistance to AICD in Th2 cells may lie downstream of the Fas receptor and caspase 8 activation. Caspase 3 activity, however, is notably higher in Th1 cells than in untransfected or vector transfected Th2 cells (FIG. 9). This parallels the increased rate of AICD in Th1 cells. Most dramatically, however, Th2 cells expressing the dominant negative hTid1-$_S$ mutant H121Q$_S$, exhibit elevated caspase 3 activity relative to untransfected cells or vector control pools. These cells even exhibit somewhat higher caspase 3 activity than Th1 cells (FIG. 9), indicating that the H121Q$_S$ mutant may be enhancing mitochondria mediated amplification of cell death signals. Alternatively additional differences may exist between Th1 and Th2 cells that also contribute to the efficiency of pro-caspase 3 activation downstream of the mitochondria.

Thus, we report that expression of mTid-1$_S$, a mitochondria-localized anti-apoptotic homolog of the Drosophila tumor suppressor Tid56, is induced in Th2 helper T cells upon activation by two different methods, PMA/ionomycin and anti-CD3ε treatment. This correlates well with the anti-apoptotic activities of hTid-1$_S$, as Th2 cells are known to be resistant to AICD. Interfering with the function of mTid-1$_S$ by expression a J-domain mutant of hTid-1$_S$, abrogates the resistance of Th2 cells to AICD. Expression of this mutant protein has no effect on cell survival in the absence of activating signals. Upon activation, however, this mutant protein causes increased activation of caspase 3, an event that lies downstream of the mitochondria, without affecting the activity of caspase 8, which lies upstream of the mitochondria.

This provides the first evidence indicating that the relative levels of Tid-1 proteins can be modulated in response to a potentially lethal signal, and that TID1 encoded proteins may play a physiological role in regulating apoptosis. Importantly, this is the first stimulus that alters Tid-1 protein levels in any cellular process examined thus far including induction of apoptosis by DNA damage or TNF- and differentiation of epithelial or neuronal cells.

Though the specific mechanisms behind Th2 resistance to AICD are not known, several models have been proposed to explain this phenomenon. Th2 cells express higher levels of Fas Associated Phosphatase (FAP-1) than Th1 cells, and this may inhibit Fas mediated signaling, thus conferring resistance to AICD. (Zhang, X. et al. (1997) *J Exp Med* 185:1837–1849). Less efficient pro-caspase 8 activation in Th2 cells has also been reported. (Varadhachary, A. S. et al. (1999) *J Immunol* 163:4772–4779).

Resistance to AICD in Th2 cells is associated with activation of CD3/T cell receptor complex. (Varadhachary, A. S. et al. (1997) *Proc Natl Acad Sci USA* 94:5778–5783). The CD3/TCR complex engages different signaling pathways in Th1 and Th2 cells, supporting the idea that Th2 cell resistance to AICD and increased expression of mTid-1$_S$ may be mediated by CD3 signaling.

The activation-induced expression of mTid-1$_S$ in Th2 cells may represent a new level of resistance to AICD. As mitochondria lie downstream of most apoptotic initiating events, Tid-1 proteins are in a central position to modulate and integrate the various signals that are generated during T cell activation. This is the first example of a stimulus that consistently affects either the levels or the ratio of Tid-1$_L$ and Tid-1$_S$ protein. Moreover, this is the first physiological evidence from a mammalian system that Tid-1 protein levels are modulated, and that this modulation may be in response to a survival signal. Inhibition of mTid-1$_S$ activity by expression of a dominant negative mutant, causes Th2 cells to die at a similar rate as Th1 cells, suggesting an active role for mTid-1s in the survival of Th2 cells during activation.

Materials and Methods

Cell Culture:

All cells were cultured in Dulbecco's modified Eagle's medium supplemented with 10% fetal calf serum, L-glutamine, penicillin-streptomycin, non-essential and essential amino acids, vitamins, HEPES, and 2-mercaptoethanol. Cultures of the murine Th1 cell clones D5 (Ar-5 (Rao, A. et al. (1984) *J Exp Med* 159:479–494) and Th2 clone D10 (D10.G4.1 (Kaye, J. et al. (1983) *J Exp Med* 158:836–856)) were supplemented with 10 U/ml purified purified rat IL-2 (Collaborative Biomedical Products) and, for D10 cells, 25 U/ml recombinant IL-4 (added as supernatant from the 13L6 cell line, which was transfected with a constitutively expressed murine IL-4 cDNA). T cell clones were restimulated with antigen and irradiated antigen-presenting cells every 4 weeks; cells were expanded and used for analysis only after 2 weeks of rest following restimulation. For primary T cell analysis, spleen and lymph nodes were isolated from DO 11.10 TCR transgenic mice (typically 4–6 week old) and CD4+ cells were purified using magnetic beads (Dynal). Th2 differentiation was carried out as previously described (Agarwal, S. et al. (1998) *Immunity* 9:765–775). Differentiated T cells were analyzed at 7–10 days after primary stimulation.

Protein Detection Methods:

Cells were lysed in 1% NP40, 150 mM NaCl, 50 mM Tris-HCl, pH 8.0 and 1 μg/ml each of aprotinin and leupeptin, 0.01% PMSF for 30 minutes on ice. Samples were separated by SDS-PAGE, transferred to PVDF membranes and probed with the RS-13 anti-hTid-1 monoclonal antibody. (Kurzik-Dumke, U. et al. (1995) *Dev. Genet.* 16:64–76). Detection was by ECL (Amersham) using X-ray film or by digital acquisition using a BioRad BioFluor Max S supercooled CCD camera set up. Membranes were routinely stripped and reprobed with an actin antibody (Sigma) to ensure equal loading.

Apoptosis and Caspase Activity Assays: T cells were activated with 20 nM PMA (Phorbol 12-myristate 13-acetate, Fluka) plus 2 μM ionomycin (Fluka), or by plate bound anti-CD3ε antibodies (Biosource). Apoptosis was measured using the Cell Death Detection ELISA plus system (Roche). Cell death is expressed as percent increase relative to untreated control cells of the same type. $1 \times 10^5$ cells were used for each assay, and each experiment was performed in triplicate or quadruplicate. Caspase activity was measured using fluorescent caspase 8 and caspase 3 activity assays (Clonetech). Cells were counted and assayed for caspase activity by the manufacturer's protocol on a fluorescent plate reader. $1 \times 10^6$ cells were used for each assay.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid comprising SEQ ID NO: 3.
2. An isolated nucleic acid consisting essentially of SEQ ID NO: 3.
3. The isolated nucleic acid of claim 1 consisting of SEQ ID NO: 3.
4. The isolated nucleic acid of claim 1 operably linked to a transcriptional control sequence.
5. A vector comprising the nucleic acid of claim 4.
6. A cell comprising the nucleic acid of claim 4.
7. An isolated nucleic acid which encodes a polypeptide comprising SEQ ID NO: 9.
8. An isolated nucleic acid which encodes a polypeptide consisting essentially of SEQ ID NO: 9.
9. The isolated nucleic acid of claim 7 which encodes the polypeptide consisting of SEQ ID NO: 9.
10. An isolated nucleic acid which encodes a polypeptide comprising SEQ ID NO: 11.
11. An isolated nucleic acid which encodes a polypeptide consisting essentially of SEQ ID NO: 11.
12. The isolated nucleic acid of claim 10 which encodes the polypeptide consisting of SEQ ID NO: 11.
13. An isolated nucleic acid which encodes a polypeptide comprising SEQ ID NO: 30.
14. An isolated nucleic acid which encodes a polypeptide consisting essentially of SEQ ID NO: 30.
15. The isolated nucleic acid of claim 13 which encodes the polypeptide consisting of SEQ ID NO 30.
16. An isolated nucleic acid comprising SEQ ID NO: 5.
17. An isolated nucleic acid consisting essentially of SEQ ID NO: 5.
18. The isolated nucleic acid of claim 16 consisting of SEQ ID NO: 5.
19. The isolated nucleic acid of any one of claims 7–12, 13–15 or 2–18 operably linked to a transcriptional control sequence.
20. A vector comprising the nucleic acid of any one of claims 7–12 13–15 or 2–18.
21. A cell comprising the nucleic acid of any one of claims 7–12 13–15 or 2–18.
22. A method for producing a polypeptide comprising SEQ ID No: 9, wherein the method comprises transfecting a cell with a nucleic acid of claim 8, culturing the cell in conditions suitable for expression of the nucleic acid, and isolating the polypeptide from the cell or culture medium.
23. A method for producing a polypeptide comprising SEQ ID No: 9, wherein the method comprises transfecting a cell with a nucleic acid of claim 7 operably linked to a transcriptional control sequence, culturing the cell in conditions suitable for expression of the nucleic acid, and isolating the polypeptide from the cell or culture medium.
24. A method for producing a polypeptide consisting essentially of SEQ ID No: 9, wherein the method comprises transfecting a cell with a nucleic acid of claim 8 operably linked to a transcriptional control sequence, culturing the cell in conditions suitable for expression of the nucleic acid, and isolating the polypeptide from the cell or culture medium.

25. A method for producing a polypeptide consisting essentially of SEQ ID No: 9, wherein the method comprises transfecting a cell with a nucleic acid of claim 2 operably linked to a transcriptional control sequence, culturing the cell in conditions suitable for expression of the nucleic acid, and isolating the polypeptide from the cell or culture medium.

26. A method for producing a polypeptide consisting of SEQ ID No: 9, wherein the method comonses transfecting a cell with a nucleic acid of claim 9 operably linked to a transcriptional control sequence, culturing the cell in conditions suitable for expression of the nucleic acid, and isolating the polypeptide from the cell or culture medium.

27. A method for producing a polypeptide consisting of SEQ ID No: 9, wherein the method comprises transfecting a cell with a nucleic acid of claim 3 operably linked to a transcriptional control sequence, culturing the cell in conditions suitable for expression of the nucleic acid, and isolating the polypeptide from the cell or culture medium.

28. A method for producing a polypeptide comprising SEQ ID No: 11, wherein the method comprises transfecting a cell with a nucleic acid of claim 10 operably linked to a transcriptional control sequence, culturing the cell in conditions suitable for expression of the nucleic acid, and isolating the polypeptide from the cell or culture medium.

29. A method for producing a polypeptide comprising SEQ ID No: 11, wherein the method comprises transfecting a cell with a nucleic acid of claim 16 operably linked to a transcriptional control sequence, culturing the cell in conditions suitable for expression of the nucleic acid, and isolating the polypeptide from the cell or culture medium.

30. A method for producing a polypeptide consisting essentially of SEQ ID No: 11, wherein the method comprises transfecting a cell with a nucleic acid of claim 11 operably linked to a transcriptional control sequence, culturing the cell in conditions suitable for expression of the nucleic acid, and isolating the polypeptide from the cell or culture medium.

31. A method for producing a polypeptide consisting essentially of SEQ ID No: 11, wherein the method comprises transfecting a cell with a nucleic acid of claim 17 operably linked to a transcriptional control sequence, culturing the cell in conditions suitable for expression of the nucleic acid, and isolating the polypeptide from the cell or culture medium.

32. A method for producing a polypeptide consisting of SEQ ID No: 11, wherein the method comprises transfecting a cell with a nucleic acid of claim 12 operably linked to a transcriptional control sequence, culturing the cell in conditions suitable for expression of the nucleic acid, and isolating the polypeptide from the cell or culture medium.

33. A method for producing a polypeptide consisting of SEQ ID No: 11, wherein the method comprises transfecting a cell with a nucleic acid of claim 18 operably linked to a transcriptional control sequence, culturing the cell in conditions suitable for expression of the nucleic acid, and isolating the polypeptide from the cell or culture medium.

34. A method for producing a polypeptide comprising SEQ ID No: 30, wherein the method comprises transfecting a cell with a nucleic acid of claim 13 operably linked to a transcriptional control sequence, culturing the cell in conditions suitable for expression of the nucleic acid, and isolating the polypeptide from the cell or culture medium.

35. A method for producing a polypeptide consisting essentially of SEQ ID No: 30, wherein the method comprises transfecting a cell with a nucleic acid of claim 14 operably linked to a transcriptional control sequence, culturing the cell in conditions suitable for expression of the nucleic acid, and isolating the polypeptide from the cell or culture medium.

36. A method for producing a polypeptide consisting of SEQ ID No: 30, wherein the method comprises transfecting a cell with a nucleic acid of claim 15 operably linked to a transcriptional control sequence, culturing the cell in conditions suitable for expression of the nucleic acid, and isolating the polypeptide from the cell or culture medium.

\* \* \* \* \*